US011351237B2

(12) United States Patent
Snyder et al.

(10) Patent No.: US 11,351,237 B2
(45) Date of Patent: Jun. 7, 2022

(54) CMV-BASED INTRA-TUMORAL CANCER THERAPIES

(71) Applicant: THOMAS JEFFERSON UNIVERSITY, Philadelphia, PA (US)

(72) Inventors: Christopher M. Snyder, Haddonfield, NJ (US); Daniel A. Erkes, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 314 days.

(21) Appl. No.: 16/064,906

(22) PCT Filed: Dec. 21, 2016

(86) PCT No.: PCT/US2016/068084
§ 371 (c)(1),
(2) Date: Jun. 21, 2018

(87) PCT Pub. No.: WO2017/112797
PCT Pub. Date: Jun. 29, 2017

(65) Prior Publication Data
US 2020/0164054 A1   May 28, 2020

Related U.S. Application Data

(60) Provisional application No. 62/271,167, filed on Dec. 22, 2015.

(51) Int. Cl.
| A61K 39/395 | (2006.01) |
| A61P 35/00 | (2006.01) |
| C12N 7/00 | (2006.01) |
| A61K 39/00 | (2006.01) |

(52) U.S. Cl.
CPC .. *A61K 39/001192* (2018.08); *A61K 39/0011* (2013.01); *A61K 39/3955* (2013.01); *A61P 35/00* (2018.01); *C12N 7/00* (2013.01); *A61K 2039/5252* (2013.01); *A61K 2039/5254* (2013.01); *A61K 2039/5256* (2013.01); *A61K 2039/54* (2013.01); *A61K 2039/572* (2013.01); *C12N 2710/16134* (2013.01)

(58) Field of Classification Search
None
See application file for complete search history.

(56) References Cited

U.S. PATENT DOCUMENTS

| 6,884,414 | B1 | 4/2005 | Palese et al. |
| 8,012,490 | B2 | 9/2011 | Palese et al. |
| 2004/0132988 | A1 | 7/2004 | Johsnon et al. |
| 2009/0297555 | A1 | 12/2009 | Kemble et al. |
| 2011/0104101 | A1 | 5/2011 | Lattime |
| 2012/0289760 | A1 | 11/2012 | Hill et al. |
| 2013/0136768 | A1 | 5/2013 | Picker et al. |
| 2014/0377294 | A1 | 12/2014 | Fueyo-Margareto et al. |
| 2015/0307850 | A1 | 10/2015 | Fu et al. |

OTHER PUBLICATIONS

Szomolanyi-Tsuda, E., et al., Role for TLR2 in NK cell-mediated control of murine cytomegalovirus in vivo, J Virol, vol. 80, No. 9, pp. 4286-4291, 2006.
Thompson, E.D., et al., "Tumor masses support naive T cell infiltration, activation, and differentiation into effectors", The Journal of Experimental Medicine, vol. 207, No. 8, pp. 1791-1804, 2010.
Turula, H., et al., Competition between T cells maintains clonal dominance during memory inflation induced by MCMV, European Journal of Immunology, vol. 43, No. 5, pp. 1252-1263, 2013.
Van De Berg, P.J., et al., "Cytomegalovirus-induced effector T cells cause endothelial cell damage", Clin Vaccine Immunol, vol. 19, No. 5, pp. 772-779, 2012.
Van Stipdonk, M.J., et al., "Design of agonistic altered peptides for the robust induction of CTL directed towards H-2Db in complex with the melanoma-associated epitope gp100", Cancer Research, vol. 69, No. 19, pp. 7784-7792, 2009.
Wagner, M., et al., "Systematic Excision of Vector Sequences from the BAC-Cloned Herpesvirus Genome during Virus Reconstitution", Journal of Virology, vol. 73, No. 8, pp. 7056-7060, 1999.
Wakim, L.M., et al., "CD8(+) T-cell attenuation of cutaneous herpes simplex virus infection reduces the average viral copy number of the ensuing latent infection", Immunol Cell Biol, vol. 86, No. 8, pp. 666-675, 2008.
Wherry, E.J., "T cell exhaustion", Nature Immunology, vol. 12, No. 6, pp. 492-499, 2011.
Woller, N., et al., "Oncolytic viruses as anticancer vaccines", Frontiers in Oncology, vol. 4, Article 188, 13 pages, 2014.
Xu, G., et al., "Cytomegalovirus-based cancer vaccines expressing TRP2 induce rejection of melanoma in mice", Biochem Biophys Res Commun, vol. 437, No. 2, pp. 287-291, 2013.
Yamazaki, D., et al., "WAVE2 is required for directed cell migration and cardiovascular development", Nature, vol. 424, No. 6947, pp. 452-456, 2003.
Zurbach, K.A., et al., "Resolving the titer of murine cytomegalovirus by plaque assay using the M2-10B4 cell line and a low viscosity overlay", Virology Journal, vol. 11, No. 71, 9 pages, 2014.
Andtbacka, R.H., et al., "Talimogene Laherparepvec Improves Durable Response Rate in Patients with Advanced Melanoma", Journal of Clinical Oncology, vol. 33, No. 25, pp. 2780-2788, 2015.
Arvin, A.M., et al., "Vaccine Development to Prevent Cytomegalovirus Disease: Report from the National Vaccine Advisory Committee", Clinical Infectious Disease, vol. 39, pp. 233-239, 2004.
Azimi, F., et al., "Tumor-infiltrating lymphocyte grade is an independent predictor of sentinel lymph node status and survival in patients with cutaneous melanoma", Journal of Clinical Oncology, vol. 30, No. 21, pp. 2678-2683, 2012.
Barlett, D.L., et al., "Oncolytic viruses as therapeutic cancer vaccines", Molecular Cancer, vol. 12, No. 103, 16 pages, 2013.
Bate, S.L., et al., "Cytomegalovirus seroprevalence in the United States: the national health and nutrition examination surveys 1988-2004", Clinical Infectious Disease, vol. 50, No. 11, pp. 1439-1447, 2010.

(Continued)

*Primary Examiner* — Nicole Kinsey White
(74) *Attorney, Agent, or Firm* — Riverside Law LLP

(57) ABSTRACT

A CMV-based vaccine that promotes immune-mediated destruction of cancer through a onetime or repeated intra-tumoral administration of a recombinant CMV to generate a robust, long-lasting anti-tumor immune response.

14 Claims, 41 Drawing Sheets

(56) References Cited

OTHER PUBLICATIONS

Bayer, C., et al., "Human cytomegalovirus infection of M1 and M2 macrophages triggers inflammation and autologous T-cell proliferation", Journal of Virology, vol. 87, No. 1, pp. 67-79, 2013.
Bentz, G.L., et al., "Human CMV infection of endothelial cells induces an angiogenic response through viral binding to EGF receptor and beta1 and beta3 integrins", PNAS, vol. 105, No. 14, pp. 5531-5536, 2008.
Boehme, K.W., et al., "Human Cytomegalovirus Envelope Glycoproteins B and H are Necessary for TLR2 Activation in Permissive Cells", The Journal of Immunology, vol. 177, pp. 7094-7102, 2006.
Borst, E.M., et al., "Use of bacterial artificial chromosomes in generating targeted mutations in human and mouse cytomegaloviruses", Current Protocols in Immunology, vol. 77, No. 1, Chapter 10, pp. 10.32.1-10.32.30, 2007.
Chan, G., et al., "Transcriptome Analysis Reveals Human Cytomegalovirus Reprograms Monocyte Differentiation toward an M1 Macrophage", The Journal of Immunology, vol. 181, No. 1, pp. 698-711, 2008.
Chan, G., et al., "Activation of EGFR on monocytes is required for human cytomegalovirus entry and mediates cellular motility", PNAS, vol. 106, No. 52, pp. 22369-22374, 2009.
Chanmee, T., et al., "Tumor-associated macrophages as major players in the tumor microenvironment", Cancers (Basel), vol. 6, No. 3, pp. 1670-1690, 2014.
Daley-Bauer, L.P., et al., Cytomegalovirus hijacks CX3CR1 (hi) patrolling monocytes as immune-privileged vehicles for dissemination in mice, Cell Host Microbe, vol. 15, No. 3, pp. 351-362, 2014.
Dekhtiarenko, I., et al., "The context of gene expression defines the immunodominance hierarchy of cytomegalovirus antigens", The Journal of Immunology, vol. 190, pp. 3399-3409, 2013.
Farrington, L.A., et al., "Competition for antigen at the level of the APC is a major determinant of immunodominance during memory inflation in murine cytomegalovirus infection", The Journal of Immunology, vol. 190, pp. 3410-3416, 2013.
FDA approves first-of-its-kind product for the treatment of melanoma, http://www.fda.gov/NewsEvents/Newsroom/PressAnnouncements/ucm469571.htm, 2015.
Gabrilovich, D.I., et al., "Coordinated regulation of myeloid cells by tumours", Nat Rev Immunology, vol. 12, No. 4, pp. 253-268, 2012.
Hailemichael, Y., et al., "Cancer vaccines: Trafficking of tumor-specific T cells to tumor after therapeutic vaccination", Int J Biochem Cell Biol, vol. 53, pp. 46-50, 2014.
Hansen, S.G., et al., "Effector memory T cell responses are associated with protection of rhesus monkeys from mucosal simian immunodeficiency virus challenge", Nat Med, vol. 15, No. 3, pp. 293-299, 2009.
Hansen, S.G., et al., "Evasion of CD8+ T cells is critical for superinfection by cytomegalovirus", Science, vol. 328, No. 5974, pp. 102-106, 2010.
Hansen, S.G., et al., "Profound early control of highly pathogenic SIV by an effector memory T-cell vaccine", Nature, vol. 473, No. 7348, pp. 523-527, 2011.
Hansen, S.G., et al., "Immune clearance of highly pathogenic SIV infection", Nature, vol. 502, No. 7469, pp. 100-104, 2013.
Hemminki, O., et al., "Immunological data from cancer patients treated with Ad5/3-E2F-Δ24-GMCSF suggests utility for tumor immunotherapy", Oncotarget, vol. 6, No. 6, pp. 4467-4481, 2015.
Heo, J., et al., "Randomized dose-finding clinical trial of oncolytic immunotherapeutic vaccinia JX-594 in liver cancer", Nat Med, vol. 19, No. 3, pp. 329-336, 2013.
Hertoghs, K.M., et al., "Molecular profiling of cytomegalovirus-induced human CD8+ T cell differentiation", J Clin Invest, vol. 120, No. 11, pp. 4077-4090, 2010.
Holtappels, R., et al., "Enrichment of Immediate-Early 1 (m123/pp89) Peptide-Specific CD8 T Cells in a Pulmonary CD62L1o Memory-Effector Cell Pool during Latent Murine Cytomegalovirus Infection of the Lungs", Journal of Virology, vol. 74, No. 24, pp. 11495-11503, 2000.
Holtappels, R., et al., "Processing and Presentation of Murine Cytomegalovirus pORFm164-Derived Peptide—in Fibroblasts in the Face of All Viral Immunosubversive Early Gene Functions", Journal of Virology, vol. 76, No. 12, pp. 6044-6053, 2002.
Karrer, U., et al., Expansion of Protective CD8+ T-Cell Responses Driven by Recombinant Cytomegaloviruses, Journal of Virology, vol. 78, No. 5, pp. 2255-2264, 2004.
Keil, G.M., et al., "Immediate-Early Genes of Murine Cytomegalovirus: Location, Transcripts, and Translation Products", Journal of Virology, vol. 61, No. 2, pp. 526-533, 1987.
Klebanoff, C.A., et al., "Therapeutic cancer vaccines: are we there yet?", Immunol Rev, vol. 239, No. 1, pp. 27-44, 2011.
Klyushnenkova, E.N., et al., "A cytomegalovirus-based vaccine expressing a single tumor-specific CD8+ T-cell epitope delays tumor growth in a murine model of prostate cancer", J Immunother, vol. 35, No. 5, pp. 390-399, 2012.
Komatsu, H., et al., "Population analysis of antiviral T cell responses using MHC class I-peptide tetramers", Clinical and Experimental Immunology, vol. 134, No. 1, pp. 9-12, 2003.
Lanier, L.L., "Evolutionary struggles between NK cells and viruses", Nature Reviews Immunology, vol. 8, No. 4, pp. 259-268, 2008.
Larocca, C., et al., "Viral vector-based therapeutic cancer vaccines", Cancer J, vol. 17, No. 5, pp. 359-371, 2011.
Lichty, B.D., et al., "Going viral with cancer immunotherapy", Nature Reviews Cancer, vol. 14, No. 8, pp. 559-567, 2014.
Liu, L., et al., "Epidermal injury and infection during poxvirus immunization is crucial for the generation of highly protective T cell-mediated immunity" Nature Medicine, vol. 16, pp. 224-227, 2010.
Lloyd, M.L., et al., "Immunocontraception is Induced in BALB/c Mice Inoculated With Murine Cytomegalovirus Expressing Mouse Zona Pellucida 3", Biology of Reproduction, vol. 68, No. 6, pp. 2024-2032, 2003.
Marabelle, A., et al., "Intratumoral immunization: a new paradigm for cancer therapy", Clin Cancer Res, vol. 20, No. 7, pp. 1747-1756, 2004.
Miest, T.S., et al., "New viruses for cancer therapy: meeting clinical needs", Nature Reviews Microbiology, vol. 12, No. 1, pp. 23-34, 2014.
Munks, M.W., et al., "Genome-Wide Analysis Reveals a Highly Diverse CD8 T Cell Response to Murine Cytomegalovirus", The Journal of Immunology, vol. 176, No. 6, pp. 3760-3766, 2006.
Nannmark, U., et al., "Microvessel Origin and Distribution in Pulmonary Metastases of B16 Melanoma: Implication for Adoptive Immunotherapy", Cancer Research, vol. 55, pp. 4627-4632, 1995.
Qiu, Z., et al., "Cytomegalovirus based vaccine expressing a modified tumor antigen induces potent tumor-specific CD8+ T-cell response and protects mice from melanoma", Cancer Immunology Research, vol. 3, No. 5, pp. 536-546, 2015.
Reddehase, M.J., et al., "Late-Phase Expression of a Murine Cytomegalovirus Immediate-Early Antigen Recognized by Cytolytic T Lymphocytes", Journal of Virology, vol. 60, No. 3, pp. 1125-1129, 1986.
Schreiber, R.D., et al., "Cancer immunoediting: integrating immunity's roles in cancer suppression and promotion", Science, vol. 331, No. 6024, pp. 1565-1570, 2011.
Sell, S., et al., "Control of murine cytomegalovirus infection by gammadelta T cells", PLoS Pathog, vol. 11, No. 2, e1004481, 21 pages, 2015.
Sierro, S., et al., "Evolution of diverse antiviral CD8+ T cell populations after murine cytomegalovirus infection", European Journal of Immunology, vol. 35, pp. 1113-1123, 2005.
Singh, M., et al., "Intratumoral immunotherapy for melanoma", Cancer Immunology Immunotherapy, vol. 64, No. 7. pp. 911-921, 2015.
Smith, C.J., et al., "Systemic hematogenous maintenance of memory inflation by MCMV infection", PLoS Pathogens, vol. 10, No. 7, e1004233, 18 pages, 2014.

(56) References Cited

OTHER PUBLICATIONS

Smith, C.J., et al., "Murine CMV Infection Induces the Continuous Production of Mucosal Resident T Cells", Cell Rep, vol. 13, No. 6, pp. 1137-1148, 2015.

Smith, M.S., et al., "Human Cytomegalovirus Induces Monocyte Differentiation and Migration as a Strategy for Dissemination and Persistence", Journal of Virology, vol. 78, No. 9, pp. 4444-4453, 2004.

International Search Report and Written Opinion of PCT/US2016/068084 dated May 4, 2017.

Days Post Tumor Rechallenge

CMV-BASED INTRA-TUMORAL CANCER THERAPIES

CROSS-REFERENCE TO RELATED APPLICATIONS

This application is a National Phase under 35 U.S.C. 371 of International Application No. PCT/US2016/068084, filed Dec. 21, 2016, which claims the benefit of provisional application 62/271,167 filed Dec. 22, 2015, which are hereby incorporated by reference in their entirety.

FIELD OF INVENTION

The present invention is generally related to cancer immunotherapy and methods thereof to promote immune-mediated destruction of cancer through the intratumoral administration of a CMV-based anti-cancer vaccine.

BACKGROUND OF INVENTION

Cytomegalovirus (CMV) is a member of the beta subclass of the herpesvirus family. It is a large (containing a 230 kilobase genome), double stranded DNA virus that establishes life-long latent or persistent infection. In developed countries such as the United States, approximately 30% to 70% of the population is infected by CMV with variations dependent on age and socioeconomic factors. In contrast to gamma herpesviruses such as Epstein-Barr Virus and Kaposi's Sarcoma-associated Herpesvirus, CMV is non-transforming and non-oncogenic. A live, attenuated CMV vaccine (based on the human CMV Towne strain, which lacks a portion of the CMV genome) has been administered by subcutaneous injection to over 800 subjects in a phase II and III safety and efficacy trials (Arvin et al., Clin. Infect. Dis. 39:233-239, 2004). While this vaccine was found to be completely safe, it was not completely efficacious. More recently, in an attempt to increase its efficacy, some of the missing genes in the Towne-based vaccine strain were replaced. This vaccine has been tested in phase II safety studies, and was found to be safe (Arvin et al., Clin. Infect. Dis. 39:233-239, 2004).

The ability of live, recombinant CMV to generate immune responses against recombinant antigens has been demonstrated in several reports (Hansen et al., Nat. Med. 15:293-299, 2009; Karrer et al., J. Virol. 78:2255-2264, 2004). Moreover, it has recently been demonstrated that a recombinant, replication-competent CMV that is engineered to express a self protein will generate long-lasting, CD8$^+$ T cell-based immunity against cells expressing the self protein (Lloyd et al., Biol. Reprod. 68:2024-2032, 2003). Since most tumor antigens are over-expressed, or mutated self proteins, this result provides support for the concept of using a CMV vector to induce an immune response to tumors.

Most notably, Hanson et al. used recombinant rhesus CMV expressing SIV antigens to immunize rhesus macaques against SIV (Hansen et al., Nat. Med. 15:293-299, 2009). The immunization induced large numbers of activated "effector memory" CD8$^+$ T cells specific for SIV in peripheral tissues, which persisted for the entire multi-year duration of the study. Significantly, the immunized monkeys were substantially protected from SIV challenge, which was attributed to the presence of activated effector-memory T cells. The study also demonstrated that pre-existing immunity to CMV did not prevent the ability of recombinant CMV to induce a new immune response.

Despite the apparent safety of live, attenuated CMV vaccines, significant concerns remain with live CMV-based vaccine strategies. Although in healthy individuals CMV infection is usually completely asymptomatic, problems can arise in immunosuppressed individuals, such as AIDS patients, organ transplant recipients, or infants who were infected in utero. Moreover, potential recipients of a CMV-based tumor vaccine may be or become immunodeficient, significantly limiting the utility of a live CMV tumor vaccine. Thus, a continuing need exists for CMV vaccine vector that would be completely safe in immunocompromised individuals.

Despite substantial efforts over many years, vaccines that elicit effective anti-tumor immunity are rare[1]. Much of the failure of these treatments comes from tumor immune evasion due to features of the tumor micro-environment[2] and tumor-specific T cells becoming dysfunctional or even failing to migrate into the tumor[3,4]. Nevertheless, the presence of spontaneously generated tumor-reactive T cells correlates with improved prognosis in cancer patients[5] suggesting that tumor-specific T cells can effectively delay tumor growth given the right conditions. Thus, recent work has explored therapies that modulate the tumor environment directly[6,7].

Many viruses have been explored for their ability to cause tumor cell destruction and provide "danger" signals within the tumor environment, leading to some pre-clinical and recent clinical successes. The most developed of these so-called oncolytic viruses are based on herpes simplex virus, adenovirus, vaccinia virus, measles virus and reovirus[8], with the herpes simplex platform (T-VEC) recently completing a phase III clinical trial (NCT00769704), in which a 26% objective response rate and 16% durable response rate were reported in stage IIIb, IIIc, and IV melanoma patients[9,10]. T-VEC has been recently approved by the FDA (fda.gov/NewsEvents/Newsroom/PressAnnouncements/ucm469571.htm). Each of these oncolytic viruses was designed to replicate rapidly in tumor cells and directly induce tumor lysis with the hope that this would liberate tumor antigens in an inflammatory (i.e. immune stimulatory) environment. Notably, anti-viral immunity directed against the oncolytic virus can terminate the therapy by clearing the virus, and this is a major limitation for treatment[12]. Therefore, viruses that simulate strong immune responses against the tumor but are difficult to clear may be ideal.

CMV is a β-herpesvirus that establishes an asymptomatic, but life-long infection, leading to exceptionally large humoral and cellular immune responses. Recent interest in developing a CMV-based vaccine has arisen from its ability to induce enormous populations of CD8$^+$ T cells specific for virally-encoded epitopes, better known as memory inflation[13-21]. CMV can be manipulated to express genes of interest[22-24] and such CMV-based vectors have been profoundly protective in a non-human primate model of HIV infection[25,26]. Most people in the world are infected with CMV; however, previous CMV infection does not preclude re-infection, and as a result, CMV-infected monkeys (and presumably people) can be vaccinated and boosted several times with CMV[27,28]. Moreover, CMV-specific CD8$^+$ T cells do not show evidence of exhaustion in immune competent people[29] and are able to migrate into almost any tissue in the body[30,31]. Thus, CMV-based vaccines are in development for clinical trials.

Certain publications address some aspects of administration of adenoviruses. For example, US Pub. No. 2014/

0377294, US Pub. No. 2013/0136768, US Pub. No. 2011/0104101, US Pub. No. 2009/0297555, U.S. Pat. Nos. 8,012,490, and 6,884,414.

However, the prior art fails to describe a CMV-based vaccine that is replication-deficient CMV and capable of generating a robust, long-lasting anti-tumor immune response. In addition, the prior art fails to describe the potential benefits gained by using the intratumoral route to administer a CMV-based vaccine.

SUMMARY OF INVENTION

Embodiments of the present disclosure are related to an intra-lesional administration of a CMV-based vaccine that promotes immune-mediated destruction of cancer through a onetime or repeated intratumoral administration of a recombinant CMV to generate a robust, long-lasting anti-tumor immune response. The present invention provides a therapeutic cancer vaccine that will alter the tumor micro-environment through infection of tumor cells, tumor infiltrating immune cells including macrophages and dendritic cells, tumor stromal cells such as tumor-associated fibroblasts and/or surrounding tissue, may directly kill tumor cells, can enhance pre-existing immunity, can alleviate suppressive mechanisms operating in the tumor environment and can promote immunity against cancer antigens to which a person which did not spontaneously make immunity.

Using CMV vaccine vectors provides the ability to overcome self-tolerance and to establish asymptomatic latency in a subject. Importantly, viral latency allows for repeated stimulation of an anti-tumor immune response.

CMV induces strong CD8[+] T cell responses in humans, where T cells accumulate overtime, are not exhausted, and can migrate into most tissues, making CMV an attractive cancer vaccine platform. Accordingly, the embodiments described herein identify the ability of murine-CMV (MCMV), expressing a modified gp100 melanoma antigen, to induce anti-tumor immune responses.

Vaccination with murine CMV (MCMV) expressing prostate-specific antigen (PSA) was able to delay tumor growth and increase survival in a Tramp-PSA model[32]. In addition, MCMV expressing the tyrosinase-related protein 2 (TRP-2), a common melanoma antigen, induced antibodies that provided prophylactic protection and therapeutic delay in the B16 melanoma model[33]. Lastly, systemic infection with MCMV expressing an altered gp100 peptide induced the accumulation of gp100-specific CD8[+] T cells in the periphery and reduced the growth of B16F10 cells in the lungs of mice in both prophylactic and therapeutic settings, likely in a T cell dependent manner[34].

In a preferred embodiment, an MCMV viral vector encoding an altered version of the melanoma peptide gp100 (gp100$^{S27P}$) was generated in order to stimulate gp100-specific responses. Presentation of this altered peptide induces a potent cytotoxic T lymphocyte (CTL) response that can cross-react with the native-gp100 antigen[35]. This MCMV-gp100 vaccine induced robust expansion of gp100-specific CD8[+] T cells, which migrated into subcutaneously implanted B16F0 tumors, but had little therapeutic efficacy after intraperitoneal (IP) vaccination with or without intradermal (ID) vaccination.

Remarkably however, the experiments described herein show that direct intratumoral (IT) infection of well-established tumor nodules with MCMV was markedly more effective than these previous vaccination routes. Moreover, therapeutic efficacy was not abrogated by previous MCMV infection and was achieved even with wild-type MCMV not encoding the gp100 epitope from melanoma. Depletion of CD8[+] T cells from the animals abrogated the therapeutic benefit of IT MCMV therapy, demonstrating the necessity of anti-tumor T cells in controlling tumor growth. Moreover, MCMV IT infection synergized with the blockade of the PD-1/PD-L1 inhibitory pathway to induce primary tumor clearance and long-term protection independent of the presence of gp100. These data show that systemic vaccination with MCMV-gp100 is ineffective for subcutaneous lesions, but that IT MCMV infection, either with or without recombinant tumor antigens acts to promote anti-tumor immunity and can synergize with immune checkpoint blockades.

It was clear that MCMV could infect and kill multiple tumor cell types in vitro, including melanomas (B16F0, YUMM1.7), colon adenocarcinoma cells (MC38), and prostate cancer cells (TRAMP-C2). Infection of these cells also induced an increase in proteins that promote immune responses such as B7 and MHC. However, analysis of the cells in the tumor environment that were infected revealed that the vast majority of infected cells in the tumor were tumor-associated hematopoietic cells that are likely tumor-associated macrophages. These data, combined with the necessity for CD8+ T cells in controlling tumor growth after IT MCMV therapy, suggest that MCMV was not causing direct destruction of most tumor cells. Rather, IT MCMV therapy was modulating the tumor microenvironment to promote more productive anti-tumor immune responses, independently of whether the tumor antigen gp100 was encoded in the viral genome.

Therefore immune responses are remarkably more effective if the vaccine is delivered intra-lesionally (i.e., directly into an established tumor mass). This route of vaccination appears to promote more functional T cells that control tumor growth when compared to alternate routes of vaccination (e.g., intraperitoneal (ip) or intravenous (iv) administration).

A preferred embodiment is directed towards a CMV based vaccine comprising a carrier suitable for injection into a human patient.

A CMV-based vaccine that promotes immune-mediated destruction of cancer through intratumoral administration of a recombinant CMV to generate a robust, long-lasting anti-tumor immune response comprising a plurality of CMV virus cells, and a pharmaceutically acceptable carrier. In certain embodiments, the CMV is an attenuated-CMV.

A method of generating an anti-tumor immune response in a patient comprising administering to said patient a human-CMV (HCMV), expressing tumor antigens to said patient. In preferred embodiments, the CMV-based vaccine is administered intra-tumorally to a patient.

A method of treating a tumor by direct intra-lesional injection of CMV, wherein the intra-lesional injection enhances the pre-existing immune responses by modulating the tumor micro-environment, possibly through infection of tumor-associated macrophages or other cells in the tumor environment, or through the activation of signaling cascades in response to the presence of the virus in the tumor, directly promoting tumor cell destruction by infecting the tumor cells, and generating new or boosted immune responses against the antigens encoded within the viral genome. In certain embodiments, the CMV encoding for a tumor antigen within the viral genome. In further embodiments, the CMV is selected from the group consisting of attenuated, live, virulent, spread defective, replication-incompetent, killed, or combinations thereof. Wherein a killed CMV is utilized, the killed CMV encoding tumor antigens within the viral genome; and may be produced by UV irradiation, or chemical inactivation.

In certain embodiments, the tumor is specifically treated by direct intra-lesional injection of CMV is selected from the group consisting of live, virulent, attenuated, spread-defective, replication incompetent, killed CMV, or combinations thereof, that is otherwise free of tumor antigens.

A method of treating a tumor by direct intra-lesional injection of live, spread-defective CMV encoding tumor antigens within the viral genome, wherein the spread-defective CMV may be generated by deletion of an essential glycoprotein such as gB, gH, gL or any other protein that controls viral entry into cells or assembly of infectious viral particles.

A method of treating a tumor by direct intra-lesional injection of live, virulent, attenuated, spread-defective, replication incompetent or killed CMV that either expresses or lacks tumor antigens encoded within its genome and to combine this therapy with alternative routes of vaccination (e.g. intravenous, subcutaneous, intramuscular, oral or intranasal).

A method of treating cancer comprising administering to a patient having cancer, a CMV-based intratumoral injection.

A method of destroying cancerous cells and promoting anti-tumor immune response comprising administering to a patient having cancerous cells, a CMV-based intratumoral injection.

In certain embodiments and methods described above, the method comprises a onetime or repeated intra-lesional injections is suitable depending on the necessary response and the stability of the patient. In particular, wherein the injection is systemic and performed with a single, or repeated administration of the vaccine. In certain administration protocols, a method comprises two injections, a first injection comprises an intra-lesional injection and the second injection is a systemic injection.

In the described methods, a particular embodiment is directed towards a therapeutic wherein the CMV virus for therapeutic use retains the pentameric complex consisting of the glycoproteins H and L (gH and gL), along with UL128, UL130 and UL131.

In the described methods, the therapeutic is given in combination with an anti-PD-L1 therapeutic. In certain embodiments, the anti-PD-L1 therapeutic increases the function of circulating and tumor-localized CD8$^+$ T cells in the patient, or wherein the therapeutic infects tumor associated macrophages, or wherein the therapeutic is combined with an immune checkpoint inhibitor, or wherein the therapeutic is combined with an immune stimulating therapy. These therapeutics may be combined with additional tumor therapeutic that may promote tumor cell destruction and/or tumor growth delay.

A CMV-based composition comprising: CMV viruses, wherein the CMV is selected from the group consisting of a live, virulent, attenuated, spread-defective, replication incompetent, killed CMV, or combinations thereof that is otherwise free of tumor antigens, a pharmaceutically acceptable carrier, and an immunotherapeutic that blocks the PD-1/PD-L1 pathway.

A CMV composition or the methods described herein can be concomitantly administered with or without systemic vaccination, and an additional immunotherapies, chemotherapies, radiation therapies or other therapies that would be used to promote improved anti-tumor immune responses or tumor cell destruction, wherein said therapies target PD-1, PD-L1, CTLA-4, B7-H3, LAG-3, TIM-3, TIGIT, IDO, OX40, CD27, CD40, and/or CD40L, or an immune modulating therapy, or combinations thereof.

A method of treating a tumor by direct intra-lesional injection of CMV encoding tumor antigens within the viral genome, wherein the intra-lesional injection enhances the pre-existing immune responses by modulating the tumor micro-environment, possibly through infection of tumor-associated macrophages or other cells in the tumor environment, or through the activation of signaling cascades in response to the presence of the virus in the tumor, directly promoting tumor cell destruction by infecting the tumor cells, and generating new or boosted immune responses against the antigens encoded within the viral genome.

A further preferred embodiment is directed to a method of treating a tumor by direct intra-lesional injection of live, attenuated CMV encoding tumor antigens within the viral genome. Tumor antigens can include antigens that are derived from the cellular genome such as mutations, or improperly expressed proteins, or derived from viruses that have induced the tumor. Without being limited to the particular mechanism of action, this is expected to enhance the pre-existing immune responses by modulating the tumor micro-environment, possibly through infection of tumor-associated macrophages or other cells in the tumor environment, or through the activation of signaling cascades in response to the presence of the virus in the tumor, directly promote tumor cell destruction by infecting the tumor cells, and generate new or boosted immune responses against the antigens encoded within the viral genome. Such immune responses may be effective against lesions that have metastasized and are growing at a distant site from the site of injection.

An alternative embodiment is to treat the tumor by direct intra-lesional injection of live, virulent CMV encoding tumor antigens within the viral genome. Without being limited to the particular mechanism of action, this is expected to enhance the pre-existing immune responses by modulating the tumor micro-environment, possibly through infection of tumor-associated macrophages or other cells in the tumor environment, or through the activation of signaling cascades in response to the presence of the virus in the tumor, directly promote tumor cell destruction by infecting the tumor cells, and generate new or boosted immune responses against the antigens encoded within the viral genome. Such immune responses may be effective against lesions that have metastasized and are growing at a distant site from the site of injection. However, the virulent CMV may promote more tumor destruction or more potently alter the tumor micro-environment, both of which may be desirable in certain clinical situations.

An alternative embodiment is to treat the tumor by direct intra-lesional injection of live, spread-defective CMV encoding tumor antigens within the viral genome. Spread-defective CMV may be generated by deletion of an essential glycoprotein such as gB, gH, gO, gL or any other protein that controls viral entry into cells or virion assembly. In all cases, recombinant viruses would be produced by complementing the missing viral protein in trans, during production of the vaccine. Without being limited to the particular mechanism of action, this is expected to enhance the pre-existing immune responses by modulating the tumor micro-environment, possibly through infection of tumor-associated macrophages or other cells in the tumor environment, or through the activation of signaling cascades in response to the presence of the virus in the tumor, directly promote tumor cell destruction by infecting the tumor cells, and generate new or boosted immune responses against the antigens encoded within the viral genome. Such immune responses may be effective against lesions that have metastasized and are growing at a distant site from the site of injection. However, the inability of the virus to spread from cell-to-cell after the initial infectious cycle would improve the safety profile of this vaccine.

An alternative embodiment is to treat the tumor by direct intra-lesional injection of live, replication incompetent CMV encoding tumor antigens within the viral genome. Replication incompetent CMVs can be generated by deleting viral genes necessary for replicating the viral genome. As above, recombinant viruses would be produced by complementing the missing viral protein in trans, during production of the vaccine. Without being limited to the particular mechanism of action, this is expected to enhance the pre-existing immune responses by modulating the tumor micro-environment, possibly through infection of tumor-associated macrophages or other cells in the tumor environment, or through the activation of signaling cascades in response to the presence of the virus in the tumor, directly promote tumor cell destruction by infecting the tumor cells, and generate new or boosted immune responses against the antigens encoded within the viral genome. Such immune responses may be effective against lesions that have metastasized and are growing at a distant site from the site of injection. However, the inability of the virus to replicate would improve the safety profile of this vaccine.

An alternative embodiment is to treat the tumor by direct intra-lesional injection of killed CMV encoding tumor antigens within the viral genome. Killed CMV may be produced by UV irradiation, or chemical inactivation. Without being limited to the particular mechanism of action, this would be expected to modulate the tumor environment, possibly through infection of tumor-associated macrophages or other cells in the tumor environment, or through the activation of signaling cascades in response to the presence of the virus in the tumor, and generate new or boosted anti-tumor immune responses to enhance the pre-existing immune responses by modulating the tumor micro-environment and generate new or boosted immune responses against the antigens encoded within the viral genome. Such immune responses may be effective against lesions that have metastasized and are growing at a distant site from the site of injection, but would not infect and directly kill tumor cells. However, the absence of infectious particles would improve the safety profile of this vaccine.

An alternative embodiment is to treat the tumor by direct intra-lesional injection of live, virulent, attenuated, spread-defective, replication incompetent or killed CMV that is otherwise free of tumor antigens. Without being limited to the particular mechanism of action, this would be expected to have the effects described in prior embodiments, but would not be expected to directly generate new or boosted immune responses to tumor antigens since none are encoded within the viral genome. However, the use of CMV-based vaccines that lack described tumor antigens would make these vaccines generally applicable to any tumor type with accessible lesions—regardless of whether tumor-associated antigens have been defined. The results described herein clearly show that wild-type CMV will work to promote tumor growth delay and clearance, regardless of whether the viral backbone encodes tumor-associated antigens.

An alternative embodiment is to treat the tumor by direct intra-lesional injection of live, virulent, attenuated, spread-defective, replication incompetent or killed CMV that either expresses or lacks tumor antigens encoded within its genome and to combine this therapy with alternative routes of vaccination (e.g. intravenous, subcutaneous, intramuscular, oral or intranasal). The vaccine delivered by alternate route may also be live virulent, attenuated, spread-defective, replication incompetent or killed, and would encode tumor antigens within the viral genome to promote systemic anti-tumor immunity.

In each of the embodiments described above, a onetime or repeated intra-lesional injections is suitable depending on the necessary response and the stability of the patient. Likewise, the systemic vaccination described in paragraph 00026 could be performed with a single, or repeated administration of the vaccine.

In each of the embodiments described above, the use of a strain of CMV that preferentially targets monocytes and macrophages for infection is preferred due to the preference of the virus for infecting tumor-associated macrophages in the preclinical model. For this reason, the preferred virus for therapeutic use will retain the so-called "pentameric complex" consisting of the glycoproteins H and L (gH and gL), along with UL128, UL130 and UL131. This might exclude some of the previously tested laboratory adapted strains of CMV that have lost one or more of these important genes. The infection of tumor-associated macrophages and other tumor-associated cells of the hematopoietic system may be critical for the CMV therapy to modulate the tumor environment and promote anti-tumor immune responses.

An alternative embodiment would be to use a strain of CMV that preferentially targets other tumor-associated cells, the tumor cells directly, or tumor stroma, depending on the tumor type and its dependence on tumor-associated macrophages for growth. This may have the additional advantage of increasing the safety profile of the therapy, and could conceivably be combined with a vaccine that retains macrophage infectivity.

The methods described herein provide for a CMV-based intratumoral injections that markedly synergizes with immunotherapies such as antibodies that block the PD-1/PD-L1 pathway. Thus, in all of the embodiments described above, the IT therapy of a virus that contains or lacks expression of tumor-associated antigens, with or without systemic vaccination, may synergize with additional immunotherapies, chemotherapies, radiation therapies or other therapies that would be used to promote improved anti-tumor immune responses or tumor cell destruction.

The methods described herein provide evidence that therapies blocking immune checkpoints may particularly synergize with intratumoral CMV vaccines. These therapies block the "off" signal received by certain cell, thereby ensuring that T-cells function in the cell. The most well-known immune checkpoint blockades target the inhibitory molecules PD-1 (or its ligand PD-L1) and CTLA-4. As antibodies and other molecules targeting PD-1, PD-L1 and CTLA-4 are currently approved for several cancers, a preferred embodiment would be to combine CMV-based vaccines in any of the embodiments described above, with agents that block PD-1 (including but not limited to Nivolumab/BMS-936558/MDX1106, pidilizumab/CT-011, pembrolizumab/MK-3475, and/or AMP-224), PD-L1 (including, but not limited to BMS-936559/MDX-1105, MEDI4736, MPDL3280A/RG7446 and/or MSB0010718C) and/or CTLA-4 (including, but not limited to Ipilimumab and/or Tremelimumab). Additional immune checkpoint inhibitors currently in clinical trials include antibodies and molecules that target B7H3, LAG3, TIM3, TIGIT and IDO and any of these, along with new therapies that target immune suppressive pathways or immune checkpoints, would be a preferred embodiment.

An alternative embodiment would be to combine the CMV vaccine with immune therapies that promote immune responses such as antibodies that target immune co-stimulators OX40, CD27, CD40 and CD40L. These antibodies, by contrast enhance the response, instead of preventing the block as with the prior compounds. Alternatively, both a blocking and promoting therapeutic can be provided in combination with the CMV based vaccine.

DETAILED DESCRIPTION OF THE FIGURES

Figure 1A:
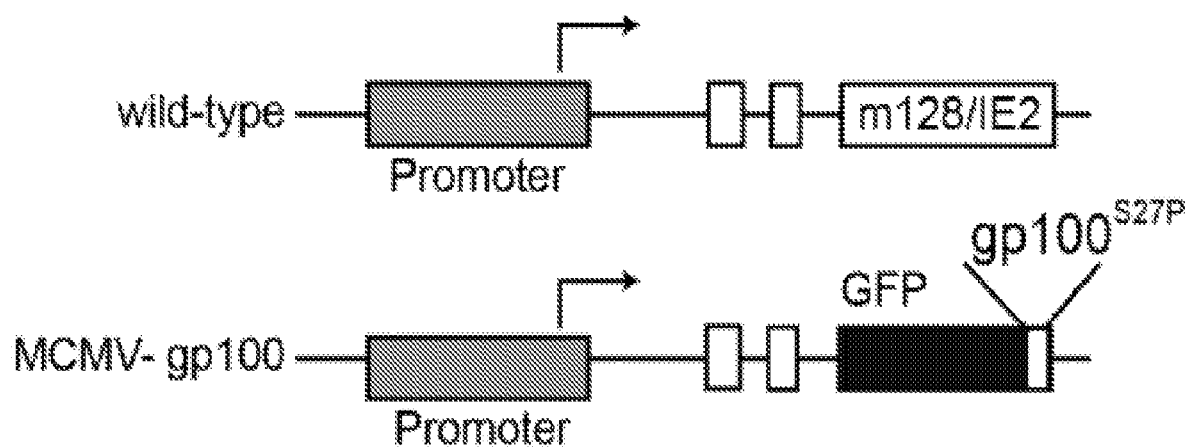
FIGS. 1 A-D depicts the construction and characterization of MCMV-gfp-gp100.

In previous work, vaccination with murine CMV (MCMV) expressing prostate-specific antigen (PSA) was able to delay tumor growth and increase survival in a Tramp-PSA model[32]. In addition, MCMV expressing the tyrosinase-related protein 2 (TRP-2), a common melanoma antigen, induced antibodies that provided prophylactic protection and therapeutic delay in the B16 melanoma model[33]. Lastly, systemic infection with MCMV expressing an altered gp100 peptide induced the accumulation of gp100-specific CD8+ T cells in the periphery and reduced the growth of B16F10 cells in the lungs of mice in both prophylactic and therapeutic settings, likely in a T cell dependent manner[34]. Together, these data show that systemic immune responses elicited by CMV-based vaccines can be effective against some types of tumors or tumors growing in some locations.

The embodiments described herein demonstrate that therapeutic vaccination by the intraperitoneal (IP) and intradermal (ID) routes induced tumor infiltrating gp100-specific CD8+ T cells, but provided minimal therapeutic benefit for subcutaneous melanoma lesions. In contrast, intratumoral (IT) infection of established tumor nodules with MCMV greatly inhibited tumor growth and substantially improved overall survival, even in mice previously infected with MCMV. Thus, our data clearly show that the immune responses elicited by an MCMV-based vaccine are remarkably more effective if the vaccine is delivered intra-lesionally (i.e., directly into an established tumor mass). This route of vaccination may promote more functional T cells that control tumor growth when compared to alternate routes of vaccination. Moreover, this route of vaccination may enable efficient infection of tumor-associated macrophages.

Surprisingly, the presence of a tumor antigen in the virus did not increase the efficacy of IT infection alone in the single tumor model used in our experiments. In vitro, MCMV could infect and kill B16F0s, indicating that MCMV could be killing tumor cells directly. However, in vivo, most of the infected cells were tumor-associated macrophages suggesting that direct destruction of tumor cells was not the dominant mechanism preventing tumor growth. In addition, depletion of CD8+ T cells abrogated the therapeutic effect of IT MCMV therapy, demonstrating a need for CD8+ T cells for the success of the therapy. Thus, IT MCMV infection may alter the tumor microenvironment, either through infection of macrophages or other tumor-associated cells, or through the activation of immune enhancing signaling cascades, to improve anti-tumor immunity.

After IT therapy, tumor-specific CD8+ T cells in the tumor were dysfunctional, correlating with PD-1$^{hi}$ expression. Importantly, combining IT MCMV infection with anti-PD-L1 therapy was synergistic, resulting in tumor clearance from over half of the mice and subsequent protection against tumor challenge. PD-L1 blocking antibodies are known to improve anti-tumor T cell responses and the synergy between the two therapies was achieved regardless of whether the virus encoded a tumor antigen. Indeed, the PD-L1 and similar checkpoint inhibitors prevents the inhibition of the T-cells in the body. Essentially, the blockade strategy either prevents the generation of signaling compounds, or prevents the binding of the compounds on the T-Cells, to prevent the down regulation or "off" signal to the T-cells.

By contrast, OX40, CD27, and CD40L are on the T-cell and enhance or promote the immune response. Similarly, CD40 works in a similar manner through separate pathways to enhance T-cell function.

Either a blocking strategy or an enhancement strategy may be suitable to be combined with the CMV vaccine in a concomitant therapeutic so as to treat cancers, as described herein.

Thus, while an MCMV-based vaccine administered systemically, was poorly effective against established subcutaneous tumors, direct infection of tumor nodules unexpectedly delayed tumor growth and synergized with immune checkpoint blockades to promote tumor clearance and long-term protection. These data indicate that viral modulation of the tumor environment, or destruction of tumor cells after IT therapy was sufficient to enhance pre-existing anti-tumor immunity and improve clearance of the injected tumor. We propose that inclusion of the tumor antigens in the viral genome will improve the therapy beyond the injected tumor by promoting systemic immunity.

FIGS. 1 A-C depicts the construction and characterization of mcmv-gfp-gp100 A) Schematic of recombinant strain MCMV-GFP-gp100$^{S27P}$ (MCMV-gp100) in which the altered gp100 peptide was fused to EGFP and cloned into the IE2 region of the MCMV genome. B) The growth of MCMV-gp100 vs. WT-MCMV in M2-10B4s. Data represent pooled results from two independent experiments and show the mean+/−the SD. C) Representative FACS plots of CD8+ T cell cytokine production after stimulation with the indicated peptides ex vivo. T cells were obtained from the peripheral blood on day 104 post-infection with either MCMV-gp100 or WT-MCMV. D) CD8+ T cell responses to the indicated peptides over time, assessed as in "C". Data is represented as the mean value+/−SD from a total of 5 animals per group.

FIGS. 2 A-D depicts an intraperitoneal and intradermal infection with MCMV-gp100 which induced poor anti-tumor responses. Animals received 1×10$^5$B16F0s subcutaneously on D0 followed by IP or IP/ID vaccination with MCMV-gp100 or WT-MCMV on D5 post implantation. The data shown is combined from 3 separate experiments. A) Lymphocytes in the tumor (top panel) and spleen (bottom panel) after MCMV-gp100 vaccination. NKs=NK cells, Neutro=Neutrophil, Granu=Granulocyte, Macro=Macrophage, Mono=Monocyte, Treg=T regulatory cell. B) IFN-γ production of CD8+ T cells recovered from tumors at sacrifice and stimulated or not ex vivo with the native gp100 peptide (n=5-9 mice). C) Tumor growth curves showing the growth, by area, of individual tumors from unvaccinated (n=13) MCMV-gp100 IP vaccinated (n=9), WT-MCMV IP/ID vaccinated (n=9), and MCMV-gp100 IP/ID vaccinated mice (n=10). The dotted line indicates the day of vaccination. D) Kaplan-Meier survival curve of treated animals.

FIGS. 3 A-E depicts the MCMV-gp100 infection of B16F0s in vitro, which induced cell death and increased immunogenicity. B16F0s were infected in vitro at the indicated MOI. Shown is the growth of virus after infection of B16F0s or M2-10B4s with low (A) or high (B) MOI, the proportion of B16s that were infected (C), the viability of B16s after infection (D) and the growth of B16s after infection (E) after low or high MOI. Data are representative of at least two independent experiments. Error bars indicate standard deviation from replicate samples (n=2). F) B16F0s were plated at a concentration of 25,000 cells per well and "spinfected" one day later with MCMV-gp100 at an MOI of 10. Infected cells were identified by GFP expression. Shown is the mean fluorescent intensity of MHC-I (H-2D$^b$ and H-2K$^b$), and MHC-II (I-A/I-E), for infected and uninfected B16F0s in the same wells at D1 and D2 post-infection. Dotted lines at each timepoint represent the background MFI of infected B16F0s not stained with the indicated antibody. Data are representative of 2 independent experiments and each done in triplicate.

FIGS. 4 A-F depicts an intratumoral infection of B16F0 tumors with MCMV, which induced tumor growth delay, regression, and improved survival. A) The treatment schedule of MCMV intratumoral infection. All tumors were initially injected at a tumor area of 20 mm$^2$. Each intratumoral infection consisted of 5×10$^5$ pfu. B-D) The data shown is combined from 4 separate experiments. B) Tumor growth, represented as change in tumor area (mm$^2$) over time, is shown from the day of the first intratumoral injection. MCMV-gp100 IP/ID vaccination was given on D5 post tumor implantation followed by PBS IT on the schedule shown in "A". PBS IT (n=6); MCMV-gp100 IP/ID→PBS IT (n=6); WT-MCMV IT (n=18); MCMV-gp100 IT (n=18). Vertical dotted lines represent days of intratumoral injection. C) Kaplan Meier survival curve of the different treatment groups from day of tumor implantation until tumors were above 100 mm$^2$. D) Tumor lymphocyte infiltration at time of sacrifice. NKs=NK cells, Neutro=Neutrophil, Granu=Granulocyte, Macro=Macrophage, Mono=Monocyte, Treg=T regulatory cell. E-F) Mice latently infected with MCMV-K181 for 8 or 52 weeks received B16F0s and were infected following the schedule described in "A" with MCMV-gp100 (n=8 mice infected 8 weeks previously, n=4 mice infected 52 weeks previously) or PBS (n=8 mice). E) Tumor growth from the day of IT infection. F) Kaplan Myer survival curve of different treatment groups. For comparison, data from mice that were naive before tumor implantation is taken from FIG. 4c.

Figure 4A:
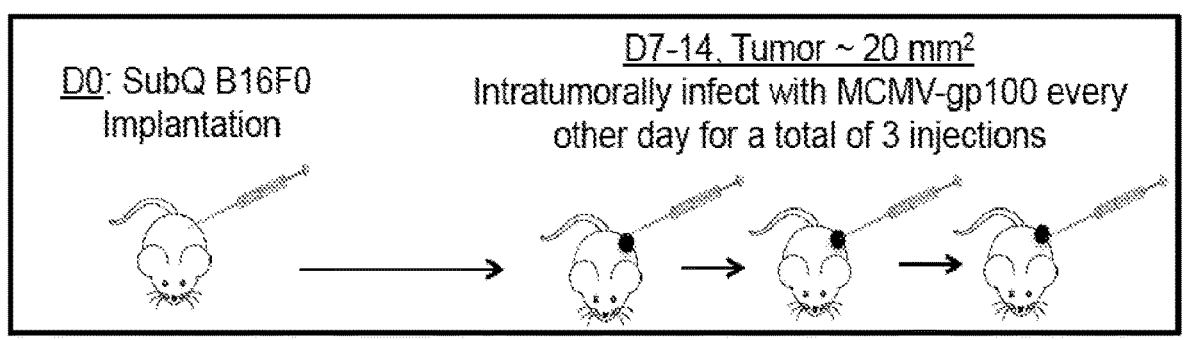
FIGS. 4 A-F depicts an intratumoral infection of B16F0 tumors with MCMV, which induced tumor growth delay, regression, and improved survival.
Figure 4B:
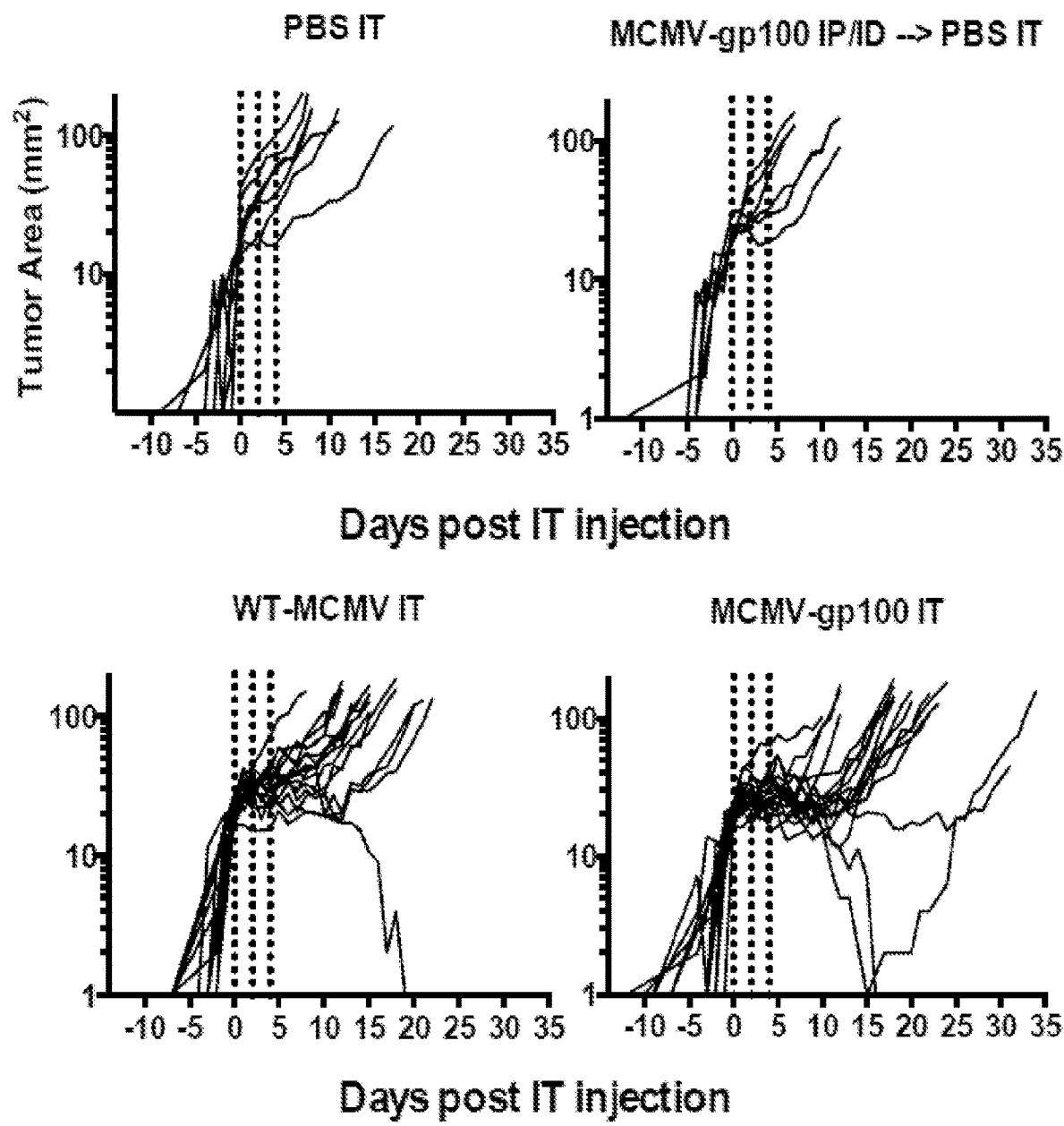
Figure 4C:
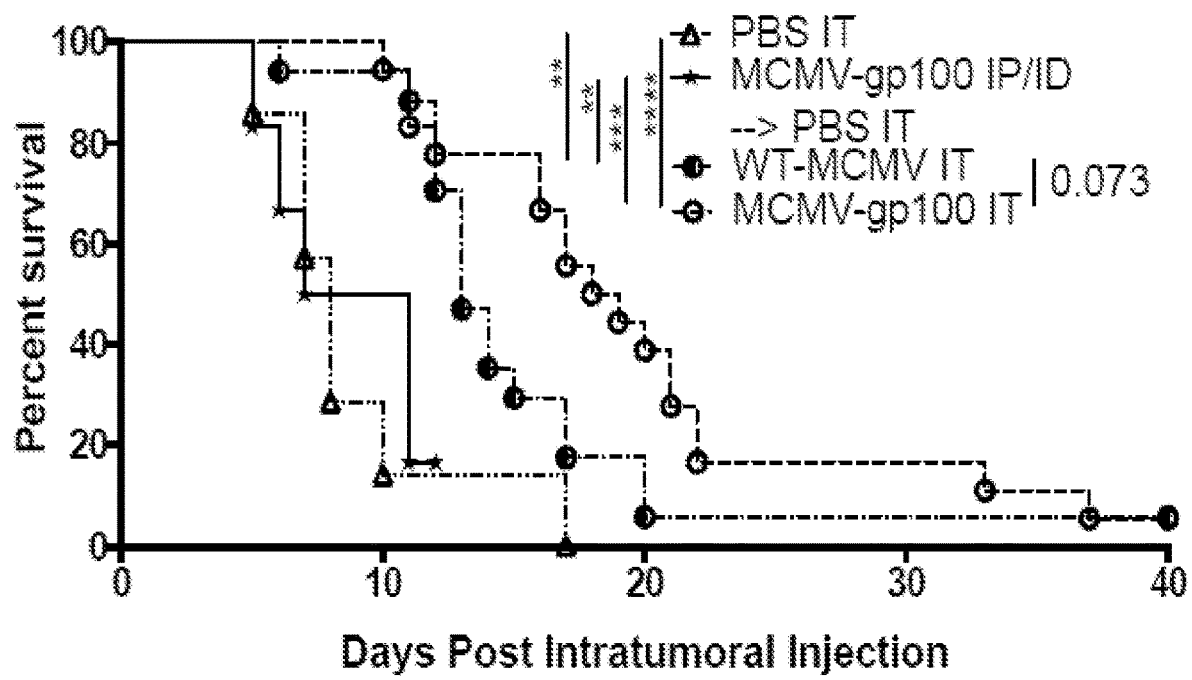
Figure 4D:
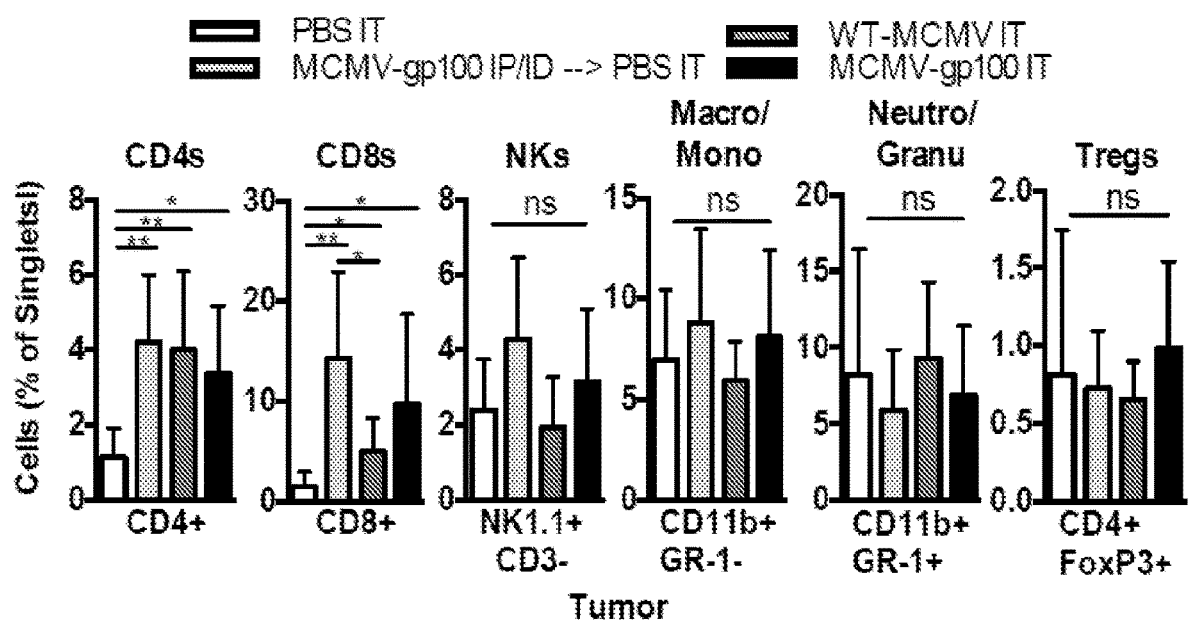
Figure 4E:
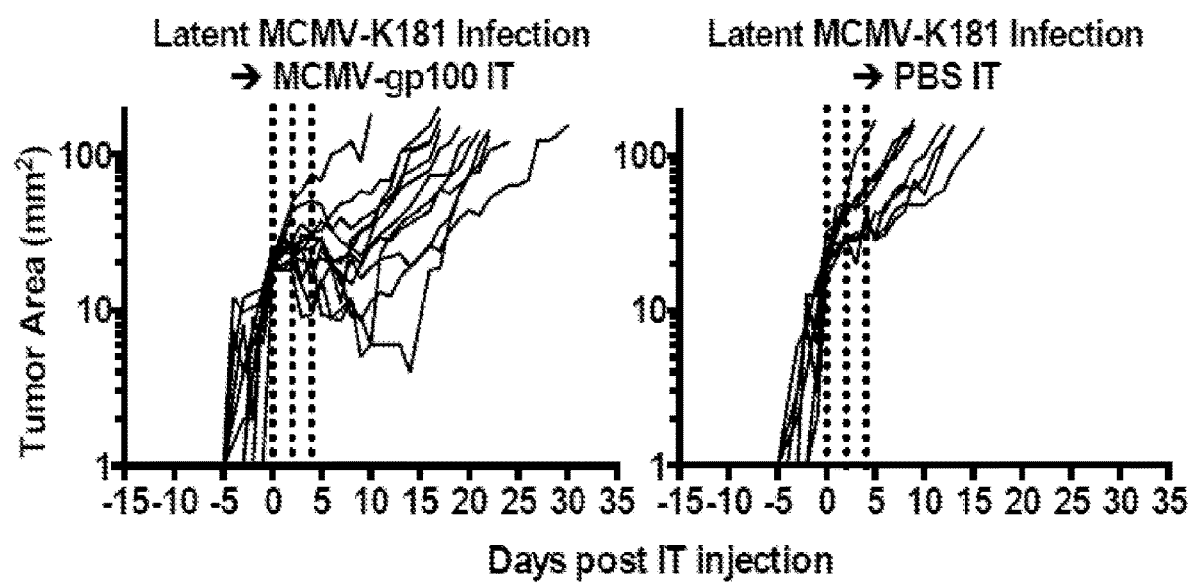
Figure 4F:
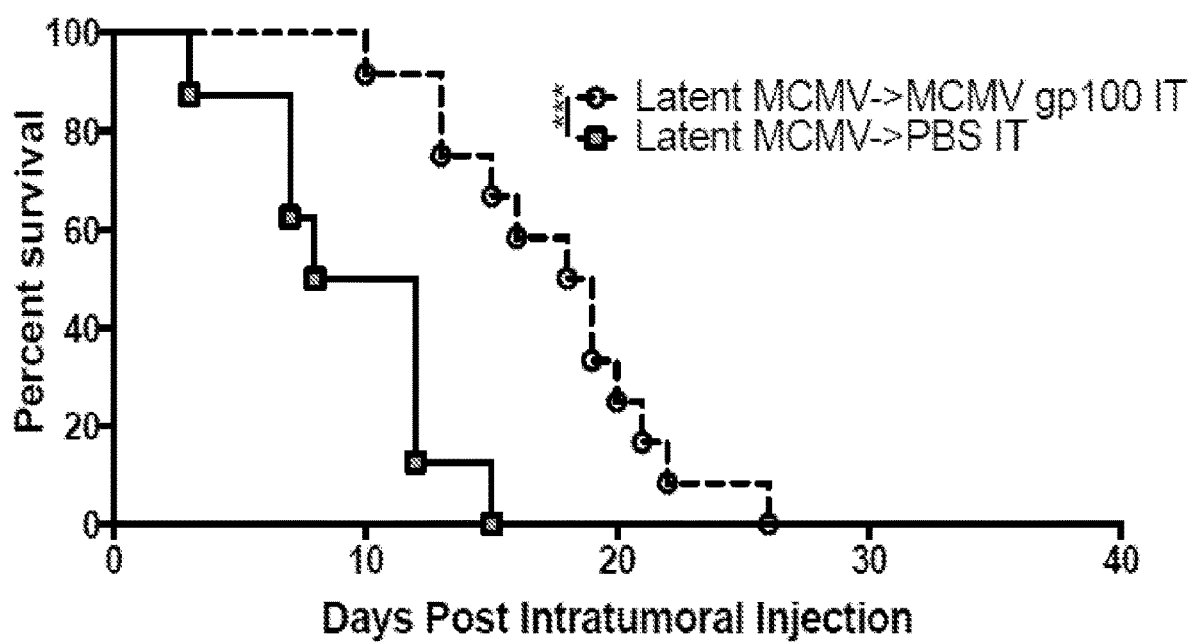
Figure 5A:
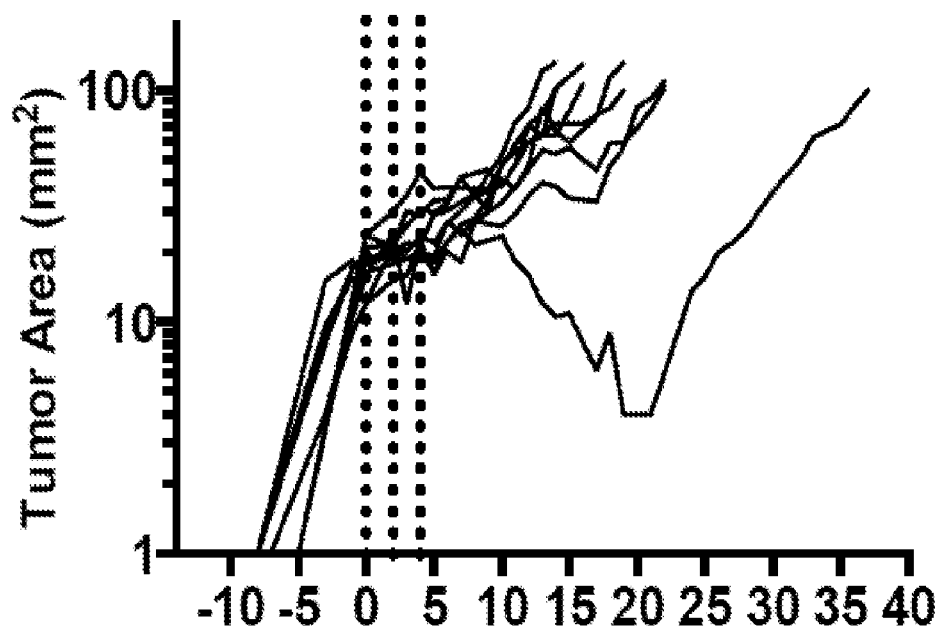
FIGS. 5 A-B depicts intratumoral infection of MC38 colon adenocarcinoma with MCMV.
Figure 5A:
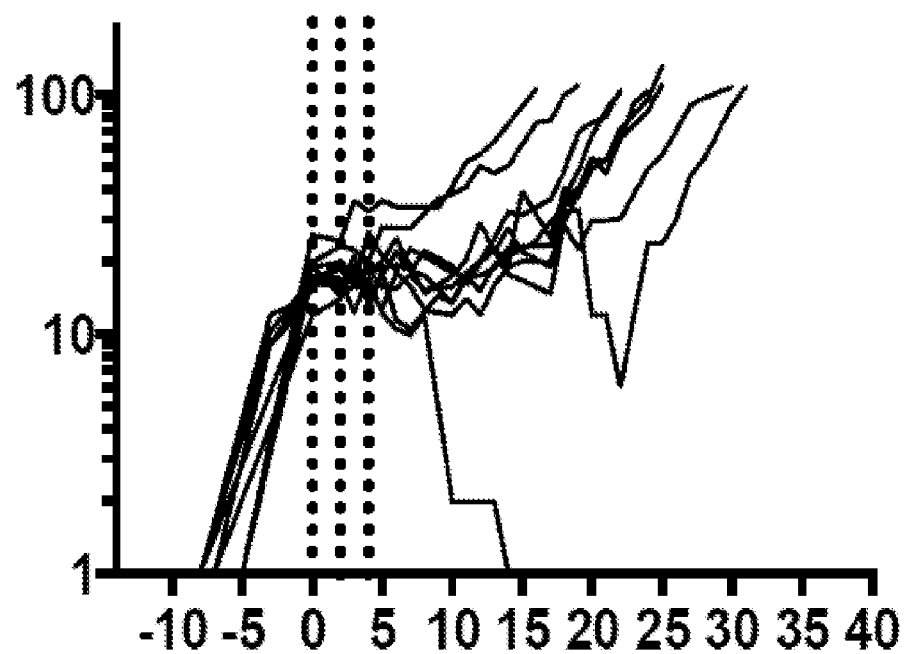
Figure 5B:
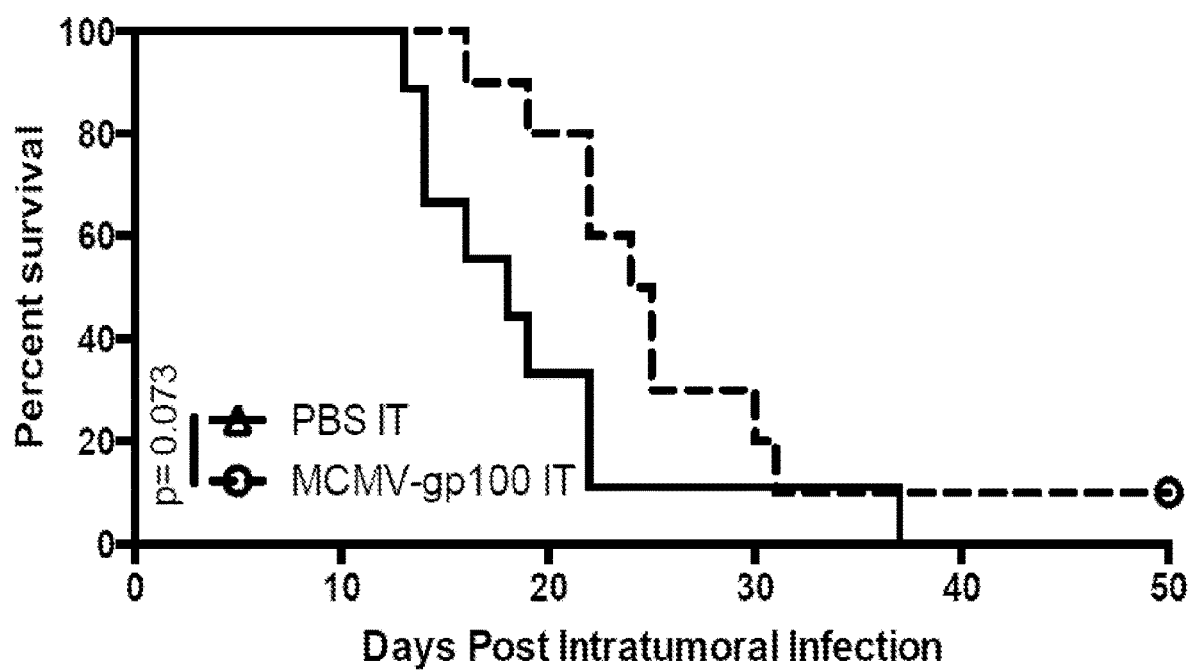

FIGS. 5 A-B depicts intratumoral infection of MC38 colon adenocarcinoma with MCMV. C57BL/6 mice were subcutaneously implanted with 5×10$^5$MC38s and treated with MCMV IT or PBS IT as described in FIG. 4, when tumors were 20 mm$^2$. A) Tumor growth, represented as change in tumor area (mm$_2$) over time, is shown from the day of the first intra-tumoral injection. B) Kaplan Meier survival curve of the MCMV IT versus PBS IT treated animals from day of tumor implantation until tumors were above 100 mm$_2$. Significance was assessed by a logrank test, p<0.05=*.

Figure 6A:
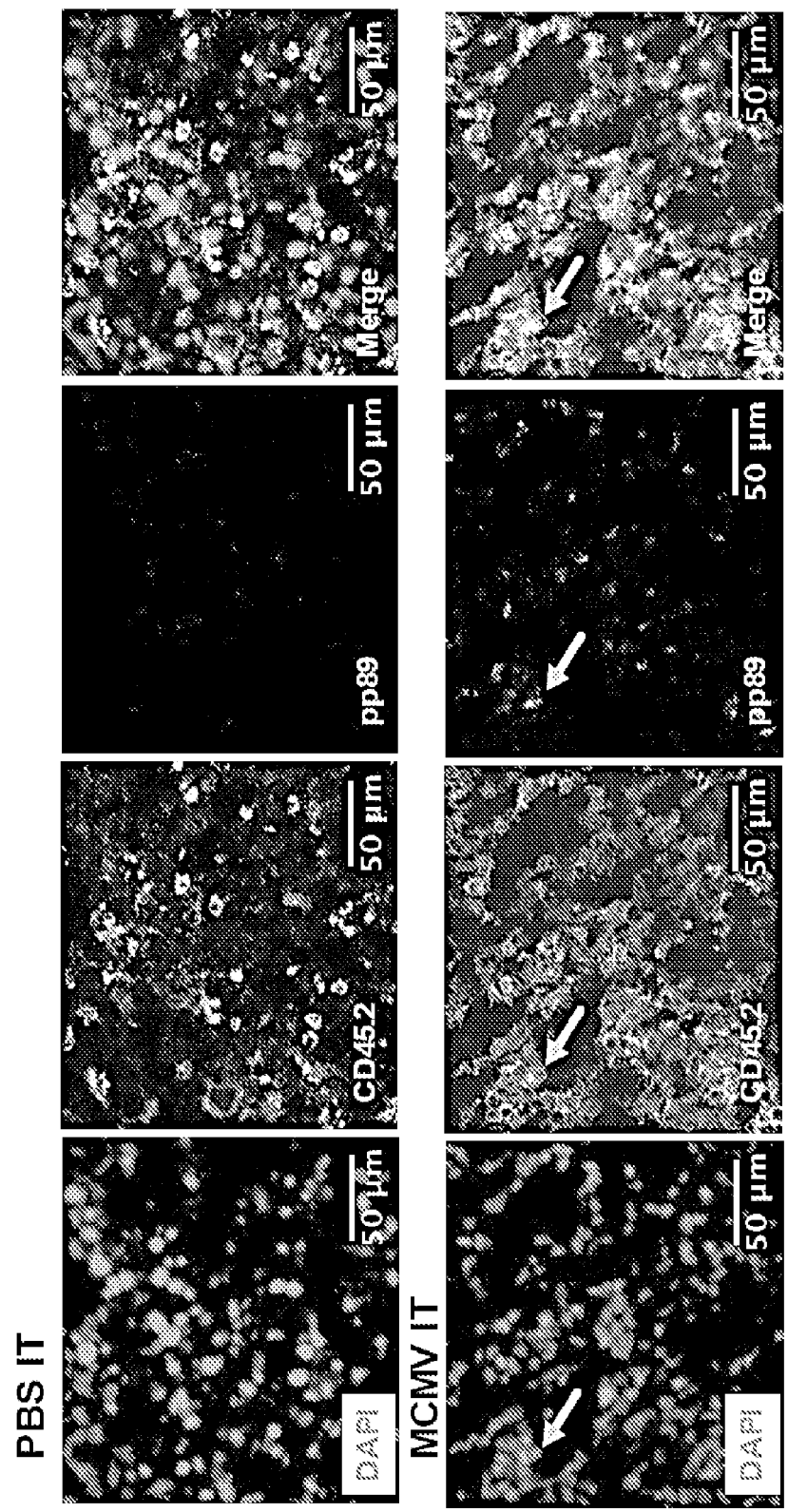
FIGS. 6 A-C depicts the infection of tumor-associated macrophages (TAMS) after IT MCMV therapy.
Figure 6B:
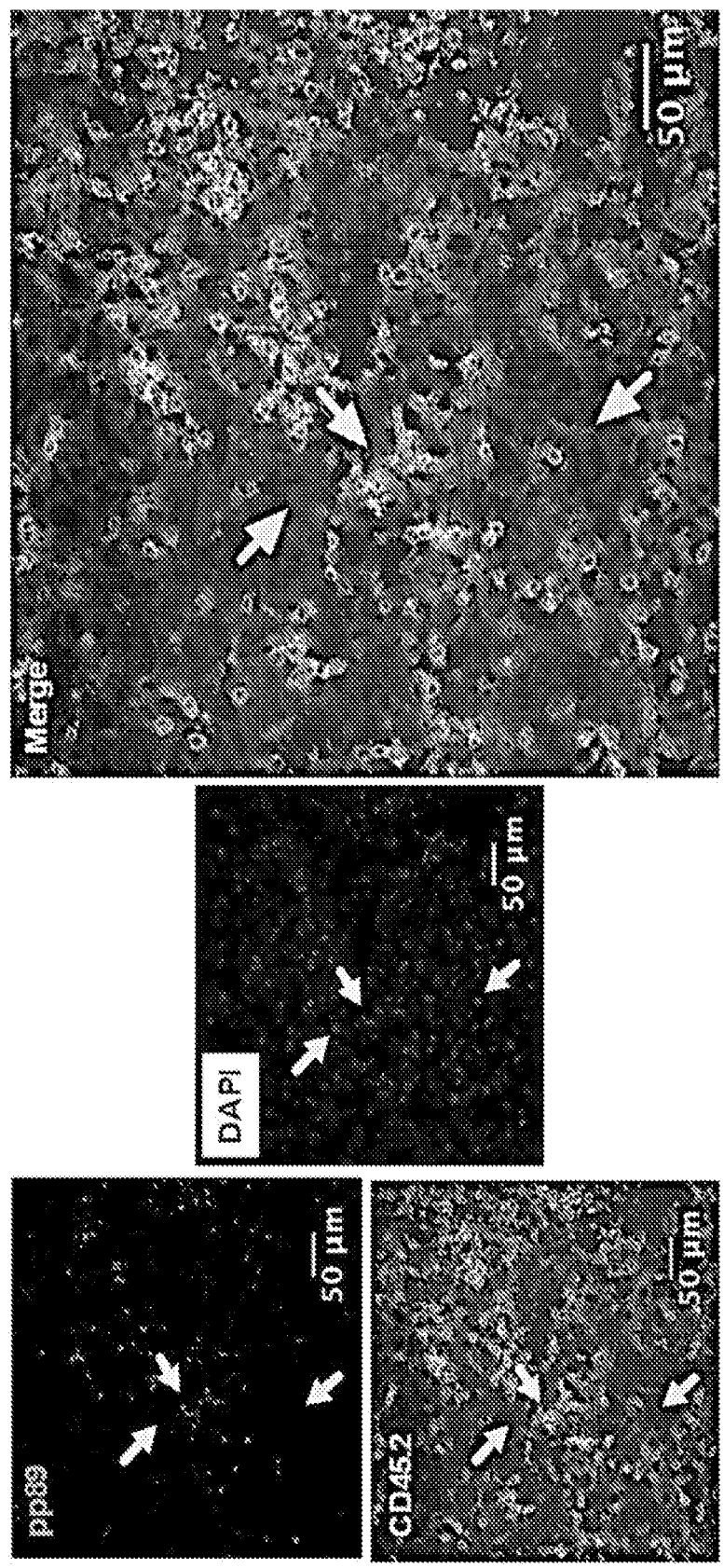

FIGS. 6 A-C: depicts the infection of tumor-associated macrophages (TAMS) after IT MCMV therapy. Mice received IT injections with WT-MCMV or MCMV-gp100 as in FIG. 4. Tumors were harvested 1 day after the last IT injection and processed for histology. Arrows indicate the same cell in each panel for identification of infected or uninfected cells. A and B) Immunofluorescence staining of to define infected cells in tumors IT injected with PBS (control) or MCMV. Tumors were stained for DAPI to define the nucleus, CD45.2 to define hematopoietic cells and viral pp89 to define infected cells. The data shows that most infected cells (pp89-positive) are also hematopoietic cells (CD45.2-positive). In panel A, one infected cell is highlighted in the tumors from infected mice. In panel B, one infected cell (arrow pointing down and to the left) and two uninfected cells (arrows pointing up and to the left or down and to the right) are highlighted. The two highlighted uninfected cells are CD45-negative, and thus, non-hematopoietic cells. C) As in A and B except that tumor sections were stained for pp89 to define infected cells, CD11b to define monocytic cells, and F4/80 to define macrophages, after MCMV IT infection. The data shows that nearly all infected cells were also expressing CD11b and F4/80. Three cells that were positive for all 3 markers are highlighted by the arrows.

Figure 7A:
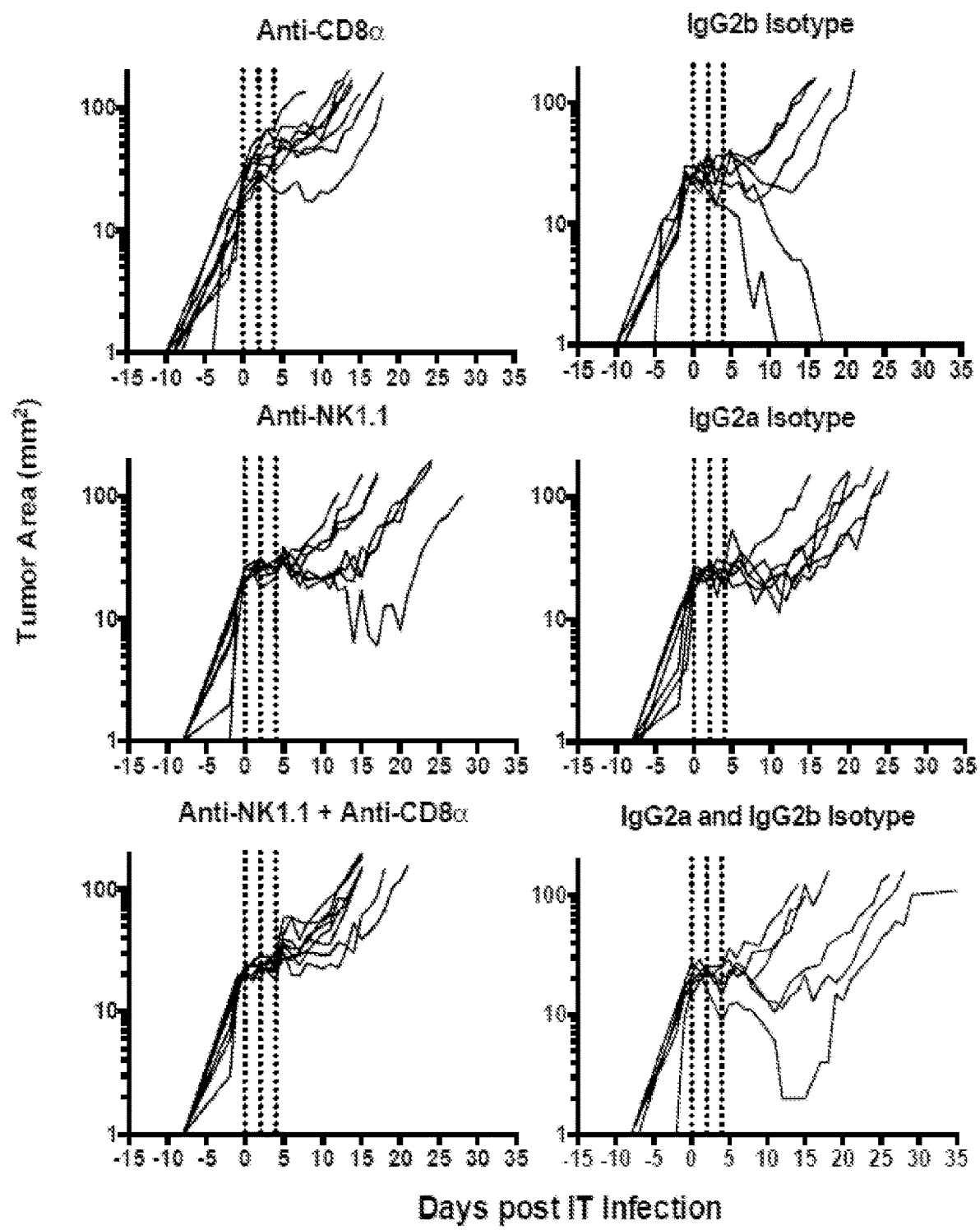
FIGS. 7 A-B depicts the survival benefit after MCMV IT therapy without CD8+ T cells or NK cells.
Figure 7B:
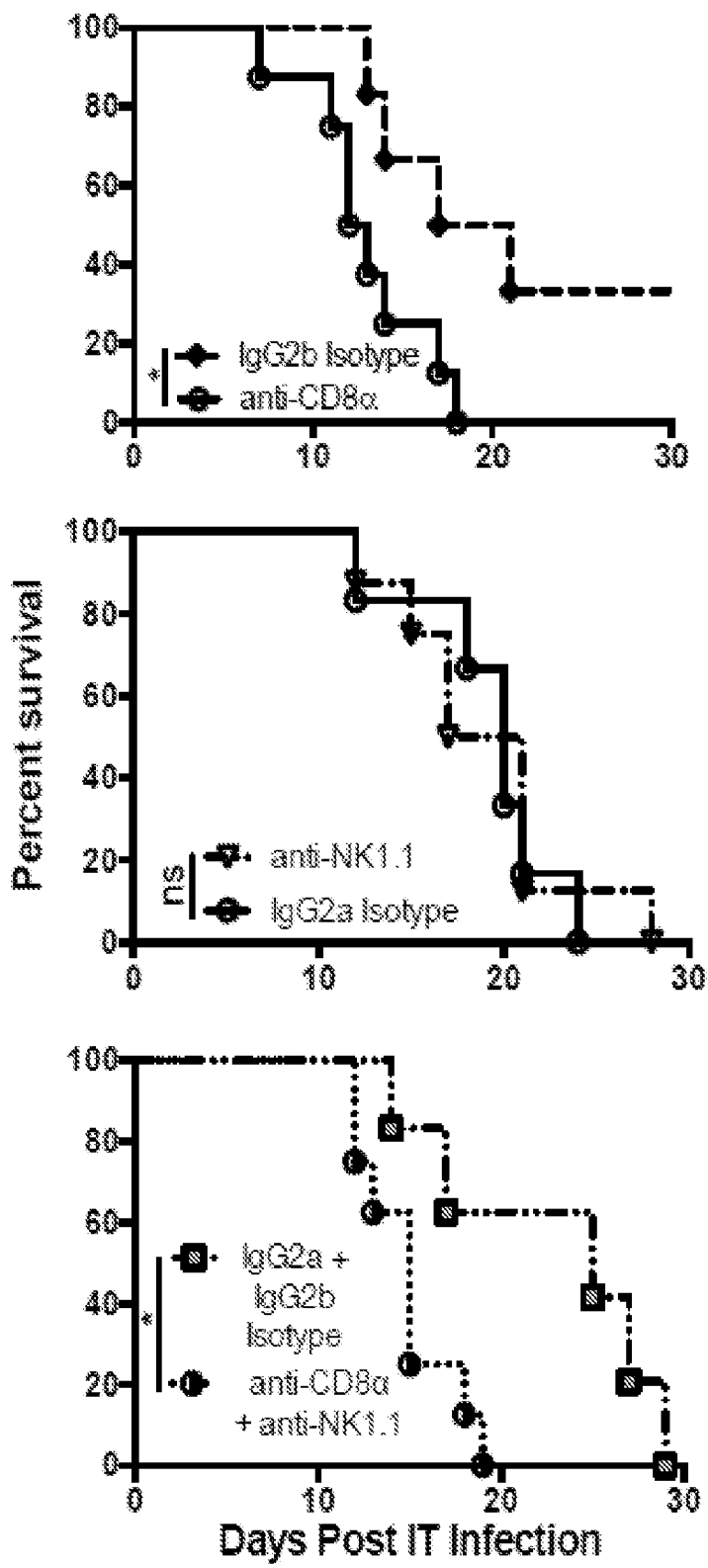

FIGS. 7 A-B depicts the survival benefit after MCMV IT therapy without CD8+ T cells or NK cells. Mice were depleted of CD8+ and/or NK1.1+ cells as described in the materials and methods (n=8 mice per group) or the relevant isotype control antibodies (n=6 mice per group). A) Tumor growth, represented as change in tumor area (mm$^2$) over time, is shown from the day of the first intratumoral injection. B) Kaplan Meier survival curves of the different antibody depletion groups compared to the relevant isotype controls from day of tumor implantation until tumors were above 100 mm$^2$. Significance was assessed by a logrank test, p<0.05=*.

FIGS. 8 A-E depicts the tumor antigen-specific CD8+ T cells in the tumor, which were PD-1$^{hi}$ and dysfunctional when tumors were beginning to grow again after MCMV IT infection. Mice received 1×10$^4$ Pmel-Is one day prior to tumor implantation. Recipients were vaccinated by the IT route when the tumor reached 20 mm$^2$. Tumors and spleens were collected D7 after MCMV-gp100 IT infection and assayed. A) Shown is the frequency of Pmel-Is in the tumor 7 days after initial MCMV-gp100 infection (MCMV-gp100 IT, n=6; WT-MCMV IT, n=5). Data are combined from 2 independent experiments. B) Mean fluorescence intensities of PD-1 on total CD8+ T cells and Pmel-Is. C) Representative histograms of the PD-1 expression of CD8+ T cells or Pmel-Is. D) Ex vivo Cytokine production and degranulation in response to native gp100 stimulation of Pmel-Is. E) Representative FACs plots of PD-L1 by CD45.2 expression in tumors after PBS IT versus MCMV-gp100 IT injection (tumor from animals in FIG. 4).

Figure 9A:
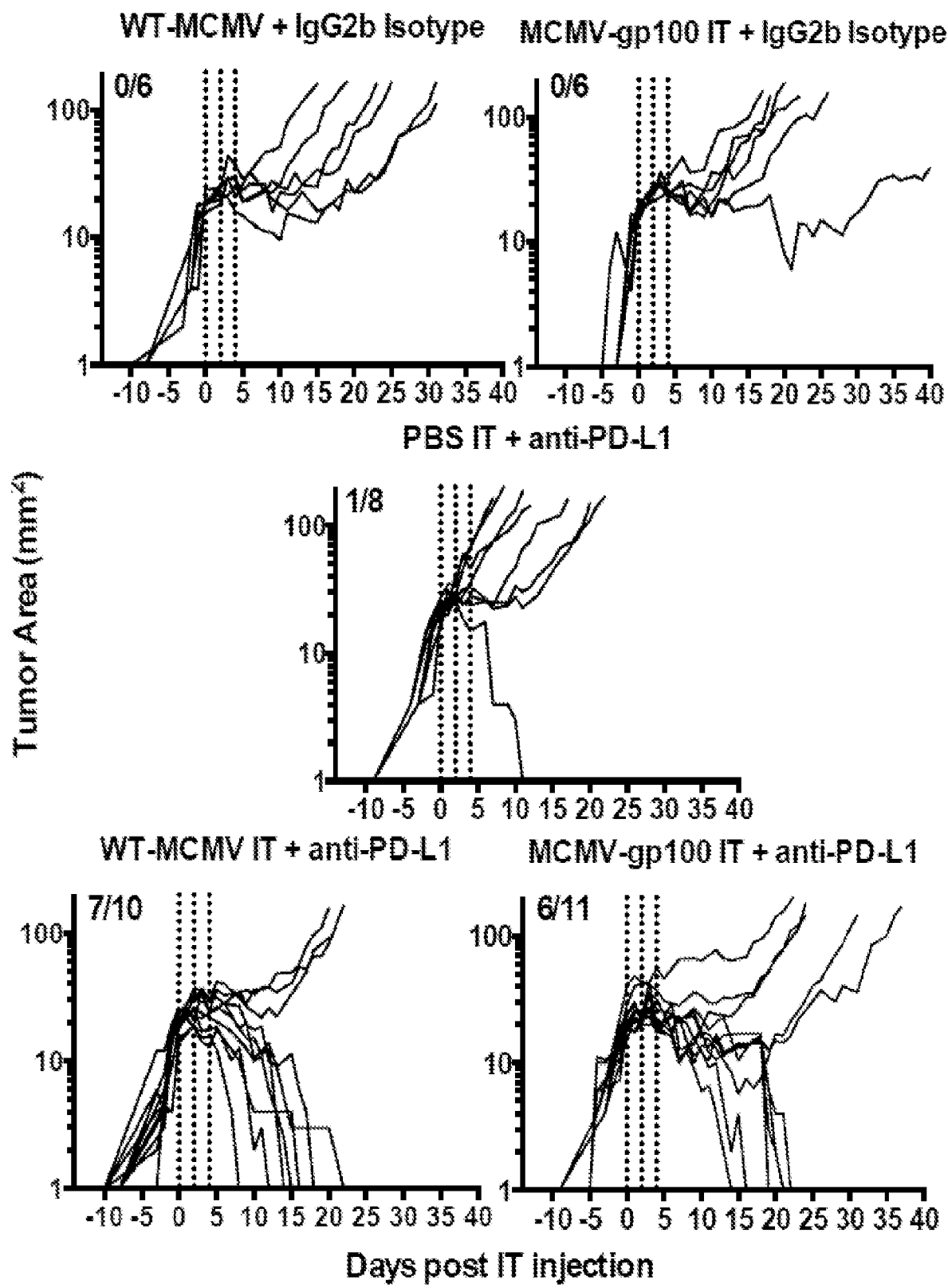
FIGS. 9 A and B depict the IT MCMV treatment as combined with anti-PD-L1 therapy, which improves B16F0 tumor growth delay and survival.
Figure 9B:
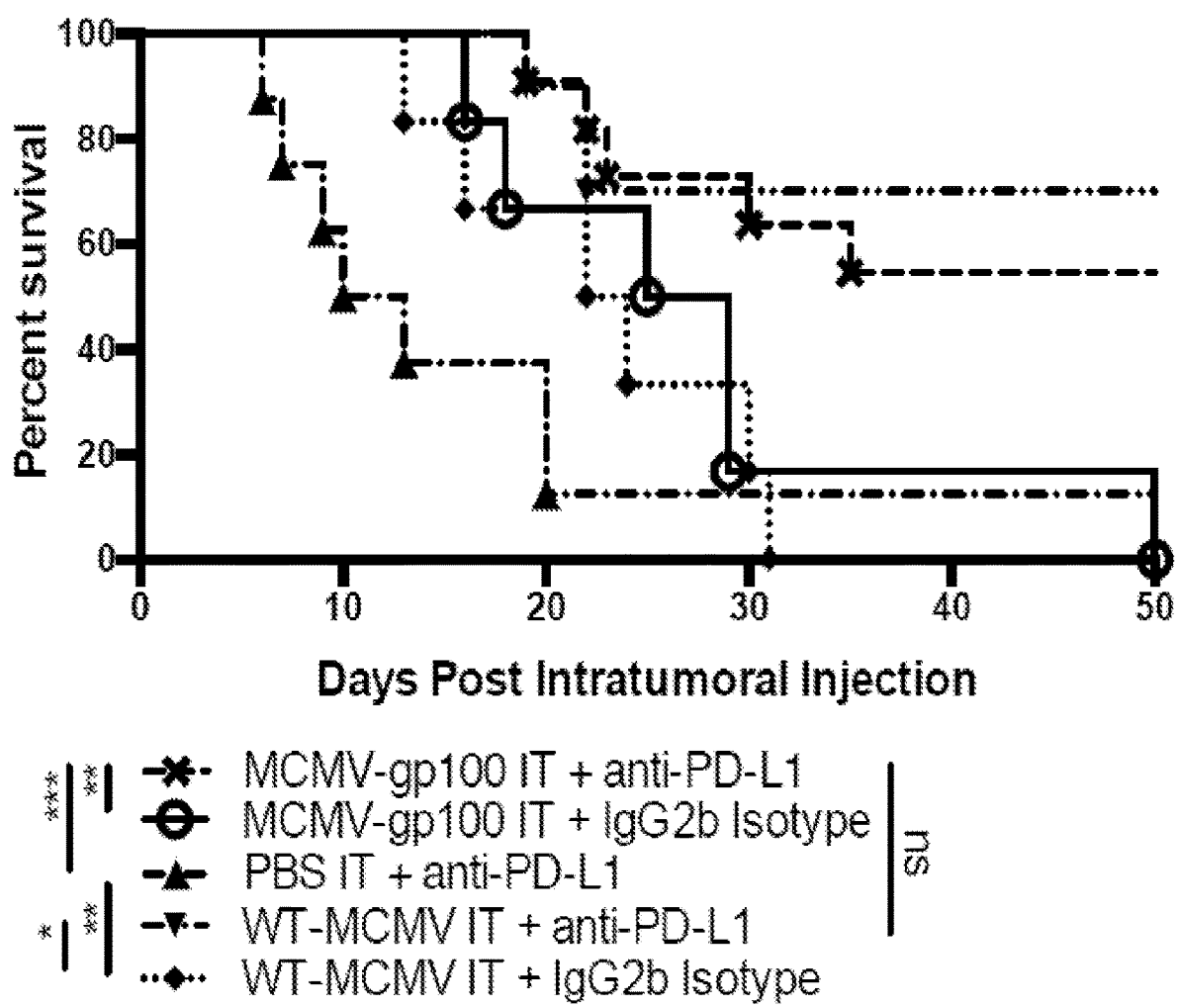

FIGS. 9 A-B depicts the IT MCMV treatment combined with anti-PD-L1 therapy, which profoundly improves B16F0 tumor growth delay and survival. A) Mice bearing B16F0 tumors were treated with anti-PD-L1 or an isotype control antibody beginning on the day of MCMV IT infection. Shown is the tumor growth as in FIG. 4 for the indicated groups of mice. Vertical dotted lines represent days of MCMV IT infection. Fractions in each graph represent the number of animals that cleared the tumor out of the number of animals tested. B) Kaplan-Meier survival curve of the mice in each treatment group.

Figure 1B:
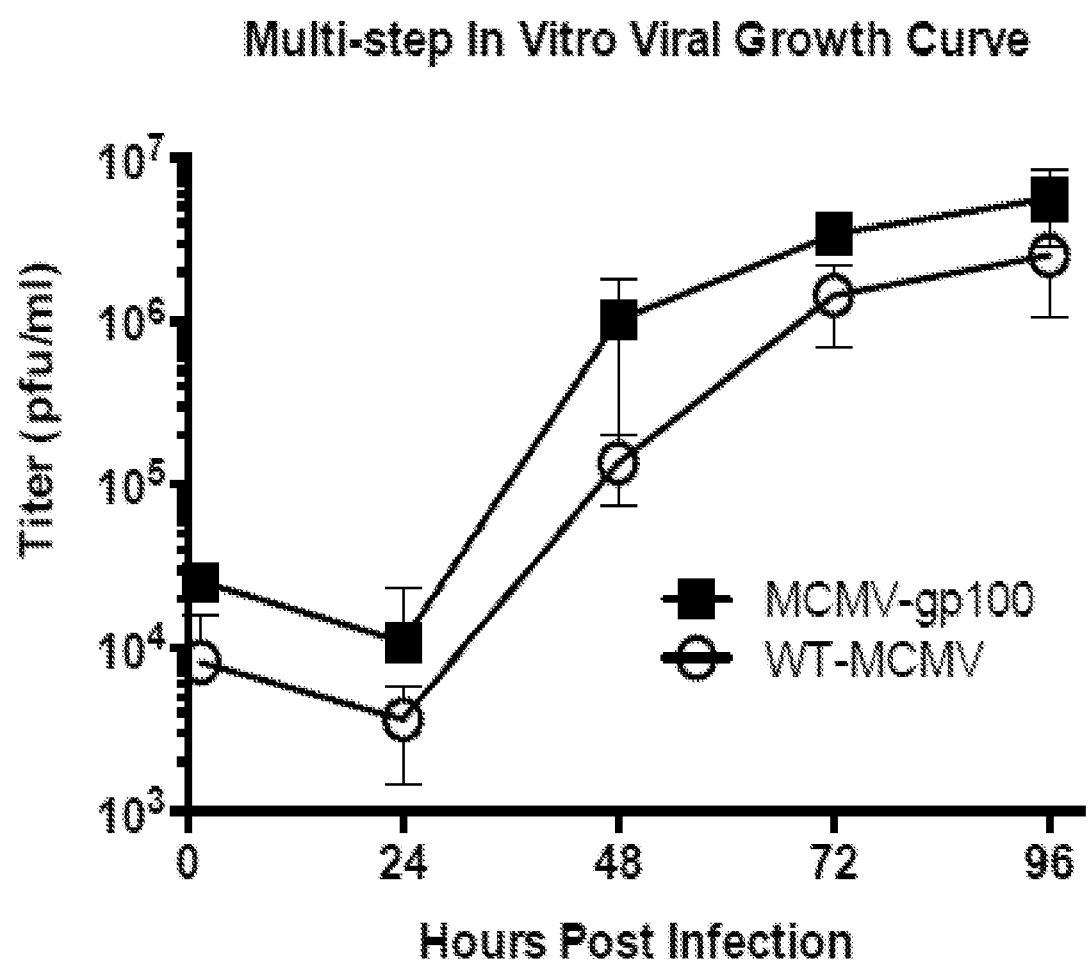
Figure 1C:
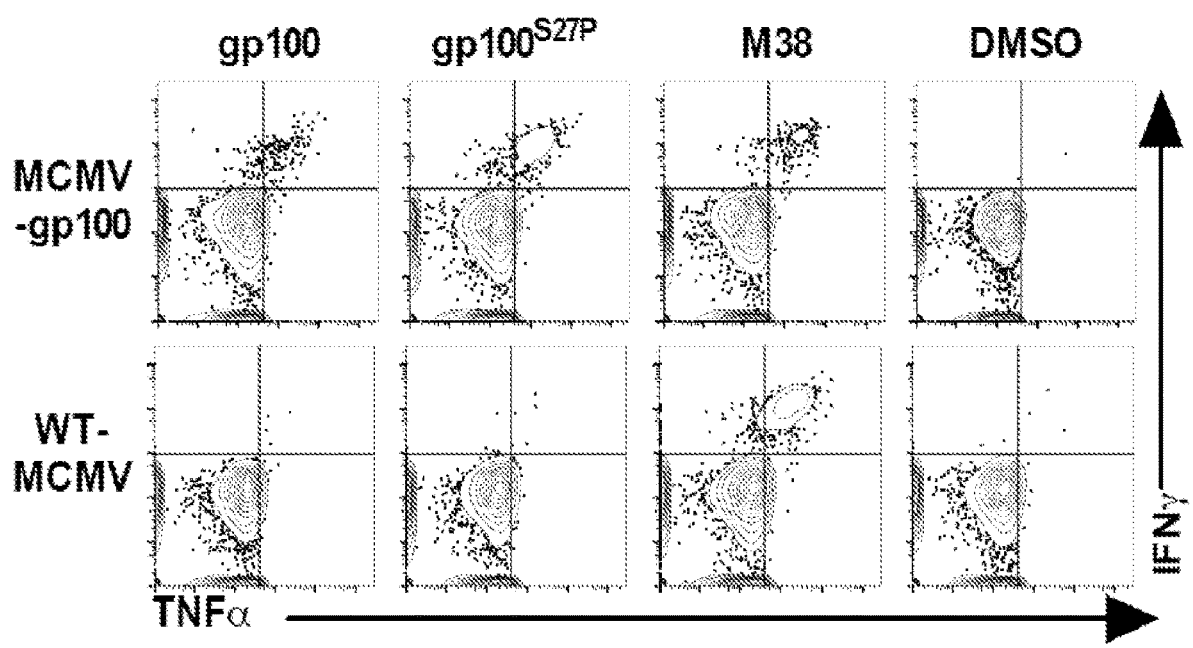
Figure 1D:
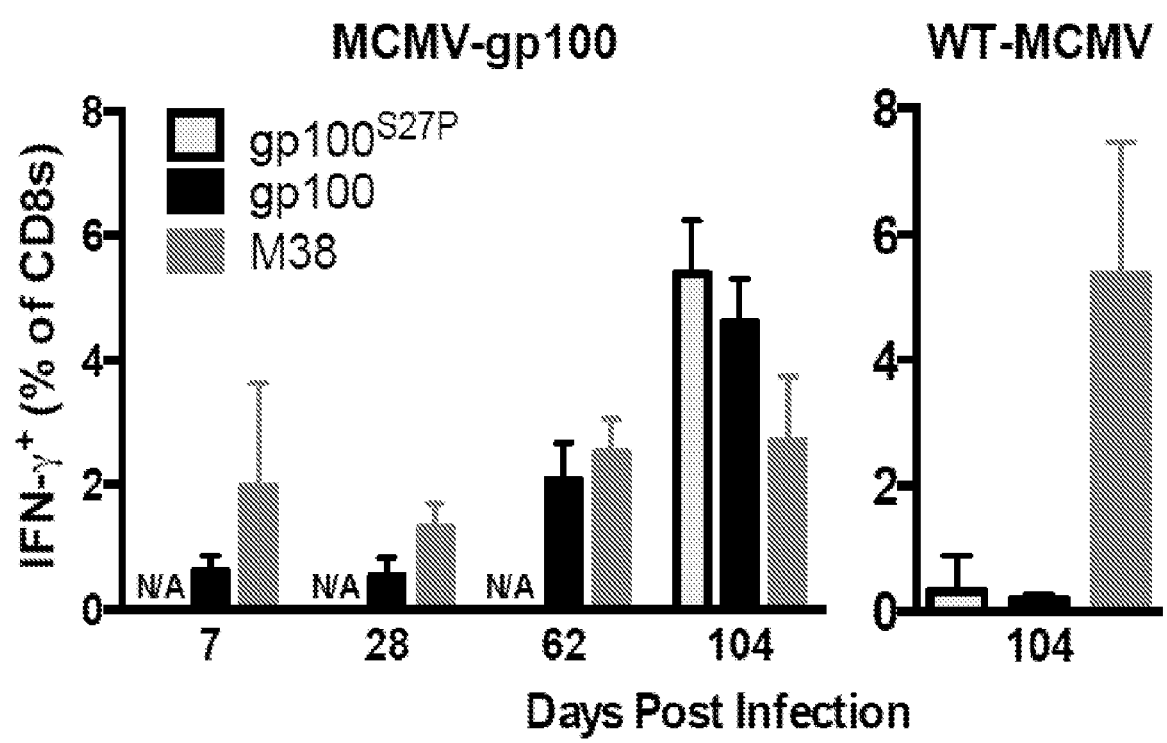

FIG. 10 shows that the primary tumor clearance after MCMV IT treatment induces resistance or rejection of secondary tumor challenges. Any animal that cleared a primary tumor was re-challenged with $2\times10^5$ B16F0s in their opposite flank 2-3 weeks after initial tumor clearance. A) Shown is the tumor growth starting from the day of tumor rechallenge. For the sake of clarity and fitting the data to a log scale, individual tumor area lines are spaced out below 1 mm$^2$ when no nodule was evident. Fractions in each graph represent the number of animals that rejected tumor challenge out of the number of animals tested. B) Mice were infected by the IP route with $2\times10^5$ pfu WT-MCMV or MCMV-gp100 and $2\times10^5$ B16F0s were implanted subcutaneously 106 days later. Shown is the tumor growth as displayed in FIG. 2. T cell responses in the blood of these mice, prior to tumor implantation, are shown in FIGS. 1c and 1d. C) Kaplan-Meier survival curve of rechallenged mice from WT-MCMV IT+anti-PD-L1 treated, MCMV-gp100 IT+anti-PD-L1 treated and prophylactically WT-MCMV or MCMV-gp100 vaccinated mice. Significance was assessed by a logrank test, p>0.05=ns, p<0.05=*, p<0.01=, p<0.001=*, p<0.0001=****.

FIGS. 11 A-D indicates that the MCMV-gp100 is able to infect and spread in B16F0s at low and high MOIs. A) Representative images of GFP-expression of live B16F0s infected or mock infected with MCMV-gp100 at the indicated times post infection. Scale bars are 0.1 mm. B) Top panel shows representative GFP-expression (infection) of uninfected B16F0s cells (open histogram) versus infected B16F0s (MOI=10, grey histograms) at D2 post infection. Bottom panel shows representative Live/Dead stain of uninfected and uninfected cells at D2 post infection. C) Representative FACs plots of MHC-I (H-2D$^b$ and H-2K$^b$) and MHC-II (I-A/I-E) by GFP (Infection) at D1 and D2 post "spinfection" with MCMV-gp100. Black dots represent cells in uninfected wells and grey dots represent cells in infected wells. D) Representative FACS plots of CD80 and CD86 expression by infected (MOI=10) or uninfected B16F0s at D1 and D2 post "spinfection" with MCMV-gp100. White histogram represents uninfected wells, dark grey histogram represents infected cells from infected wells. All these experiments were repeated twice and done in duplicate or triplicate.

Figure 12:
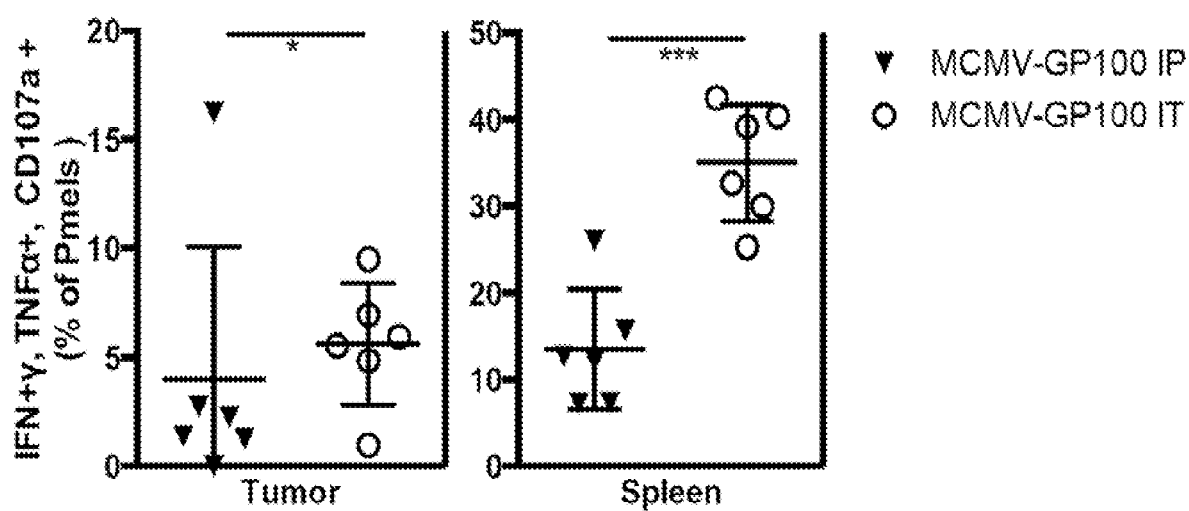
FIG. 12 illustrates the impact of MCMV IT on T-cell function.

FIG. 12 shows the function of Pmel-I T cells recovered from tumors (left panel) or spleens (right panel) after MCMV-gp100 vaccination by the intraperitoneal (IP) route (filled triangles) or MCMV-gp100 vaccination by the IT route (open circles). Shown is the frequency of all Pmel-I T cells that produced both IFN-γ and TNF-α after stimulation in vitro for 5 hours.

Materials and Methods

Mice and Tumor Model

C57BL/6J and Pmel-I T cell transgenic mice (B6.Cg-Thy1$_a$/Cy Tg(TcraTcrb)8Rest/J) mice were purchased from Jackson Laboratory and bred in house for use in all experiments. Donor and recipient mice were sex-matched for all adoptive transfers. For most experiments, mice were between 6 and 12 weeks old at the time of tumor implantation. For the data shown in FIG. 3 D-F, mice were 6 to 12 weeks old at the time of primary MCMV infection and tumors were implanted 8 or 52 weeks later. For primary tumors, mice were subcutaneously challenged in the shaved right flank with $1\times10^5$ B16F0s suspended in HBSS (Cell-Gro). For tumor rechallenge experiments (FIG. 10), animals that had cleared a primary tumor were re-challenged with $2\times10^5$ B16F0s in the shaved left flank. In all cases, tumor area was calculated by multiplying the length and width (in millimeters) of the tumor as measured with a 6-inch digital caliper (Neiko). Animals were sacrificed when the tumor was growing exponentially and had exceeded ~100 mm$^2$ in area, or when the tumors had ulcerated, or the animals had become moribund. The Thomas Jefferson University Institutional Animal Care and Use Committee reviewed and approved all protocols.

Virus Strains, Cell Lines and In Vitro Infections

To produce the recombinant strain MCMV-gp100$^{S27P}$, the sequence encoding the altered gp100$^{S27P}$ peptide (EGPRNQDWL) was fused to the 3' end of the sequence encoding GFP, upstream of the stop codon, as done previously with SIINFEKL[38]. The fusion construct was recombined with MCMV encoded with a bacterial artificial chromosome (BAC, strain MW97.01, hereafter called WT-MCMV[23]) and targeted to replace the m128 exon (IE2 gene) using established techniques[24]. Viral stocks were prepared on M2-10B4 stromal cells as previously described[41]. In brief, $2-4\times10^6$ cells were infected at an MOI of 0.01. Cells were collect 5-6 days later, dounced, and the supernatant was ultra-centrifuged to concentrate the virus which was subsequently frozen at −80° C. until use. The single- and multistep growth analyses shown in FIGS. 1 and 3 were performed by infecting M2-10B4 cells or B16F0 cells with an MOI=0.1 (multistep), or an MOI=10 (single step), harvesting lysates at the indicated times and measuring viral growth by plaque assay without centrifugal enhancement on M2-10B4s as previously described[41]. In brief, subconfluent layers of M2-10B4s were infected with lysates at several different titrations, covered with viscous media, incubated for 5 days, and stained with crystal violet for plaque counting. For the data shown in FIG. 3 $f$ and FIG. 11, cells were "spinfected" to increase the frequency of infected cells detectible 1 day after infection. Spinfection was accomplished by spinning cells at 800×g for 30 minutes after adding virus. Control, uninfected cells were treated in the same way except that no virus was added to the culture. In all cases, M2-10B4s were grown in RPMI (CellGro)+1% PenStrep (Gemini, Benchmark)+10% FBS (Gemini). B16F0s were grown in DMEM (CellGro)+1% PenStrep+10% FBS.

Infections and Vaccinations of Mice:

For infection of mice without tumors (FIG. 1 and FIGS. 4 $e$ and $f$), animals received $2\times10^5$ plaque forming units (PFUs) of MCMV-gp100, or MCMV-K181 by the IP route in a single injection of 100 μl. For IP and ID infections of tumor-bearing mice, animals received $5\times10^5$ PFUs of the indicated virus in a single injection of 100 μl for IP infection and for 25 μl for ID infection. In all cases, ID infection was performed in the skin next to the tumor implantation site.

For IT infections, animals received 5×10⁵ PFUs of the indicated virus in 30 μl volume or 30 μl of PBS every other day for 3 total injections.

Adoptive Transfer of Pmel-I T Cells:

Spleens were harvested from naïve Pmel-I transgenic mice, passed through a 70 μm cell strainer to form single cell suspensions and washed twice with T cell media (RPMI 1640 [Cellgro] with L-glutamine+10% FBS+1% PenStrep and 5×10⁻⁵ M β-mercaptoethanol [Omnipur, Calbiochem]). Total splenocytes were counted on a Z2 Coulter Particle Count and Size Analyzer (Beckman Coulter) and the sample was assessed for frequency of CD8⁺ T cells by flow cytometry. Based on these data, total splenocytes were suspended in PBS so that the desired number of CD8⁺ T cells was present in 100 μl, which is the volume that was retro-orbitally injected into recipient C57BL/6 mice.

Lymphocyte Isolation, Analyses and Intracellular Cytokine Staining

Spleens were suspended in T cell media and mechanically processed through a 70 μm nylon filter to achieve a single cell suspension. For recovery of lymphocytes from tumors, tumor masses were placed in tumor digestion media (lx HBSS [Cellgro], 0.1 mg/ml Collagenase A [Worthington], 60 U/ml DNase I [Roche],[52] and minced using the gentleMACS™ Octo Dissociator using C Tubes (Miltenyi Biotec). Minced tumors in digestion media were incubated at 37° C. for 30 minutes with continuous rotation. Digested tumors were minced again using the gentleMACS™ Octo Dissociator, then washed twice with T cell media and mechanically filtered through a 70 μm nylon filter to make a single cell suspension. Lymphocytes were then either directly assessed by flow cytometry or tested for their ability to produce cytokines upon stimulation. For analyses of cytokine production by cells from spleens and tumors, 1-2×10⁶ cells were incubated in T cell media in a round bottom 96-well plate[53] for 5 hours at 37° C. in 5% $CO_2$. The final incubation volume was 100 μl and contained 1 μg/ml of the indicated peptide (synthesized by Genemed Synthesis) and 1 μg/ml brefeldin A (GoldiPlug, BD Biosciences), as well as fluorescently labeled antibody specific for CD107a. At the end of the incubation, cells were washed twice with ice-cold FACS buffer (PBS, 0.05% Sodium Azide, 1% FBS) and stained with antibodies specific for surface proteins followed by analyses of intracellular IFN-γ and TNF-α using the BD Cytofix/Cytoperm kit (BD Biosciences) and following the manufacturer's instructions.

In FIGS. 1C and D, ~150 μl of peripheral blood was collected from the retro-orbital sinus. Red blood cells were lysed for 5 minutes in red blood cell lysis buffer (150 mM $NH_4Cl$, 10 mM $NaHCO_3$) and the remaining white blood cells were washed twice and resuspended in T cell media. Approximately ⅕ of the recovered cells were added to individual wells and incubated as above for 3 hours and without the antibodies specific for CD107a. For Treg staining, cells were fixed with FOXP3 Fix/Perm buffer (Biolegend) for 10 minutes on ice and then permeabilized for 15 minutes with FOXP3 Perm buffer (Biolegend) before adding 2.5 μl of anti-FOXP3 per sample.

Antibodies and FACS Analysis

Analyses of lymphocytes were performed using the following antibodies: CD3 (clone 500A2), CD4 (clone GK1.5), CD8α (clone 53.6.7), CD8β (clone YTS156.7.7), PD-1 (clone 29F.1A12), PD-L1 (clone 10F.9G2), H-2D$^b$ (clone KH95), H-2K$^b$ (clone AF6-88.5), CD80 (16-10A1), CD86 (GL-1), NK1.1 (clone PK136), CD11b (clone ICRF44), GR-1 (clone RB6-8C5), FoxP3 (clone 150D), I-A/I-E (clone M5/114.15.2), IFN-γ (clone XMG1.2), TNF-α (clone MP6-XT22) and CD107a (clone 1D4B). Pmel-I T cells were identified using Thy1.1 (clone OX-7). All antibodies were purchased from Biolegend or BD Biosciences. Stained cells were analyzed using the LSR II flow cytometer (BD Biosciences) and FlowJo Software (TreeStar, Ashland, Oreg., USA).

Fluorescence Microscopy

MCMV-gp100 infected B16F0 cells were identified by the appearance of GFP expression using a Nikon Eclipse TS100 microscope, Nikon Intensilight CHGF1 illumination system, and Nikon Digital Sight DS-L3 camera controller.

In Vivo Antibody Depletions and Blockades:

To deplete CD8⁺ T cells or NK cells, mice were treated with 300 μg of anti-CD8a (clone 53-6.72) and/or anti-NK1.1 (clone PK136) every 3 days for a total of 8 treatments, starting 2 days before tumor implantation. Treatment resulted in greater than 90% depletion of target cells (data not shown). As controls, additional animals were treated with an irrelevant IgG2a antibody (isotype control for anti-NK1.1, clone C1.18.4), or IgG2b antibody (isotype control for anti-CD8a, clone LTF-2) following the same schedule. To study the effect of PD-L1 blockade on IT infection, mice were treated with 400 μg of anti-PD-L1 (clone 10F.9G2) by the IP route on the first day of IT treatment, followed by an additional 200 μg anti-PD-L1 given every third day by the IP route for a total of 6 treatments. As a control, additional animals were treated with the IgG2b isotype control clone LTF-2, following the same schedule. All antibodies were purchased from Bio-X-Cell.

Fluorescence Microscopy:

Isolated tumors were frozen in Fisher Healthcare™ Tissue-Plus OCT (Fisher Scientific) and cut into 6-8 μm sections using a cryostat. Samples were fixed in cold acetone for 10 minutes and rehydrated with Tris-buffered saline (TBS) for 20 minutes, blocked with blocking buffer (TBS+ 3% BSA and 0.1% Tween-20) for 20 minutes and stained with antibodies specific for CD31 (clone 390), CD45.1/2 (clone A20/104), CD11b (clone M1/70), F4/80 (clone BM8) and/or MCMV pp89 (clone 6/58/1[60]) in blocking buffer for 1 hour and later co-stained with DAPI (Prolong Gold antifade—Life Technologies). The anti-pp89 antibody was purified from hybridoma supernatant using Pierce™ Protein A/G Magnetic Beads (Fisher Scientific), concentrated using Amicon Ultra-0.5 or 15 Centrifugal Filter Unit with Ultracel-100 membrane (Millipore), and labeled using Mix-N-Stain CF555 Antibody Labeling Kit (Sigma-aldrich). Anti-pp89 flourophore conjugation was confirmed by staining infected and uninfected M2-10B4s with the labeled antibody (data not shown). Images were generated with an LSM 510 Meta confocal laser scanning microscope (Carl Zeiss), the LSM image browser software (Carl Zeiss), and ImageJ (Fiji).

Statistical Analysis

Prism Version 6.0d was used for graph creation and some statistical analyses. For statistical significance, *$p<0.05$ $p<0.01$ *$p<0.001$ ****$p<0.0001$. Tumor growth was analyzed with a mixed-effects linear regression, an extension of ordinary linear regression for repeated measures over time. Heuristically, the model estimates a tumor growth curve for each animal and then appropriately averages these curves to estimate the group's average trajectory. This approach accounts for the within-animal correlation of tumor sizes over time and the potential uneven timing of readings. Tumor size was log-transformed before the analyses and was modeled as a function of time, experimental group, and their interaction. The main aim was to compare growth rates over time across the experimental groups.

Results were expressed in terms of the average daily increase of tumor size and the tumor doubling time. We also used Kaplan-Meier survival curves and the logrank test to analyze the time tumors needed to reach 100 mm$^2$ (overall survival, the approximate tumor size when animals are typically sacrificed).

Results

Construction and Characterization of MCMV-gp100$^{S27P}$

A recombinant strain of MCMV was created that expresses GFP fused to an altered version of the gp10025-33 peptide (gp100$^{S27P}$). This fusion construct was inserted into the IE2 locus and under the control of the endogenous MCMV IE2 promoter (MCMV-gp100, FIG. 1a), a strategy that has been used to stimulate robust T cell responses to recombinant antigens in the MCMV backbone[34-36]. The growth of MCMV-gp100 was similar to that of its wild-type counterpart as seen by multi-step in vitro growth curves (FIG. 1b). Infection of C57BL/6 mice with MCMV-gp100 induced the accumulation of CD8$^+$ T cells in the blood that responded to the altered and native gp100 peptides (FIGS. 1c and d). In contrast, WT-MCMV infection did not elicit gp100-specific CD8$^+$ T cells (FIGS. 1c and d).

The CMV vaccine can be grown and generated by means known to a person of ordinary skill in the art. Typically, the viral cells are grown in a tissue culture medium and harvested. After harvest, the cells are purified and diluted in a sterile solution suitable for injection, for example PBS. Appropriate suitable excipients, solutions, components, and the like can be provided as known to a person of ordinary skill in the art. For Example, Harlow & Lane, Using Antibodies, A Laboratory Manual, Cold Spring Harbor Laboratory Press, Cold Spring Harbor, N.Y., 1998; Remington: The Science and Practice of Pharmacy," 20th edition, Gennaro, Lippincott (2000); and Molecular Cloning: A Laboratory Manual, 3rd Ed., Sambrook and Russel, Cold Spring Harbor Laboratory Press, 2001; teach a person of ordinary skill in the art how to make and use an antibody or cell culture, suitable for injection. Indeed, in particular, Remington teaches appropriate formulations and strategies to ensure that the injectable vaccine is isotonic and suitable for injection; whereas Harlow, and Molecular Cloning otherwise teach appropriate steps for cloning or modification of cells for inclusion in the CMV vaccines as described herein, or the antibody therapeutics to be co-administered with the CMV vaccine.

As would be expected the vaccine, therefore, comprises CMV cells, in one or more of the forms as identified herein, a delivery vehicle, and suitable excipients and components for injection. It is expected that certain impurities will remain, including the culture medium and/or purification compositions as known to a person of ordinary skill in the art.

Figure 2A:
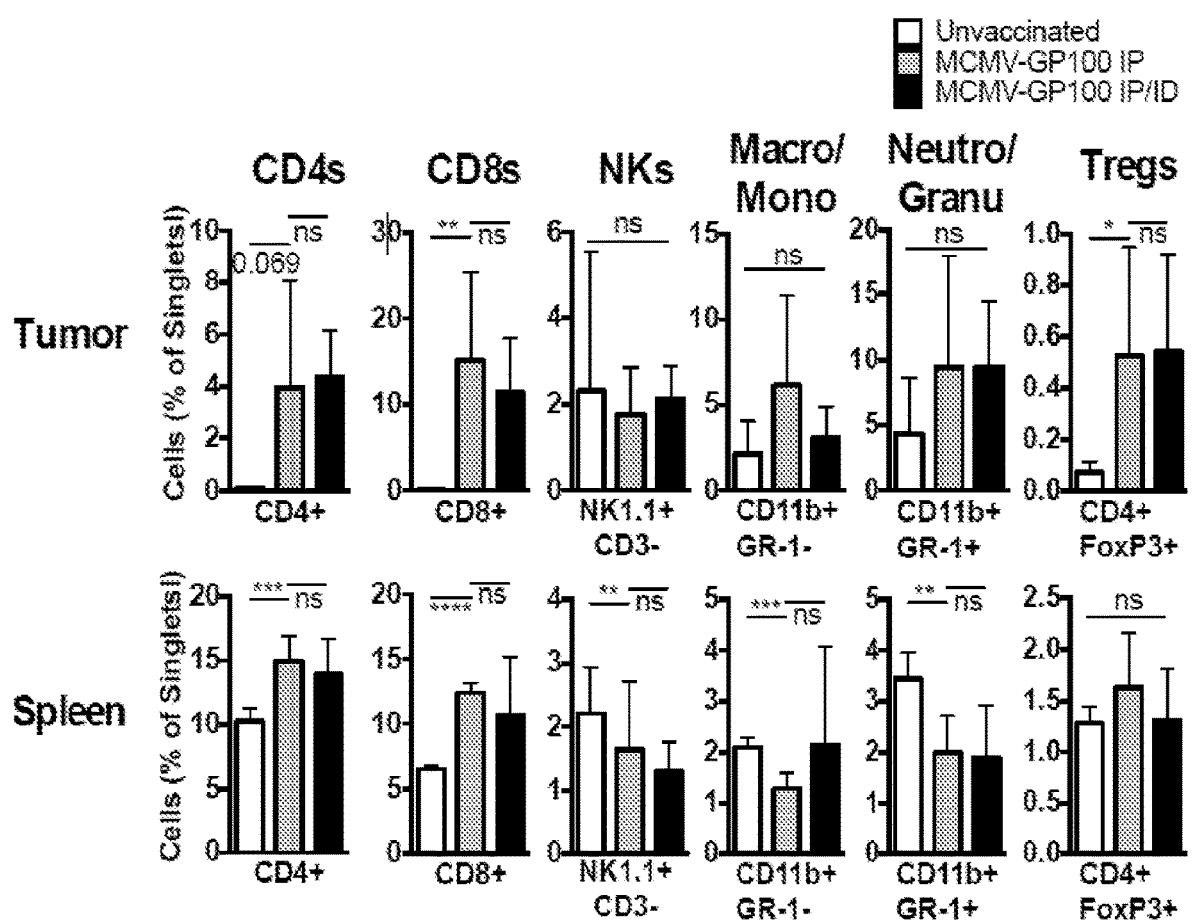
FIGS. 2 A-D depicts an intraperitoneal and intradermal infection with MCMV-gp100.
Figure 2B:
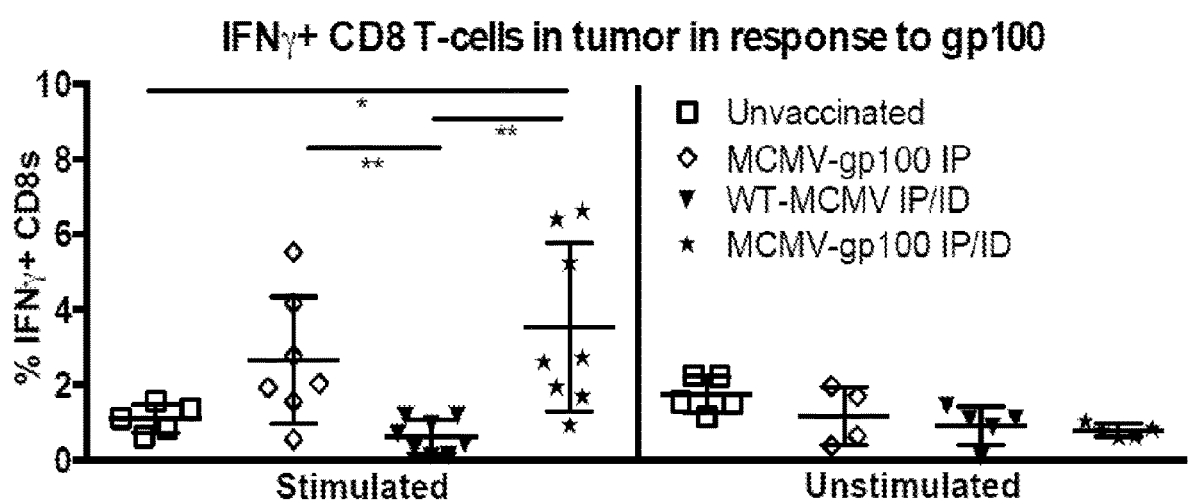
Figure 2C:
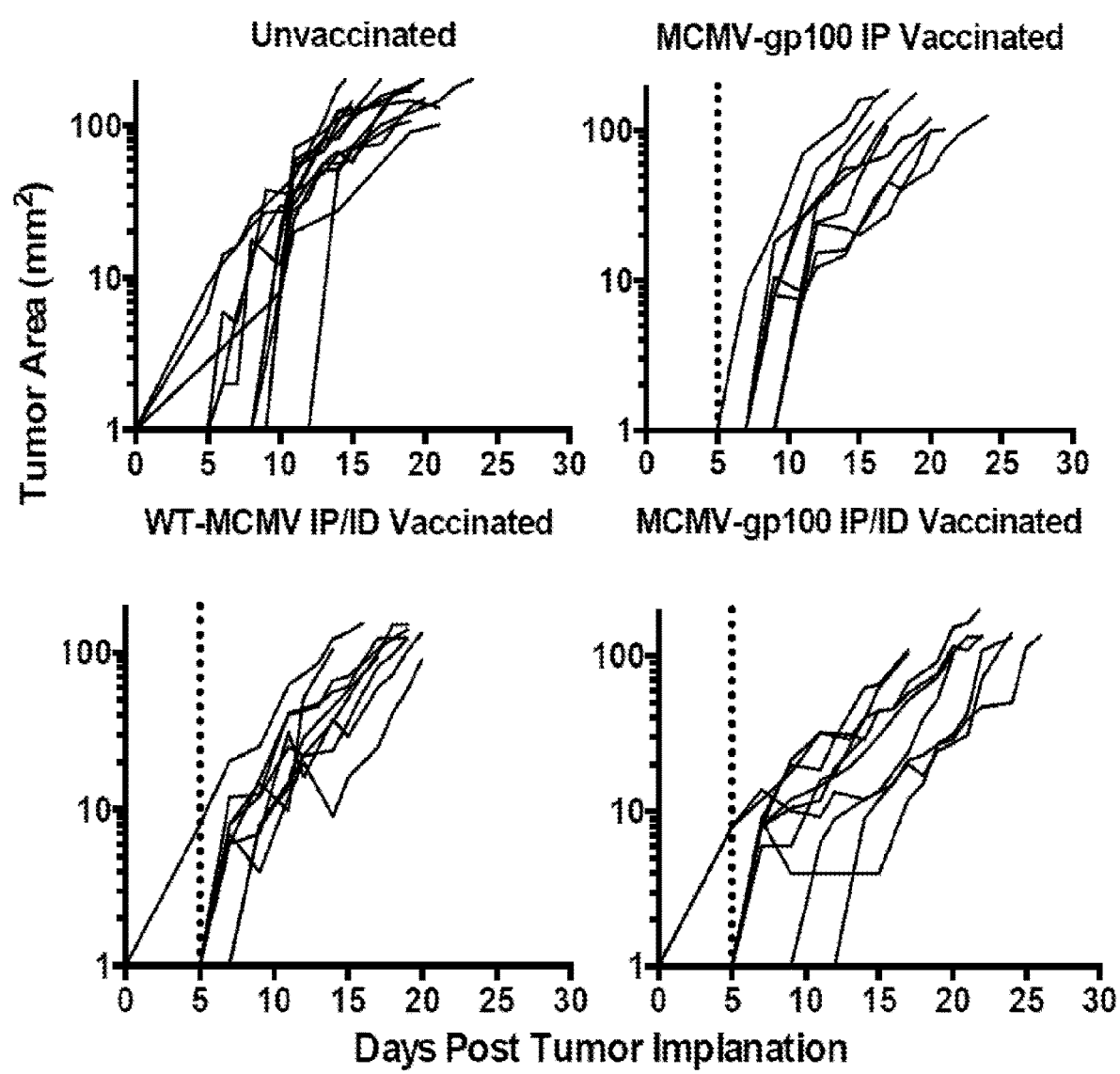
Figure 2D:
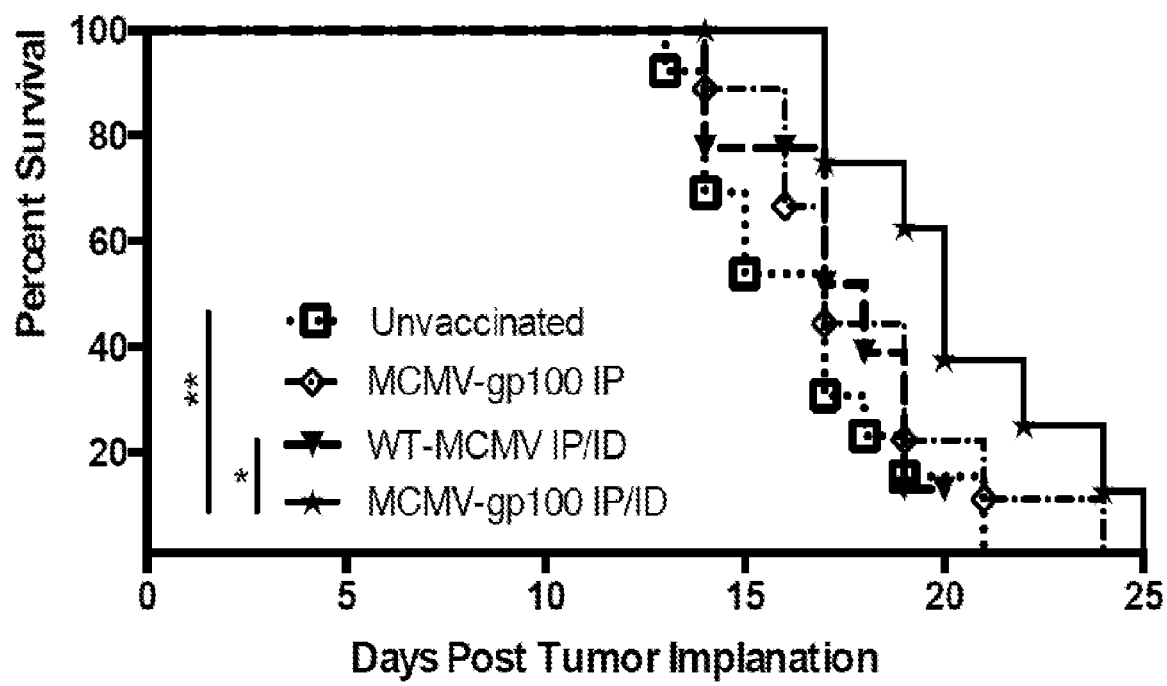

Therapeutic Intraperitoneal and Intradermal Vaccination with MCMV-Gp100 Induces Minimal Growth Delay of B16F0 Tumors To determine the therapeutic efficacy of MCMV-gp100 vaccination, B16F0 tumors were subcutaneously implanted in the flank and mice were vaccinated five days later with MCMV-gp100. Recent work has shown that the site of infection or vaccination can influence the migration of CD8$^+$ T cells and subsequent protection[37,38]. Therefore, we vaccinated mice by the IP route alone or in combination with an ID vaccination in the skin adjacent to the tumor. In both cases, vaccination caused increased infiltration of CD4$^+$ T cells, CD8$^+$ T cells, and FoxP3$^+$ regulatory T cells (T$_{REG}$), but no increase of NK Cells, Neutrophils, Granulocytes, Macrophages, or Monocytes (FIG. 2a). Moreover, vaccination with MCMV-gp100 by either route induced an increased frequency of gp100-reactive T cells within the tumor, as measured by intracellular cytokine stimulation (FIG. 2b) or by using gp100-specific Pmel-I TCR transgenic T cells[35] (data not shown). However, there was only a small effect on tumor growth in comparison with unvaccinated animals (FIG. 2c) and only the combined IP/ID routes of vaccination improved survival compared to unvaccinated mice or mice infected via the IP/ID routes with WT-MCMV (FIG. 2d). Moreover, median survival was only increased by 3 days and this was not significantly greater than mice vaccinated with MCMV-gp100 by the IP route alone (FIG. 2d). These data suggest that systemic and dermal-localized MCMV-gp100 vaccinations were able to cause expansion and tumor infiltration of gp100-specific CD8$^+$ T cells, but were ineffective as therapeutic treatment of subcutaneous B16F0 melanoma lesions.

Figure 3A:
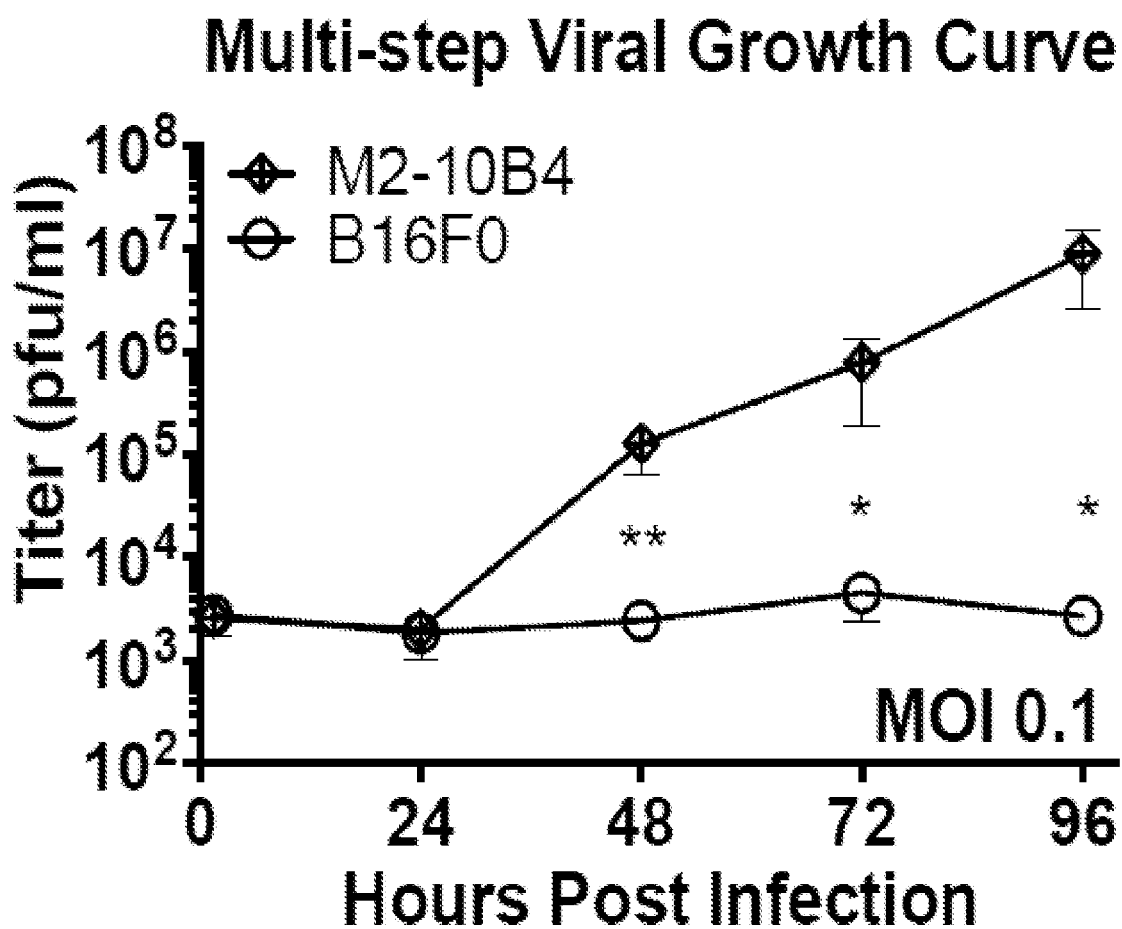
FIGS. 3 A-E depicts MCMV-gp100 infection of B16F0s in vitro induced cell death and increased immunogenicity.
Figure 3B:
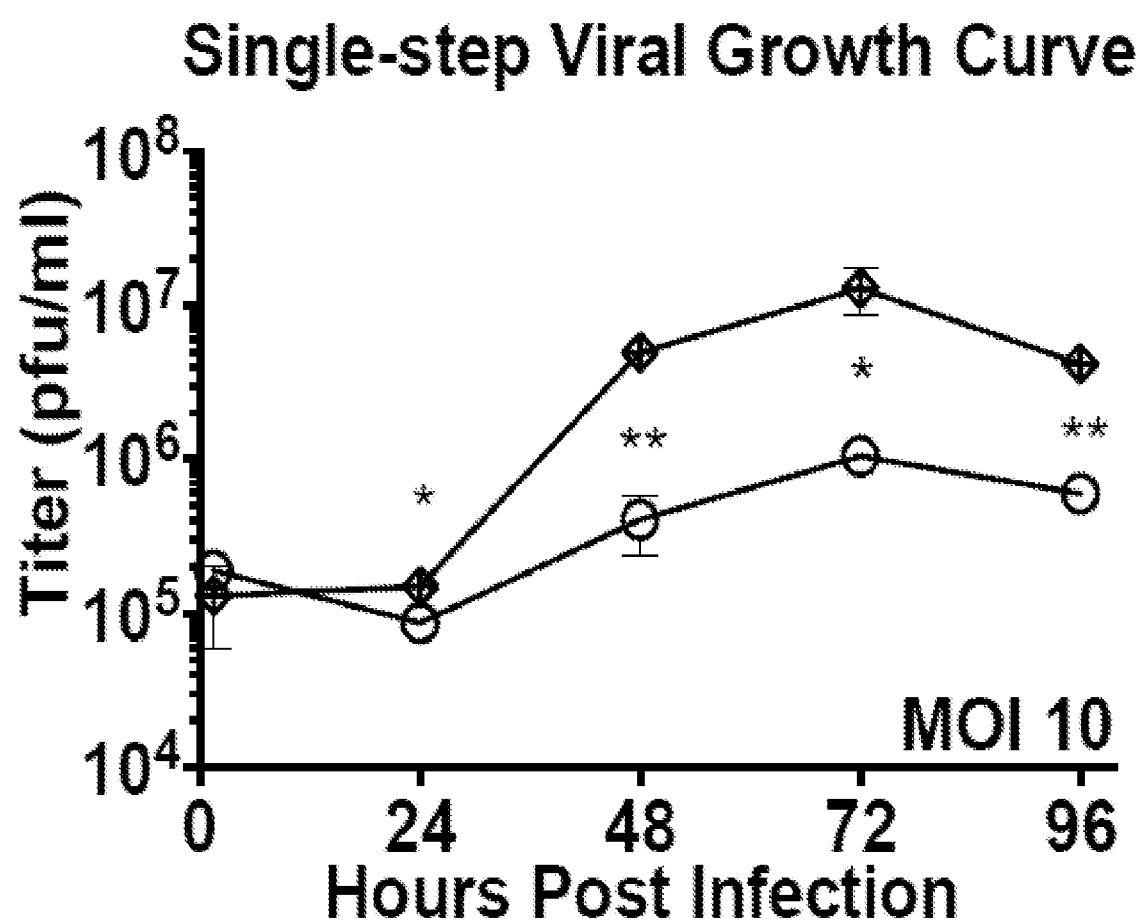
Figure 3C:
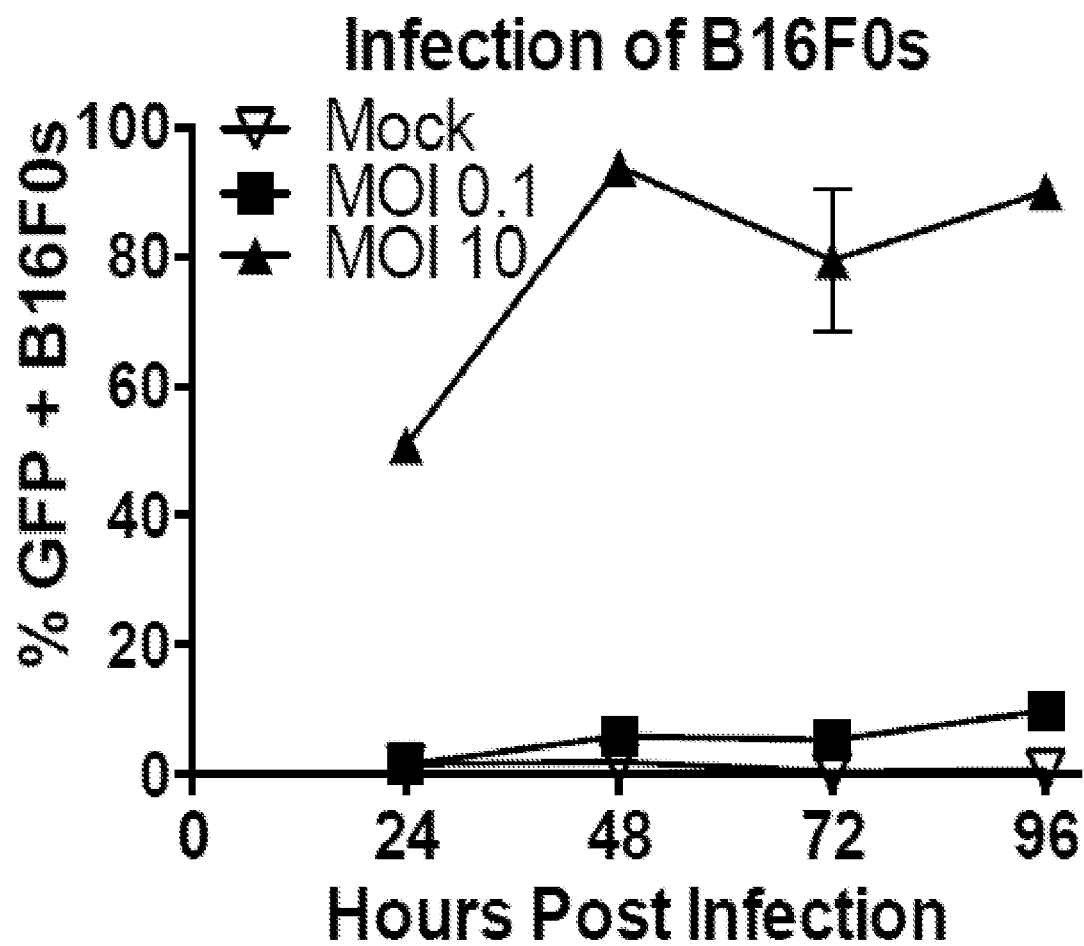
Figure 3D:
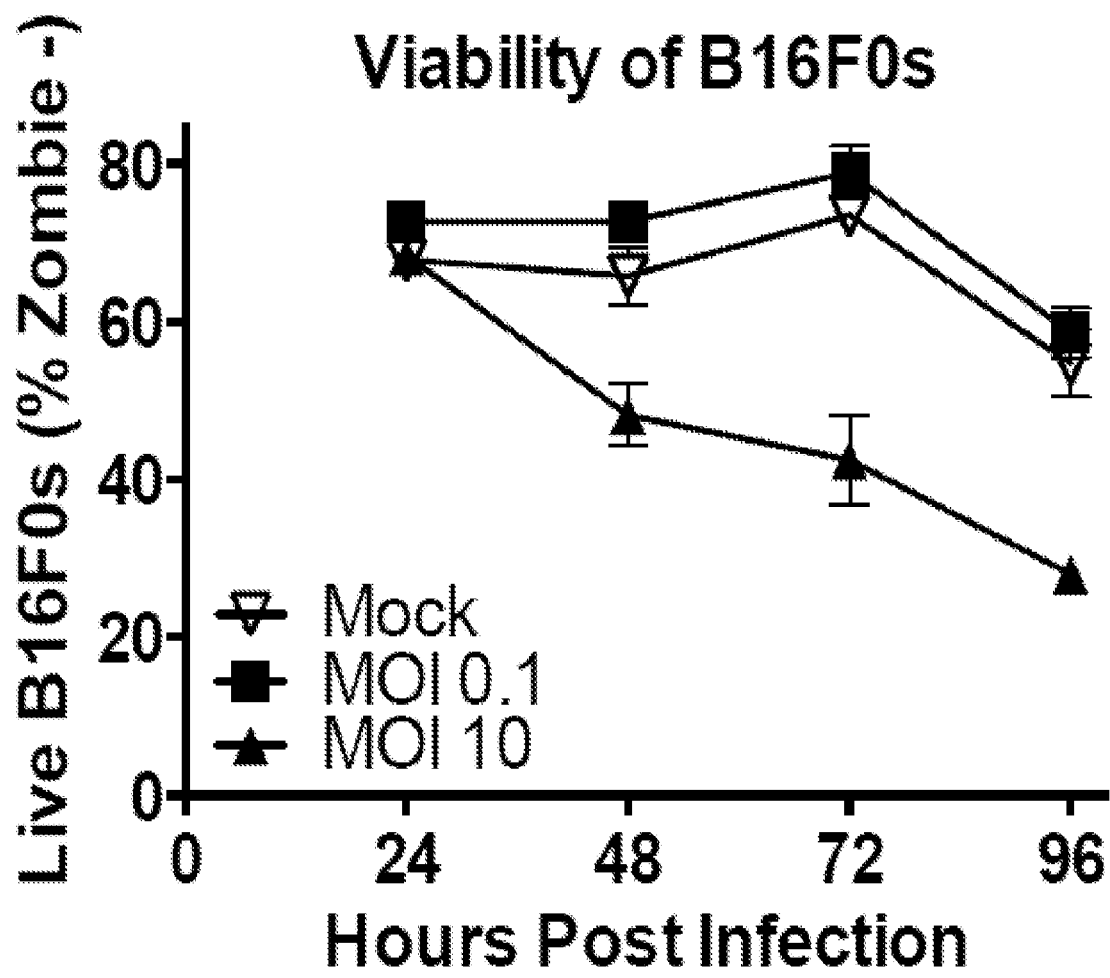
Figure 3E:
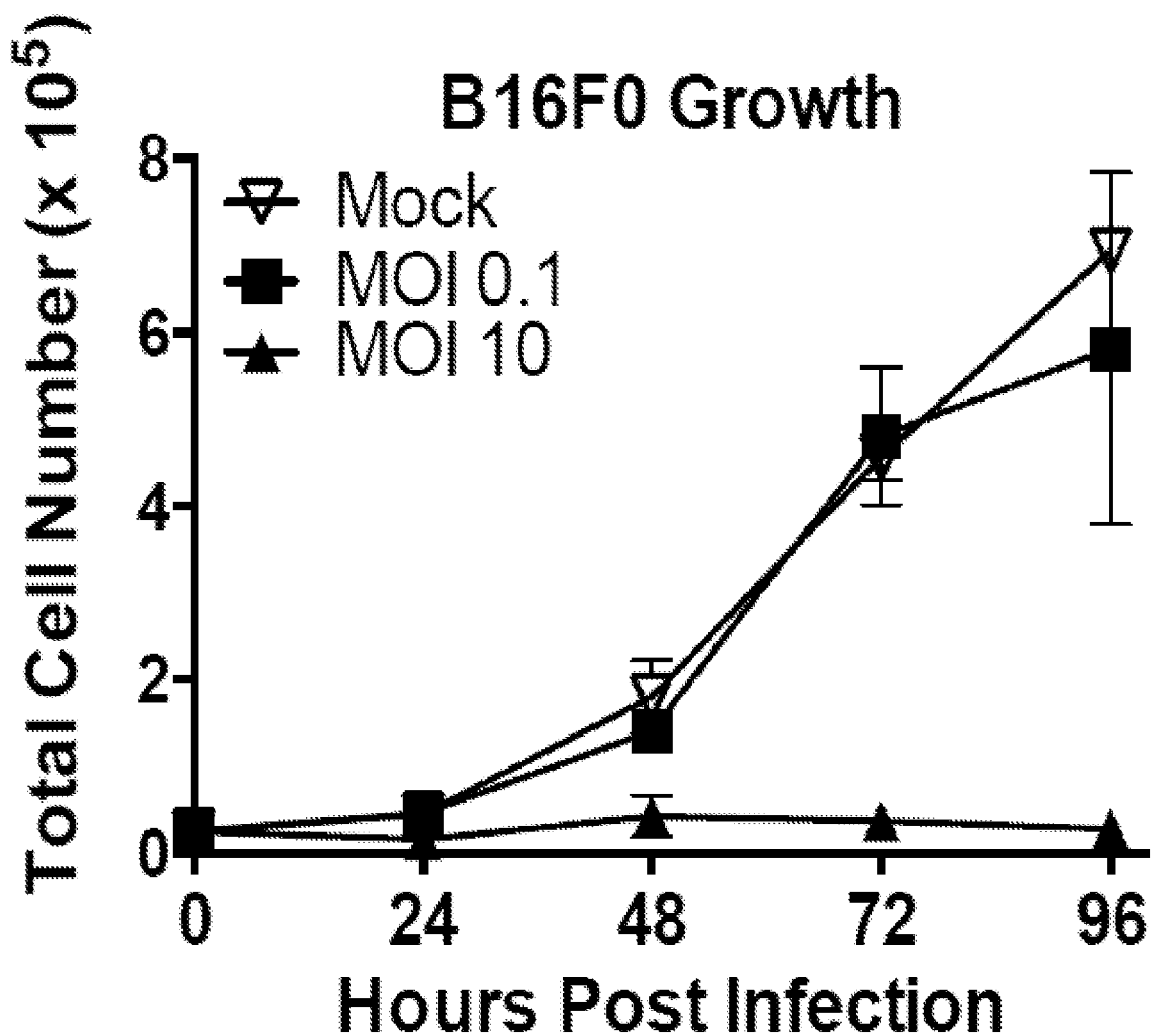

Intratumoral Infection with MCMV Significantly Delays Tumor Growth and Improves Overall Survival As systemic vaccination was unremarkable, we turned to alternative infection routes. Recent work has shown that the introduction of therapies directly into tumors can lead to therapeutic responses[6,7,8]. We found that MCMV-gp100 could infect B16F0s in vitro at low and high multiplicities of infection (MOI) and spread through the culture, as seen by GFP-expression of infected cells (FIG. 3 and FIG. 11), although the recovery of infectious virus from B16F0s was poor compared to the well-characterized M2-10B4 cell line[58] (FIGS. 3a and b). At a high MOI, most B16F0s in the culture were infected (FIG. 3c) and this correlated with poor growth of the B16F0s and cell death (FIGS. 3d and e). In addition, infected B16F0 cells expressed more MHC-I, MHC-II and the co-stimulatory molecule CD86 compared to uninfected cells in the same wells (FIG. 11). Thus, MCMV infection of B16F0s inhibits tumor growth, kills infected cells, and makes these cells better targets for the immune system. Together, these data suggest that MCMV may be oncolytic after direct infection of established tumors.

To determine whether intratumoral (IT) infection with MCMV would improve the therapeutic impact of vaccination, mice were implanted with B16F0s subcutaneously, as above. When tumors were approximately 20 mm$^2$ (~7-14 days after tumor implantation), they were injected directly with WT-MCMV, MCMV-gp100, or PBS, every other day for 3 treatments (FIG. 4a). For comparison, another group was vaccinated by IP and ID routes as above (FIG. 2), and then given PBS by the IT route. As shown in FIG. 4b, direct IT infection with MCMV had a marked effect on the growth of established tumors. Mice treated with PBS IT or MCMV-gp100 IP/ID+PBS IT had an average daily tumor growth rate after the IT injection of 21% and 19% respectively, and the tumor size doubled every 3.6 or 3.7 days respectively (FIG. 4b). Strikingly, when mice were infected with either WT-MCMV or MCMV-gp100 by the IT route, the average daily growth rate post IT injection was reduced to 10% and 8% respectively, and the doubling time was increased to 7.3 and 9.4 days respectively, all of which were significantly slower than the controls (FIG. 4b). This correlated with substantially increased survival of the host (FIG. 4c). Interestingly, the presence of the gp100 epitope in the vaccine did relatively little to improve the outcome. One mouse in each group cleared its tumor (FIG. 4b) and the average daily tumor growth rate and tumor doubling time between WT-MCMV IT and MCMV-gp100 IT treated mice were not significantly different. Mice given MCMV-gp100 IT survived slightly longer than those treated with WT-MCMV IT (p=0.073, FIG. 4c), but the difference was not dramatic. In addition, MCMV-gp100 IT infection slowed the growth of MC38 tumors, a transplantable colon adenocarcinoma that does not express gp100 (average daily growth rate of 4% for MCMV-injected tumors compared to 8% for PBS-injected tumors, 7 days after IT injection, p=0.042, FIGS. 5a and b). These data further suggest that MCMV IT infection delays tumor growth in a manner that is largely independent of the gp100 antigen, or expression of any other tumor-associated antigen by the vaccine.

Prior MCMV Infection does not Prevent the Therapeutic Effect of IT Infection.

Pre-existing anti-viral immunity may be able to restrict the efficacy of oncolytic viruses by clearing the virus[11]. More than half of people in the United States and most people in the world are already infected with CMV[24]. Therefore, we tested whether IT infection would delay tumor growth in mice that had been infected with a wild-type strain of MCMV (MCMV-K181) 8 or 52 weeks prior to tumor implantation. Importantly, prior MCMV infection had no significant effect on the survival induced by MCMV-gp100 IT infection (FIGS. 4e and f) or the daily tumor growth rate measured after MCMV-gp100 IT infection (11% vs. 8% for MCMV immune vs. naïve animals). Thus, pre-existing MCMV-specific immunity did not limit the therapeutic benefit of MCMV IT infection.

MCMV Infects Tumor-Associated Macrophages after MCMV IT Infection.

Figure 6C:
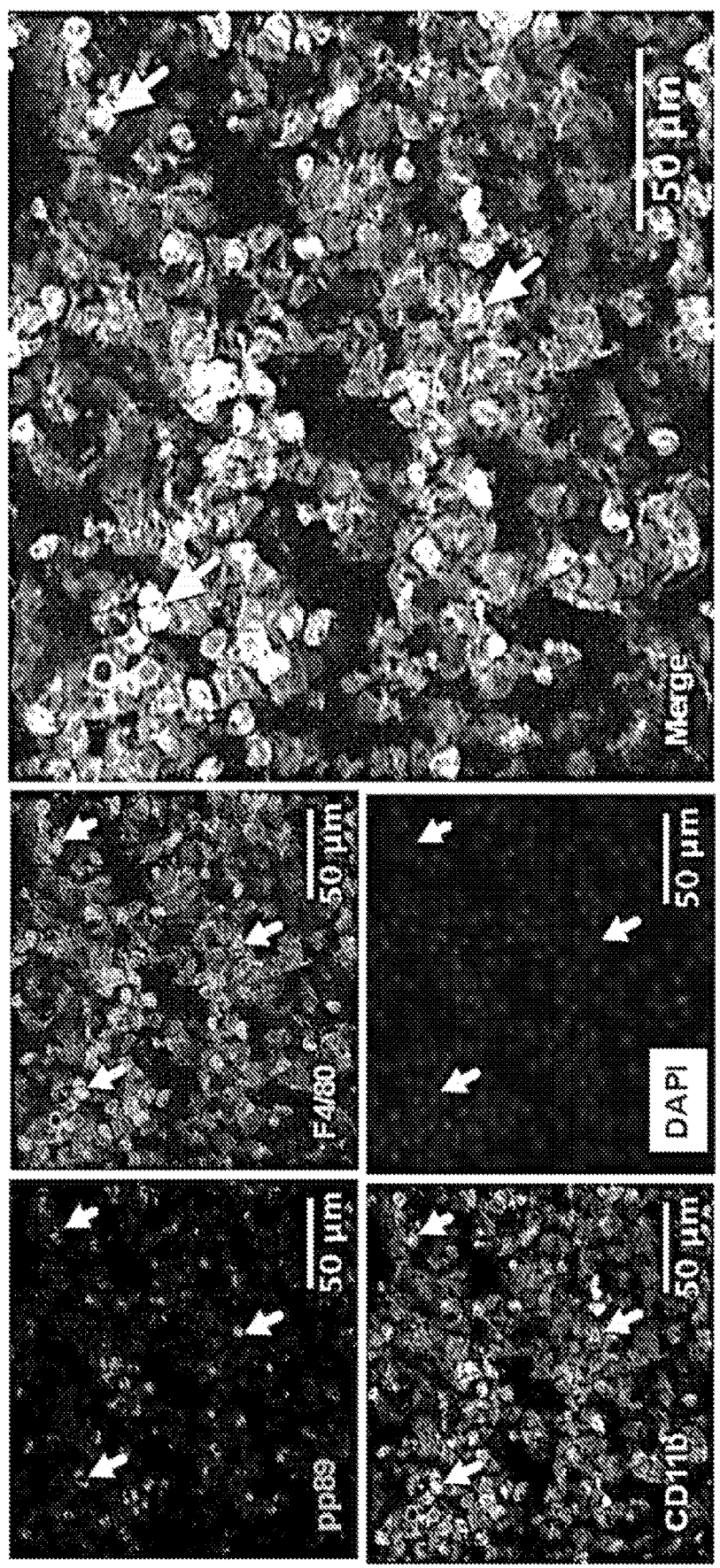

MCMV could infect and kill B16F0s (FIG. 3) and MC38s (not shown) in vitro, suggesting that it could be acting like an oncolytic virus. However, MCMV can also infect many other cells in the tumor environment including endothelial cells, fibroblasts and macrophages. To determine which cells were infected by MCMV after IT inoculation, B16F0 tumors were recovered one day after the last MCMV IT injection. Infected cells were identified histologically by the presence of nuclear-localized viral pp89, an immediate early protein (IE1) expressed by MCMV infected cells shortly after infection[40]. Viral pp89 (3rd panels from the left in "a", see panel labels) was only detected in tumors IT injected with MCMV (FIG. 6a) and co-localized with DAPI staining of the nucleus (FIG. 6a left most panels, and data not shown). Arrows indicate the same cell in each panel. Remarkably, pp89 staining was almost exclusively associated with CD45+ hematopoietic cells in the tumor (FIGS. 6a and b). In panel A, one infected cell is highlighted in the tumors from infected mice. In panel B, one infected cell (arrow pointing down and to the left) and two uninfected cells (arrows pointing up and to the left or down and to the right) are highlighted. The two highlighted uninfected cells are CD45- negative, and thus, non-hematopoietic cells. Further analyses revealed that infected cells also expressed CD11b and F4/80 (FIG. 6c). Three cells that were positive for all 3 markers are highlighted by the arrows. These data suggest that MCMV primarily infected tumor associated macrophages (TAMs) and not tumor cells, suggesting that MCMV was not acting as an oncolytic virus.

Therapeutic Efficacy of MCMV IT Infection Depends on CD8+ T Cells.

Since MCMV was likely not acting as an oncolytic virus, we wished to determine the roles of CD8+ T cells and NK cells in the therapy. To this end, CD8+ T cells and/or NK cells were depleted before the implantation of B16F0 tumors and throughout the MCMV IT therapy. Depletion of CD8+ T cells significantly reduced survival after MCMV-gp100 IT infection, while depletion of NK1.1 alone had no effect (FIGS. 7a and b). Moreover, combined depletion of CD8s and NK cells was not different from depletion of CD8+ T cells alone. Thus MCMV-IT therapy depended on CD8+ T cells to prolong survival.

Tumor-Specific T Cells are Markedly Dysfunctional within the Tumor and PD-L1 Blockade Greatly Enhances Tumor Growth Delay and Regression Induced by MCMV IT Treatment.

Figure 8A:
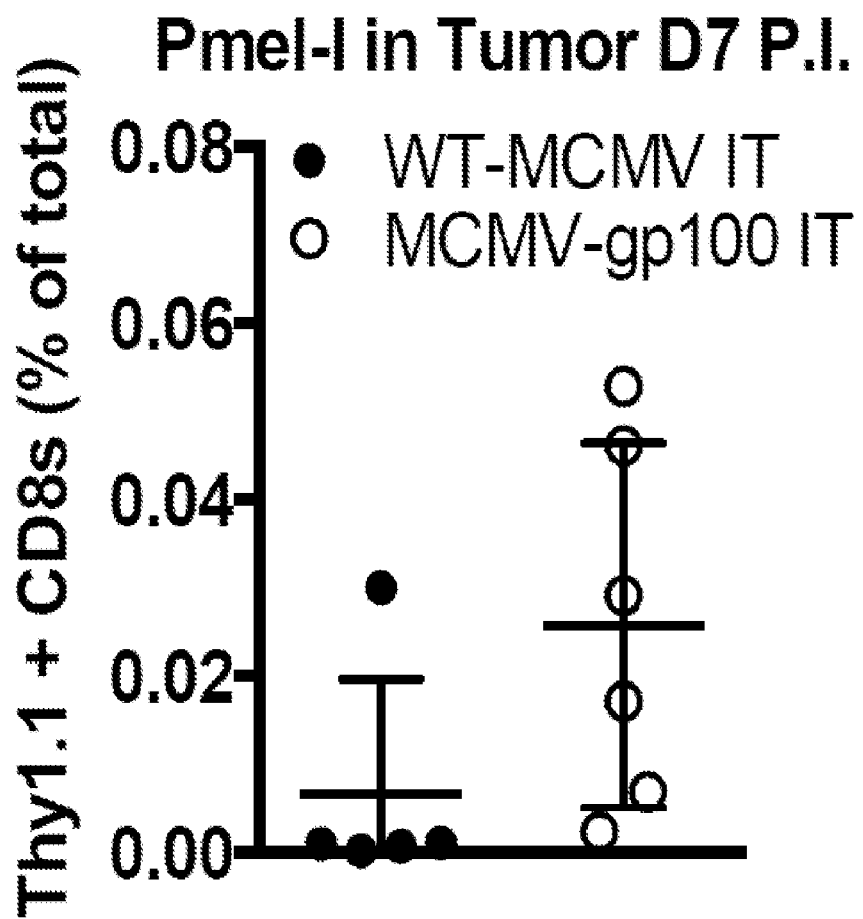
FIGS. 8 A-E depicts the tumor antigen-specific CD8+ T cells in the tumor, which were PD-1$^{hi}$ and dysfunctional after MCMV IT infection.
Figure 8B:
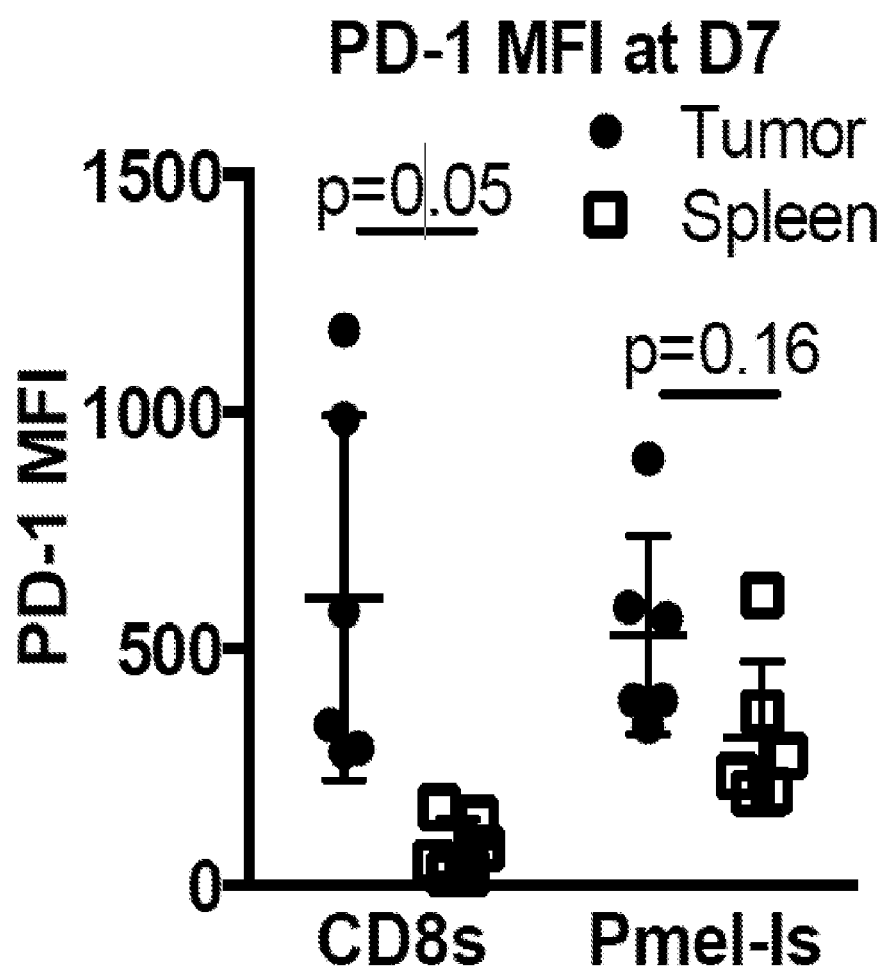
Figure 8C:
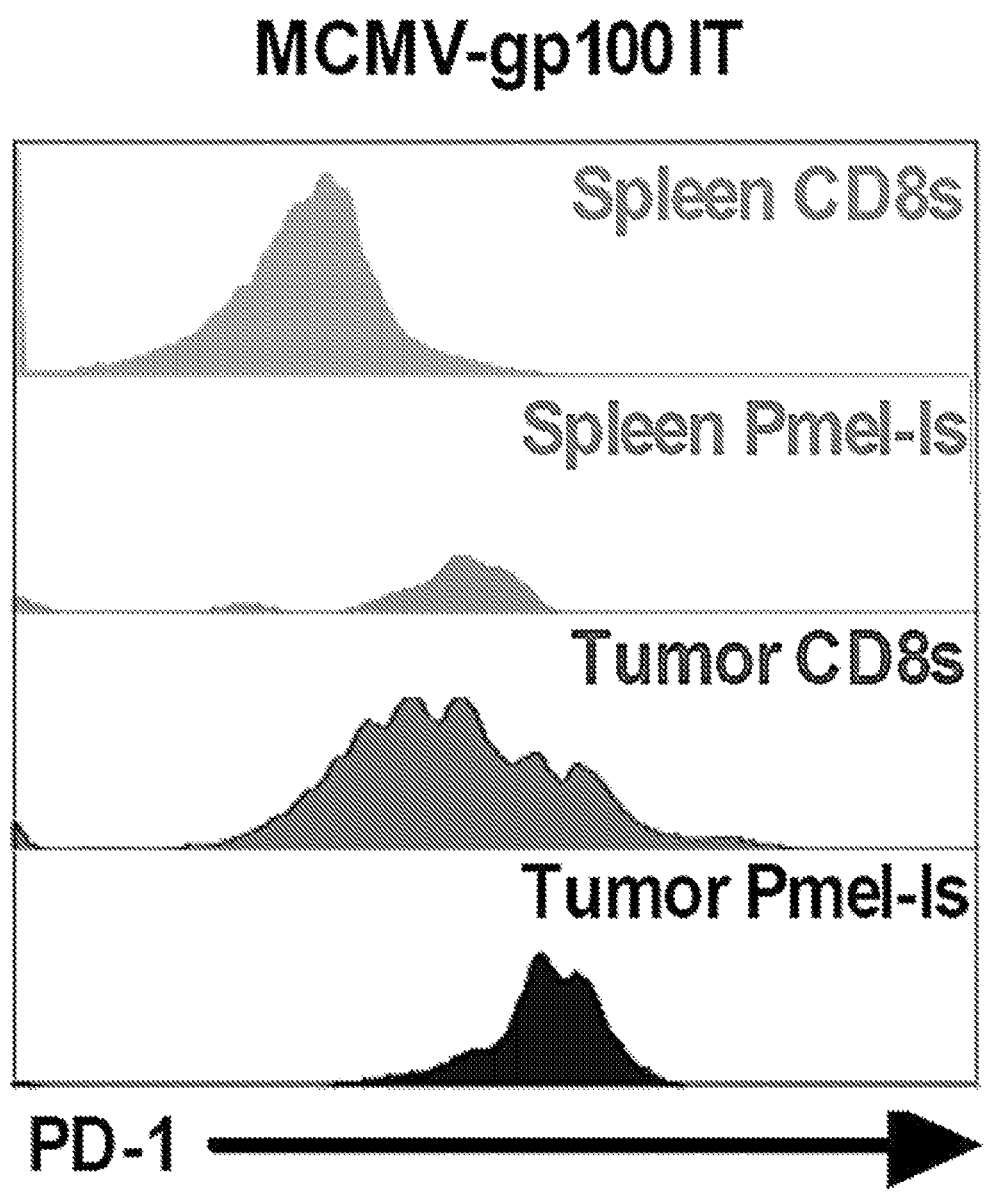
Figure 8D:
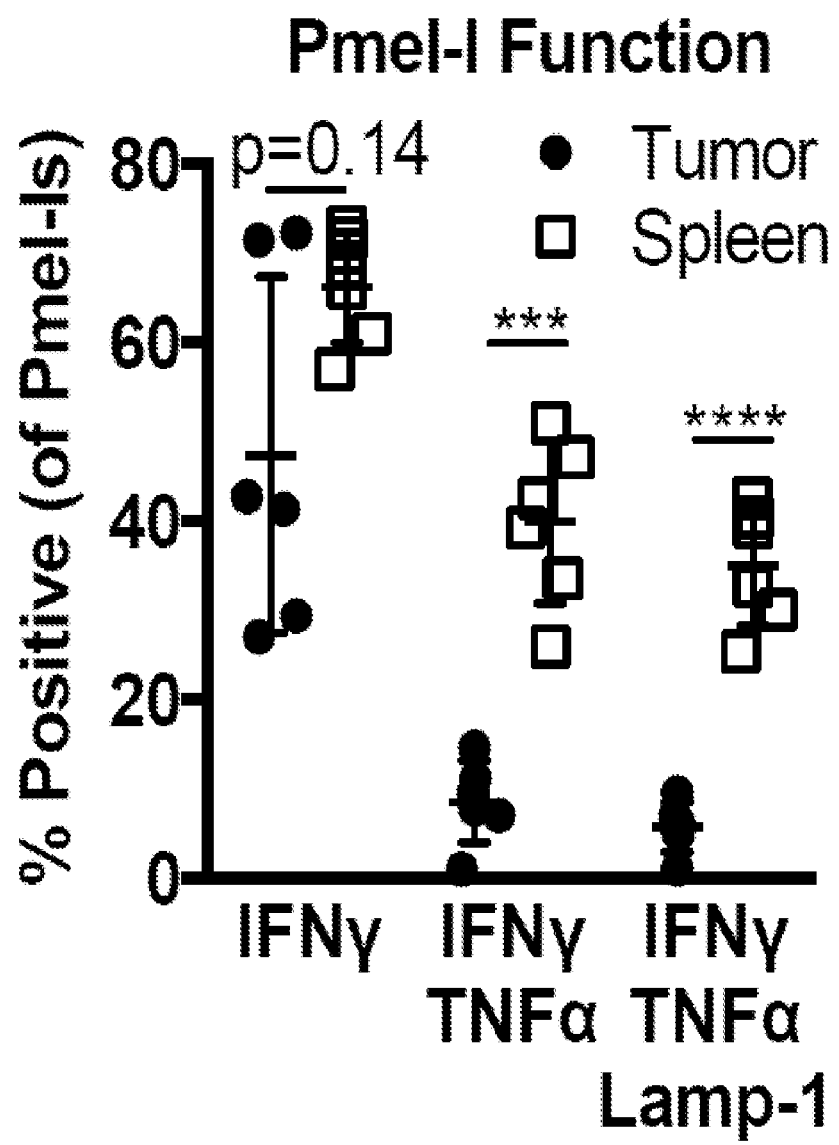
Figure 8E:
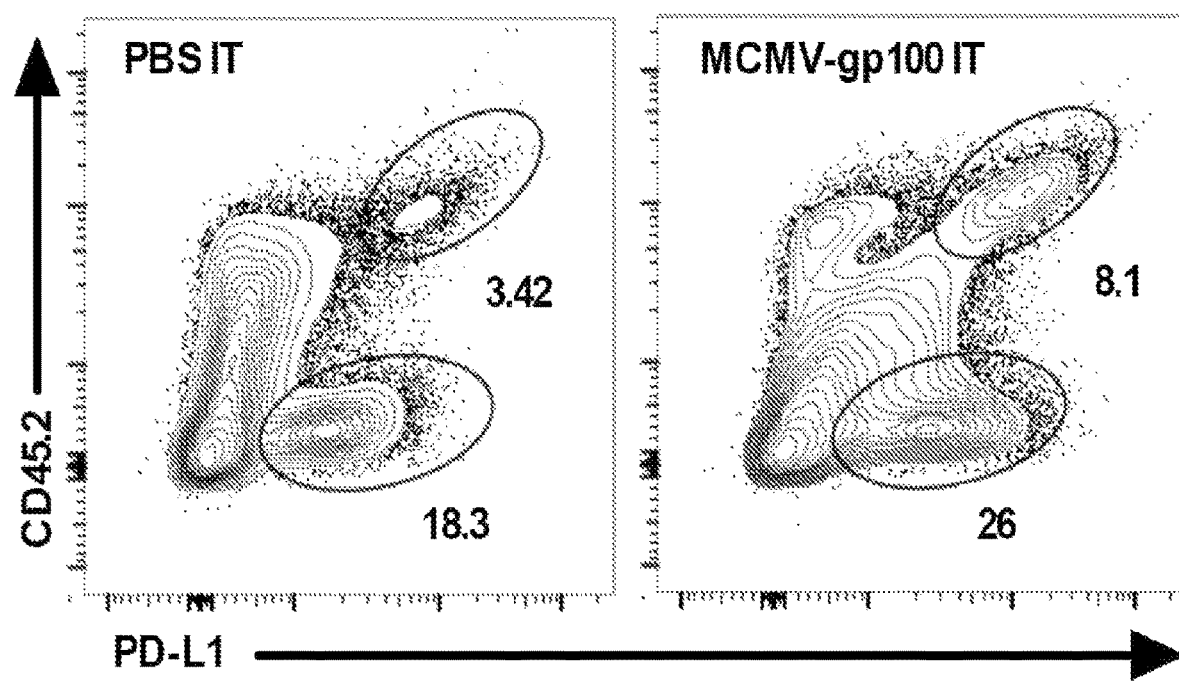

Since the MCMV IT therapy was dependent on CD8+ T cells, gp100-specific Pmel-I transgenic T cells were used to explore tumor-specific T cells after IT therapy. Naïve mice were given $10^4$ Pmel-I T cells expressing the Thy1.1. congenic marker, and B16F0 cells were implanted 1 day later. As above, recipients were IT infected when the tumors reached ~20 mm². Animals were sacrificed 7 days after the initial IT infection and tumor-infiltrating T cells were assessed. With only $10^4$ Pmel-I T cells transferred, the donor cells were undetectable in recipients infected with WT-MCMV, with the exception of one animal (FIG. 8a and data not shown). In contrast, IT infection with MCMV-gp100 induced expansion and migration of Pmel-I T cells to the tumor in all mice (FIG. 8a). Notably, these cells expressed high levels of the inhibitory molecule PD-1[3] (FIGS. 8b and c) were dysfunctional for cytokine production and degranulation compared to Pmel-I cells in the spleens of the same animals (FIG. 8d). Interestingly, tumor-specific Pmel-I T cells were slightly more functional in the tumor, and markedly more functional in the spleen after MCMV-IT therapy when compared to MCMV vaccination by the systemic intraperitoneal route (FIG. 12). PD-L1 was also detectable on cells within tumors in slightly higher levels after MCMV IT injections than PBS IT injections (FIG. 8e), although there were no differences in PD-1 expression (data not shown).

To test whether blocking PD-1/PD-L1 interactions in the tumor could improve MCMV IT therapy, WT-MCMV IT or MCMV-gp100 IT infection was combined with anti-PD-L1 antibody blockade. Remarkably, combining IT infection with PD-L1 blockade resulted in clearance of the established tumors from more than half of the mice and markedly improved overall survival regardless of which virus was used, effects that were not seen with any of these therapies alone (FIG. 9). Importantly, there was no significant survival difference between groups in which PD-L1 blockade was combined with MCMV-gp100 IT or WT-MCMV IT therapy (FIG. 9). Therefore, IT infection with MCMV synergized with anti-PD-L1 checkpoint blockade, regardless of the presence of gp100 in the vaccine.

Collectively, these data suggest that MCMV-IT therapy is improving tumor-specific T cell responses (FIG. 12) and delaying tumor growth in a manner that depends on CD8+ T cells (FIG. 7), and synergizes with PD-L1 checkpoint blockade (FIG. 9). These data suggest that MCMV-IT therapy may synergize with the PD-L1 checkpoint blockade by further improving T cell function. Thus, MCMV-IT therapy would be expected to synergize with other checkpoint blockades that promote T cell function, such as antibodies that target PD-1 and CTLA-4. However, PD-L1 can be expressed by hematopoietic cells in the tumor, including tumor-associated macrophages (FIG. 8e) and thus, it is possible that the PD-L1 blocking antibody synergizes with MCMV-IT therapy through direct interactions with tumor-infiltrating hematopoietic cells and/or by improving T cell function.

Figure 10A:
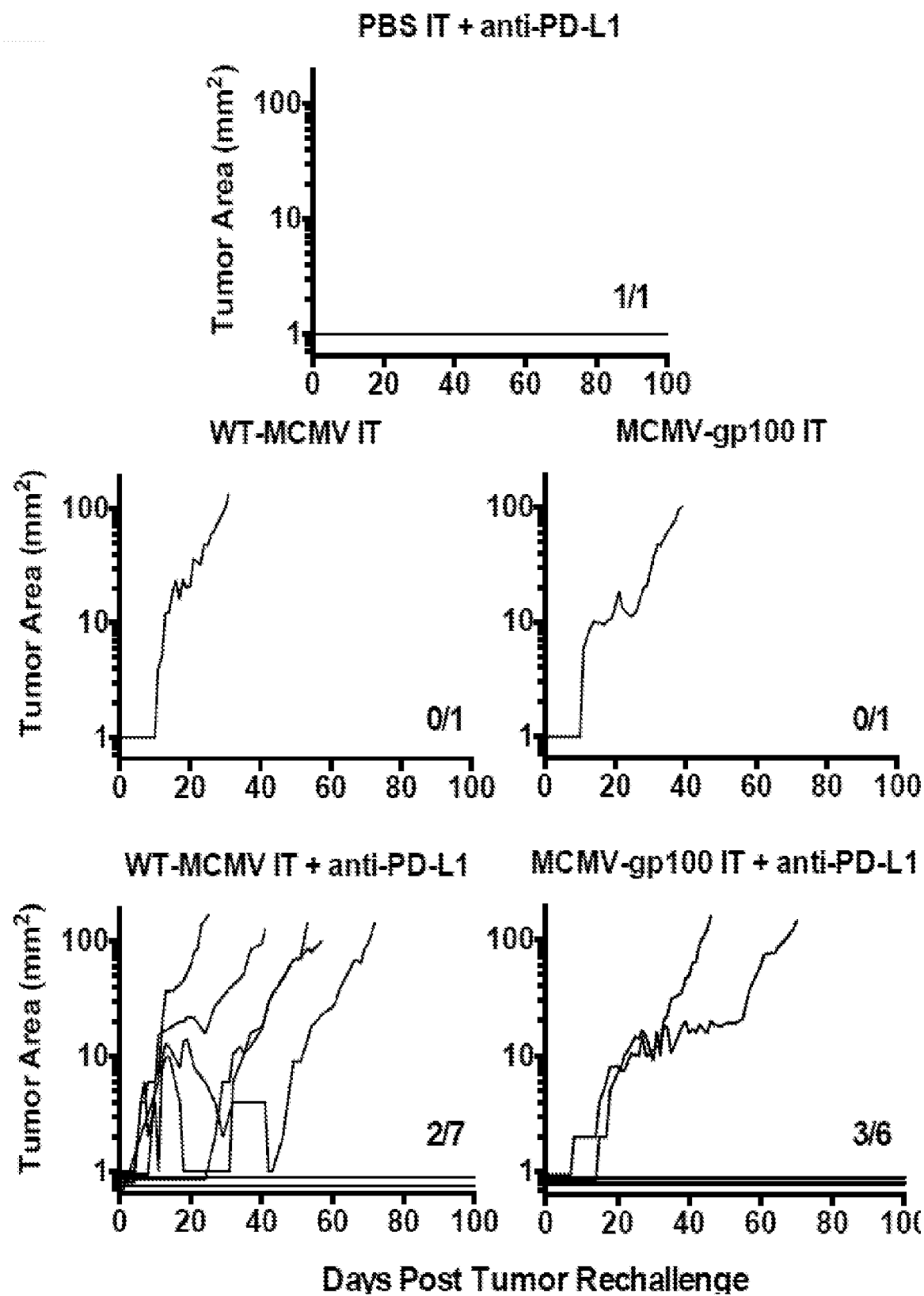
FIG. 10 depicts the primary tumor clearance after MCMV IT treatment induces resistance or rejection of secondary tumor challenges.
Figure 10B:
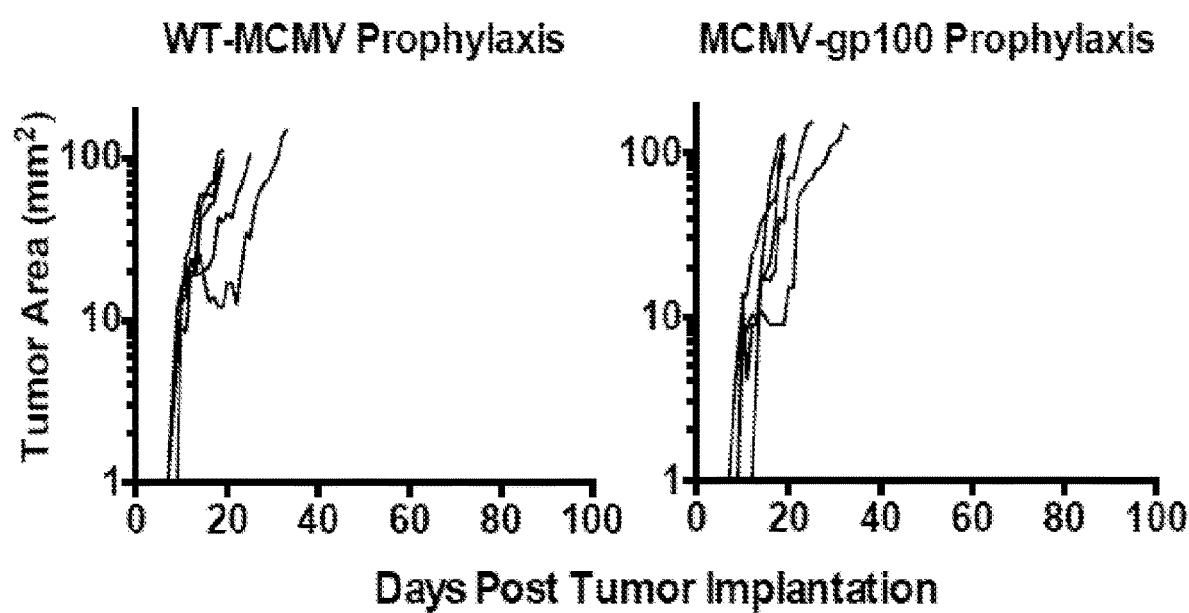
Figure 10C:
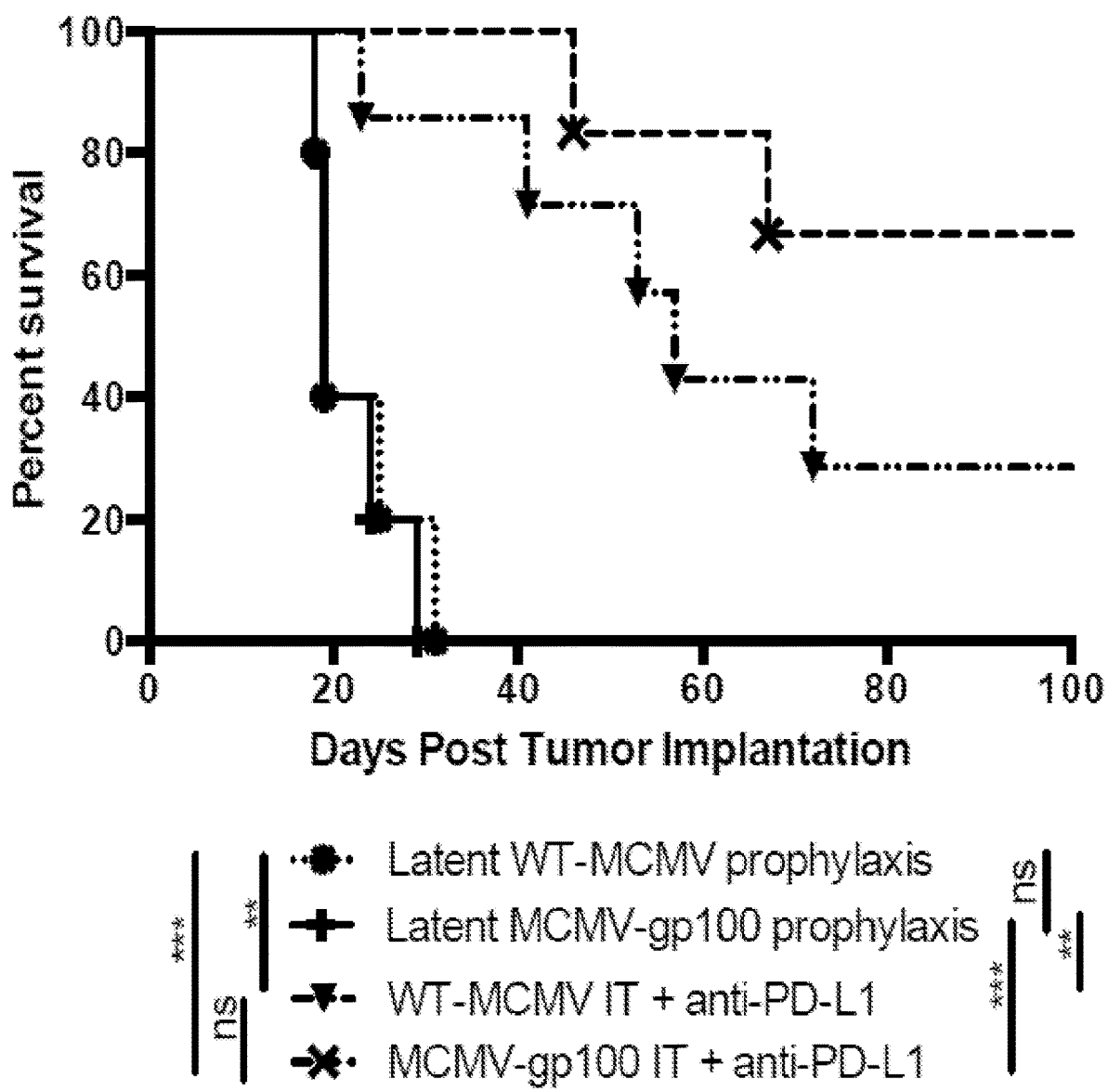
Figure 11A:
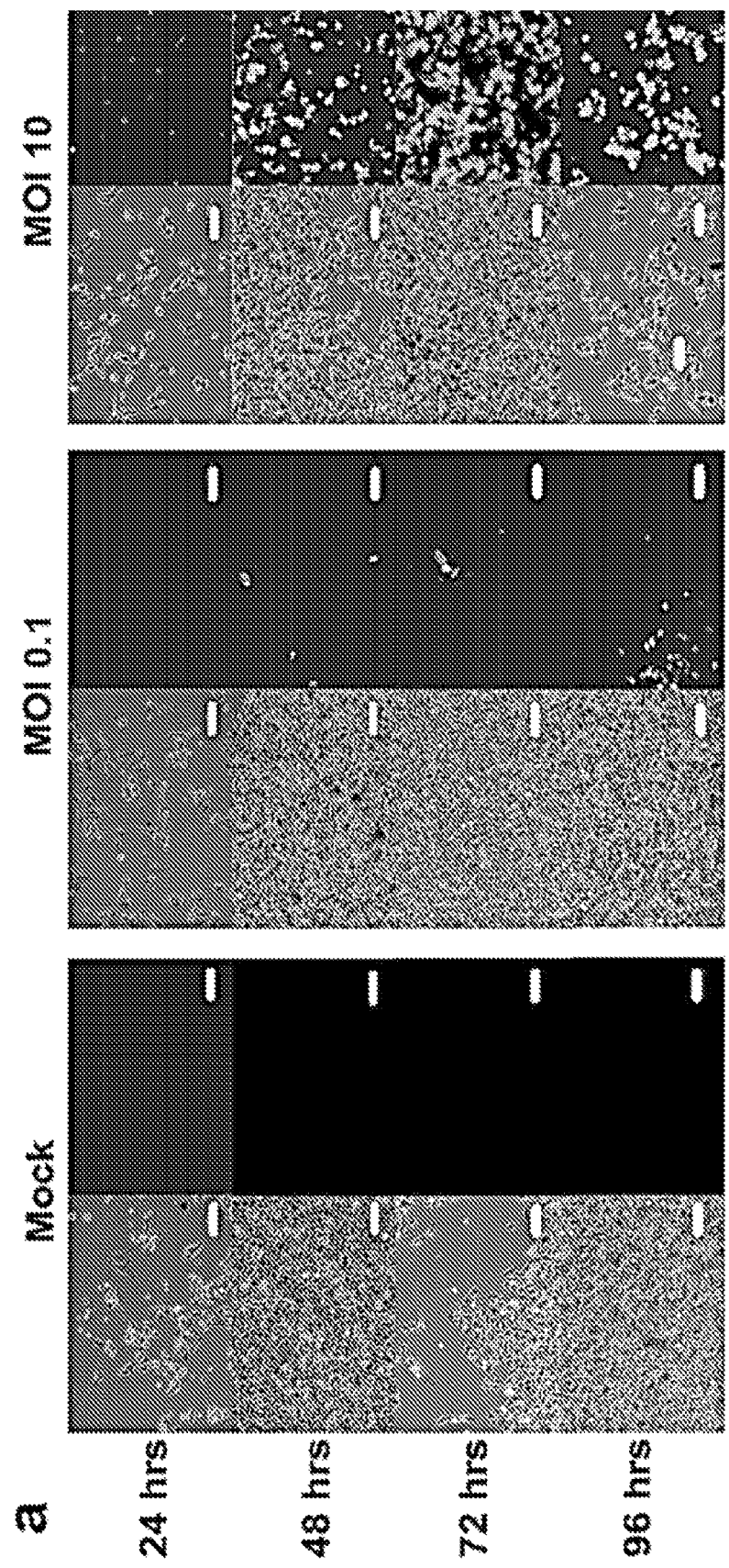
FIGS. 11 A-D depict that MCMV-gp100 is able to infect and spread in B16F0s at low and high MOIs.
Figure 11B:
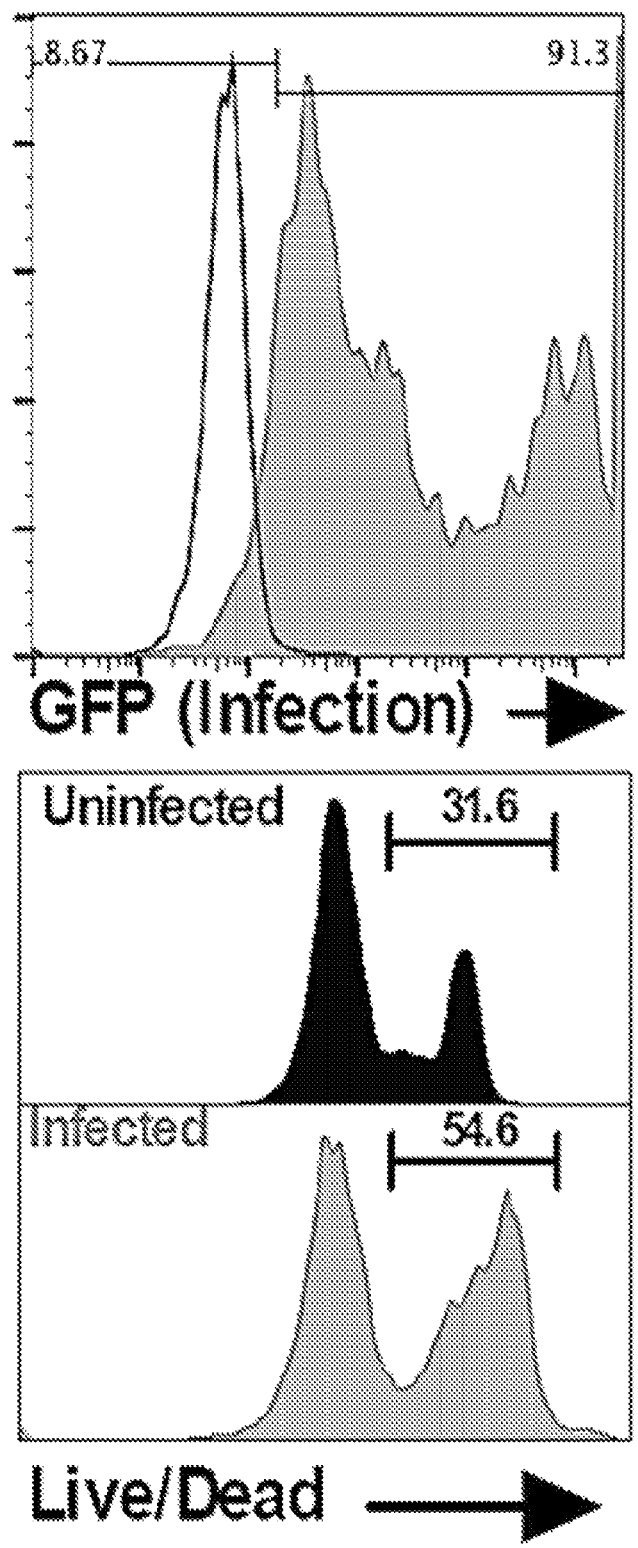
Figure 11C:
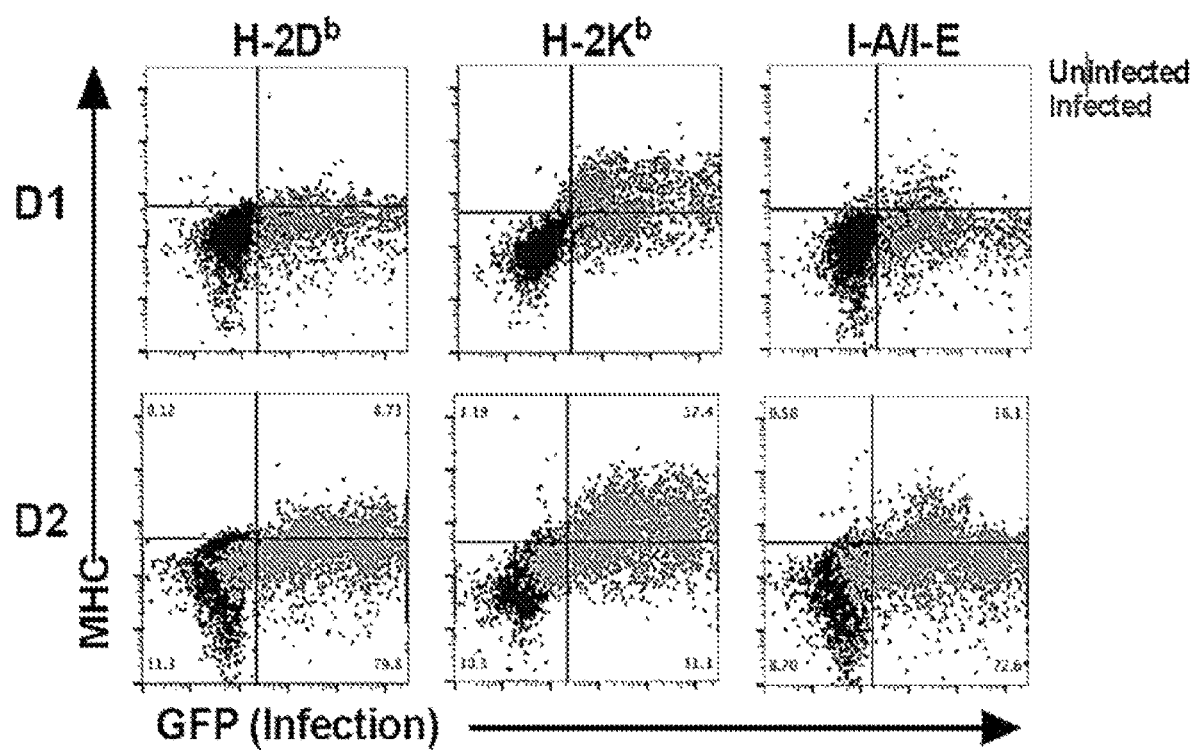
Figure 11D:
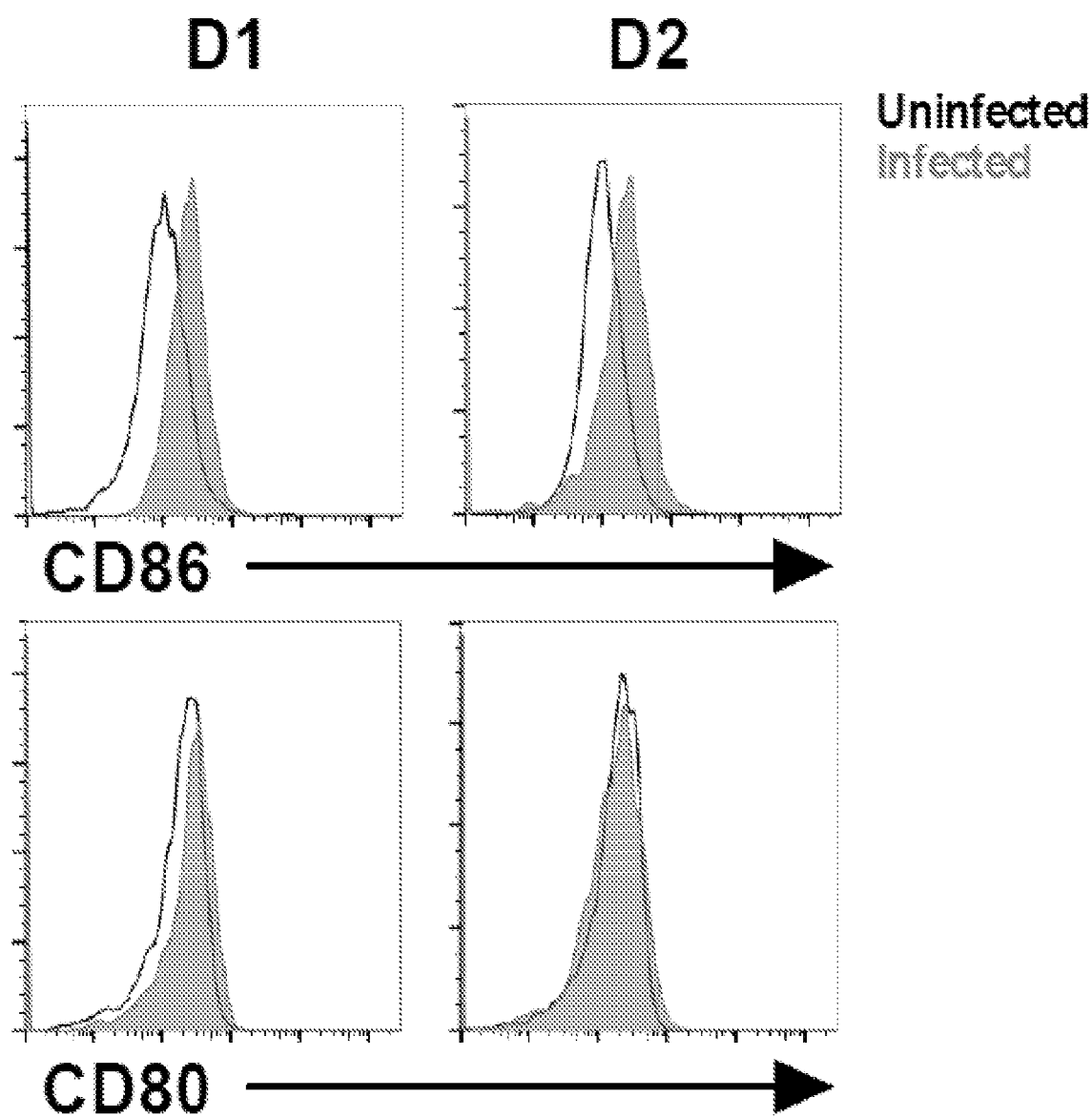

Complete Regression of Primary Tumors Results in Resistance or Rejection of Secondary B16F0 Tumor Challenges To determine whether clearance of tumors would result in protection against tumor challenge, the animals that cleared primary tumors after the various treatments described above were re-challenged with $2\times10^5$ B16F0s in the opposite flank 50-60 days after initial tumor implantation and at least 2 weeks after primary tumor clearance. Secondary tumors completely failed to grow in 5 of 15 mice that received any type of IT MCMV infection (FIG. 10a, observed for >100 days). Moreover, in 2 of the cases that we found tumor growth, the challenge tumor did not appear until 27 (WT-MCMV IT+anti-PD-L1) or 140 days (MCMV-gp100 IT+anti-PD-L1, data not shown) post challenge. The one mouse that cleared its primary tumor after anti-PD-L1 treatment alone also rejected the secondary tumor (FIG. 10a). Regardless of whether the primary tumor had been cleared after treatment with WT-MCMV IT+anti-PD-L1 or MCMV-gp100 IT+anti-PD-L1, there was no significant difference in the survival of these mice upon re-challenge (FIG. 10c). Nevertheless, to determine whether some of this enhanced tumor resistance could be attributed to the fact that the challenged mice had been previously infected with MCMV-gp100, we implanted B16F0s into animals that had been infected with WT-MCMV or MCMV-gp100 by the IP route>100 days previously, but were not previously given tumors. Even though large gp100-specific T cell populations were evident after vaccination with MCMV-gp100 (FIG. 1c), there was little effect on tumor growth or survival in these mice compared to mice infected with WT-MCMV (FIGS. 10b and c) and no marked growth delay or tumor resistance, unlike mice that had previously cleared a tumor (FIG. 10a). Importantly, depletion of $CD8^+$ T cells more than 90 days after re-challenge did not enable late tumor growth in mice that rejected the challenge tumor (data not shown), suggesting that either long-term protection was $CD8^+$ T cell independent or the animals were cured of their tumors.

These data strongly imply that IT MCMV infection combined with PD-L1 blockade induced broad immunity to the B16F0 melanoma, subsequently preventing tumor growth at a distal site, independent of the gp100 antigen encoded in the viral genome or large numbers of circulating gp100-specific T cells. Collectively, these data suggest that MCMV infects TAMs after IT infection, resulting in an unexpectedly potent, $CD8^+$ T cell-dependent, anti-tumor effect that can act synergistically with blockade of the PD-1 pathway to clear established tumors and promote systemic anti-tumor immunity.

Discussion

Direct modulation of the tumor microenvironment can markedly improve both local and systemic anti-tumor effects. Recent evidence suggests that IT administration of several different therapies induces better anti-tumor responses in animals, many times correlating with effects on distant tumors[6,7]. Thus, IT therapies are currently being explored for both cutaneous and non-cutaneous cancers[7]. Our data show that systemic vaccination with MCMV-gp100 by the IP and ID routes induced migration of antigen-specific $CD8^+$ T cells into tumor tissue, but relatively poor anti-tumor effects (FIG. 2). However, IT infection with MCMV induced marked tumor growth delay and prolonged survival in both B16F0 (melanoma) and MC38 (colon adenocarcinoma) models (FIG. 4 and FIG. 5). Remarkably, this was true even for MCMV lacking expression of tumor-associated antigens or in mice that were already infected with MCMV (FIG. 4 and FIG. 5).

MCMV does not fit the typical definition of an oncolytic virus. Oncolytic viruses are typically defined by their ability to replicate rapidly and somewhat selectively in tumor cells, inducing tumor cell death and subsequent anti-tumor and anti-viral immune responses[41,42]. While MCMV could infect and kill B16F0s in culture (FIGS. 3 and 11), it only seemed to infect tumor-associated macrophages (TAMs) in vivo (FIG. 6), suggesting that IT therapy is not working through direct tumor lysis. TAMs are associated with tumor progression by inducing a pro-angiogenic environment and suppressing anti-tumor immune responses[43,44]. CMV infects monocytes and macrophages, inducing monocyte migration, tissue entry, and differentiation into macrophages[45,46]. CMV infection of macrophages shifts them to an immune stimulatory phenotype by inducing up-regulation of TLRs and increasing Th1 cytokine production[46-48], subsequently leading to increased T cell proliferation[47]. Moreover, it is possible that MCMV infection of TAMs could decrease the macrophage production of pro-angiogenic factors, such as VEGF and ARG1, decreasing blood flow to tumors and slowing growth[43,44]. All these possibilities must addressed in future studies as possible mechanisms for MCMV IT therapy. It is worth noting that the MCMV immediate early protein pp89 (IE1), which is expressed early after infection, may have different expression levels in different cell types. Thus it is possible that we only detected a subset of infected cells in the tumor that expressed pp89 at high levels, and that MCMV is still infecting the tumor cells themselves, or the tumor vasculature[49]. This caveat aside, our data suggest that MCMV IT therapy works by altering TAMs and their interaction with tumors.

It is also worth noting that CMV almost certainly affects the tumor microenvironment beyond the cells that are directly infected. Contact with viral particles or gene-products likely triggers cell signaling and gene expression by cells in the tumor environment, regardless of infection. For example, CMV glycoproteins have been described to activate Toll-like receptor 2 (TLR-2)[50,51] and CMV particles can activate the epidermal growth factor receptor (EGFR)[52-54], leading to an array of cellular responses. In addition, MCMV is a potent stimulator of NK cells and γδ-T cells[39,55], both of which might have anti-tumor effects. Therefore, infection of tumor associated macrophages may provide a therapeutic benefit, but may not be required for the therapeutic effect or the synergy with additional immune therapies.

In B6 mice, NK cells expressing Ly49H are specifically expanded in response to the viral m157 protein[39]. However, this population was not expanded in the tumors of mice vaccinated with MCMV by the IT route (not shown). Rather, the tumor-infiltrating NK cells were largely Ly49H−, KLRG-1+, possibly suggesting that tumor-localized NK cells were activated in response to the tumor. Despite this, NK cell depletion had no effect on the MCMV IT therapy (FIG. 7), suggesting NK cells were not important for the therapeutic outcome. Additional experiments will be needed to explore the impact of MCMV on other cells in the tumor and the tumor environment as a whole, after injection of live or inactivated viral particles. Thus, the use of live, virulent, attenuated or killed virus vaccines may all be effective alone or in combination with immune checkpoint inhibitors.

Ultimately, improved survival after MCMV IT therapy depended on $CD8^+$ T cells but not NK cells (FIG. 7). Interestingly however, IT injection of MCMV did not increase $CD8^+$ T cell frequencies above that induced by IP or ID infections. Although our data show that gp100-specific Pmel-I T cells were markedly dysfunctional in the tumor after MCMV-gp100 IT vaccination (FIG. 8), our data suggest that Pmel-I function was actually improved by IT therapy compared to MCMV-gp100 IP vaccination, especially in the spleen (FIG. 12). Moreover, blockade of the PD-1/PD-L1 pathway was synergistic with IT MCMV infection, leading to clearance of tumors from over half of the mice (FIG. 9). This tumor clearance correlated with systemic anti-tumor immunity that could resist a secondary tumor challenge in the opposite flank, and was seemingly independent of the gp100 epitope encoded in the viral genome as well as gp100-specific T-cells induced by prophylactic vaccination (FIG. 10). Thus, we propose that MCMV IT infection of TAMs within B16F0 tumors, in combination with blockade of the PD-1 pathway, improved the endogenous anti-tumor immunity.

Our data indicated that IP vaccination alone was ineffective for subcutaneous B16 tumors, which contrasts with recent work by Qiu and colleagues, who found that IP vaccination with a similar MCMV-gp100 vector was sufficient to delay the growth of lung nodules after IV injection of B16 melanoma cells[32]. We favor the possibility that the different outcomes reflect the differences in tumor location. For example, gp100-specific CD8$^+$ T cells may more easily traffic to lung tumors as these nodules will be well exposed to the blood supply[56] and we have shown that many circulating MCMV-specific T cells are localized to the lung vasculature after IP infection[28]. Moreover, after IP infection, MCMV may more readily infect macrophages in lung nodules as compared to subcutaneous nodules. Alternatively, it is possible that tumors growing in each location depend on different immune inhibitory mechanisms that are more or less easily overcome by MCMV-driven T cells. Finally, it is notable that the MCMV-gp100 vaccine used by Qiu and colleagues expressed a variant of the gp100 antigen that differed by 2 amino acids from the native sequence (gp100$^{E25K, S27P}$), whereas the epitope used in our study differed by only one amino acid (gp100$^{S27P}$), a difference that could, in theory, have a substantial impact on the efficacy or function of gp100-specific T cells. Future work will be required to test these ideas.

All in all, we are the first to show that MCMV may have superior therapeutic efficacy for cutaneous melanomas after direct intra-tumoral injections, and that this route of vaccination can synergize with immune checkpoint blockades to clear tumors and induce protection against distal tumors, without virally encoded tumor antigens. This study builds on recent data suggesting that CMV may be an effective anti-tumor therapy and suggests that the route of infection and tumor location may be critical factors in defining the efficacy of this platform.

REFERENCES

1 Klebanoff, C. A., Acquavella, N., Yu, Z. & Restifo, N. P. Therapeutic cancer vaccines: are we there yet? *Immunol Rev* 239, 27-44, doi:10.1111/j.1600-065X.2010.00979.x (2011).
2 Schreiber, R. D., Old, L. J. & Smyth, M. J. Cancer immunoediting: integrating immunity's roles in cancer suppression and promotion. *Science* 331, 1565-1570, doi: 10.1126/science.1203486 (2011).
3 Wherry, E. J. T cell exhaustion. *Nature Immunology* 131, 492-499, doi:10.1038/ni.2035 (2011).
4 Hailemichael, Y. & Overwijk, W. W. Cancer vaccines: Trafficking of tumor-specific T cells to tumor after therapeutic vaccination. *Int J Biochem Cell Biol* 53, 46-50, doi:10.1016/j.biocel.2014.04.019 (2014).
5 Azimi, F. et al. Tumor-infiltrating lymphocyte grade is an independent predictor of sentinel lymph node status and survival in patients with cutaneous melanoma. *J Clin Oncol* 30, 2678-2683, doi:10.1200/JCO.2011.37.8539 (2012).
6 Singh, M. & Overwijk, W. W. Intratumoral immunotherapy for melanoma. *Cancer Immunol Immunother* 64, 911-921, doi:10.1007/s00262-015-1727-z (2015).
7 Marabelle, A., Kohrt, H., Caux, C. & Levy, R. Intratumoral immunization: a new paradigm for cancer therapy. *Clin Cancer Res* 20, 1747-1756, doi:10.1158/1078-0432.CCR-13-2116 (2014).
8 Miest, T. S. & Cattaneo, R. New viruses for cancer therapy: meeting clinical needs. *Nature reviews. Microbiology* 12, 23-34, doi:10.1038/nrmicro3140 (2014).
9 Andtbacka, R. H. et al. Talimogene Laherparepvec Improves Durable Response Rate in Patients With Advanced Melanoma. *J Clin Oncol*, doi:10.1200/JCO.2014.58.3377 (2015).
10 FDA approves first-of-its-kind product for the treatment of melanoma, fda.gov/NewsEvents/Newsroom/PressAnnouncements/ucm469571.htm (2015).
11 Barlett, D. L. et al. Oncolytic viruses as therapeutic cancer vaccines. *Molecular Cancer* 13 (2013).
12 Heo, J. et al. Randomized dose-finding clinical trial of oncolytic immunotherapeutic vaccinia JX-594 in liver cancer. *Nat Med* 19, 329-336, doi:10.1038/nm.3089 (2013).
13 Hemminki, O. et al. Immunological data from cancer patients treated with Ad5/3-E2F-Δ24-GMCSF suggests utility for tumor immunotherapy. *Oncotarget* 6, 4467-4481 (2015).
14 Woller, N., Gurlevik, E., Ureche, C. I., Schumacher, A. & Kuhnel, F. Oncolytic viruses as anticancer vaccines. *Front Oncol* 4, 188, doi:10.3389/fonc.2014.00188 (2014).
15 Holtappels, R., Pahl-Seibert, M.-F., Thomas, D. & Reddehase, M. J. Enrichment of Immediate-Early 1 (m123/pp89) Peptide-Specific CD8 T Cells in a Pulmonary CD62Llo Memory-Effector Cell Pool during Latent Murine Cytomegalovirus Infection of the Lungs. *Journal of Virolody* 74, 11495-11503 (2000).
16 Holtappels, R. et al. Processing and Presentation of Murine Cytomegalovirus pORFm164-Derived Peptide in Fibroblasts in the Face of All Viral Immunosubversive Early Gene Functions. *Journal of Virology* 76, 6044-6053, doi:10.1128/jvi.76.12.6044-6053.2002 (2002).
17 Komatsu, H., Sierro, S., V. Cuero, A. & Klenerman, P. Population analysis of antiviral T cell responses using MEW class I-peptide tetramers. *Clinical and Experimental Immunology* 134, 9-12, doi:10.1046/j.1365-2249.2003.02266.x (2003).
18 Karrer, U. et al. Expansion of Protective CD8+ T-Cell Responses Driven by Recombinant Cytomegaloviruses. *Journal of Virology* 78, 2255-2264, doi:10.1128/jvi.78.5.2255-2264.2004 (2004).
19 Munks, M. W. et al. Genome-Wide Analysis Reveals a Highly Diverse CD8 T Cell Response to Murine Cytomegalovirus. *Journal of immunology* 176, 3760-3766 (2006).
20 Borst, E. M., Benkartek, C. & Messerle, M. Use of bacterial artificial chromosomes in generating targeted mutations in human and mouse cytomegaloviruses. *Curr Protoc Immunol*. (2007).
21 Hansen, S. G. et al. Effector memory T cell responses are associated with protection of rhesus monkeys from mucosal simian immunodeficiency virus challenge. *Nat Med* 15, 293-299, doi:10.1038/nm.1935 (2009).

22. Hansen, S. G. et al. Profound early control of highly pathogenic SIV by an effector memory T-cell vaccine. *Nature* 473, 523-527, doi:10.1038/nature10003 (2011).
23. Hansen, S. G. et al. Immune clearance of highly pathogenic SIV infection. *Nature* 502, 100-104, doi:10.1038/nature12519 (2013).
24. Bate, S. L., Dollard, S. C. & Cannon, M. J. Cytomegalovirus seroprevalence in the United States: the national health and nutrition examination surveys, 1988-2004. *Clin Infect Dis* 50, 1439-1447, doi:10.1086/652438 (2010).
25. Hansen, S. G. et al. Evasion of CD8+ T cells is critical for superinfection by cytomegalovirus. *Science* 328, 102-106, doi:10.1126/science.1185350 (2010).
26. Hertoghs, K. M. et al. Molecular profiling of cytomegalovirus-induced human CD8+ T cell differentiation. *J Clin Invest* 120, 4077-4090, doi:10.1172/JCI42758 (2010).
27. Sierro, S., Rothkopf, R. & Klenerman, P. Evolution of diverse antiviral CD8+ T cell populations after murine cytomegalovirus infection. *European journal of immunology* 35, 1113-1123, doi:10.1002/eji.200425534 (2005).
28. Smith, C. J., Turula, H. & Snyder, C. M. Systemic hematogenous maintenance of memory inflation by MCMV infection. *PLoS Pathog* 10, e1004233, doi:10.1371/journal.ppat.1004233 (2014).
29. Smith, C. J., Caldeira-Dantas, S., Turula, H. & Snyder, C. M. Murine CMV Infection Induces the Continuous Production of Mucosal Resident T Cells. *Cell Rep* 13, 1137-1148, doi:10.1016/j.celrep.2015.09.076 (2015).
30. Klyushnenkova, E. N. et al. A cytomegalovirus-based vaccine expressing a single tumor-specific CD8+ T-cell epitope delays tumor growth in a murine model of prostate cancer. *J Immunother* 35, 390-399, doi:10.1097/CJI.0b013e3182585d50 (2012).
31. Xu, G., Smith, T., Grey, F. & Hill, A. B. Cytomegalovirus-based cancer vaccines expressing TRP2 induce rejection of melanoma in mice. *Biochem Biophys Res Commun* 437, 287-291, doi:10.1016/j.bbrc.2013.06.068 (2013).
32. Qiu, Z. et al. Cytomegalovirus based vaccine expressing a modified tumor antigen induces potent tumor-specific CD8+ T cell response and protects mice from melanoma. *Cancer Immunology Research* 3, 1-11, doi:10.1158/2326-6066.cir-14-0044 (2015).
33. van Stipdonk, M. J. et al. Design of agonistic altered peptides for the robust induction of CTL directed towards H-2db in complex with the melanoma-associated epitope gp100. *Cancer Res* 69, 7784-7792, doi:10.1158/0008-5472.CAN-09-1724 (2009).
34. Dekhtiarenko, I., Jarvis, M. A., Ruzsics, Z. & Cicin-Sain, L. The context of gene expression defines the immunodominance hierarchy of cytomegalovirus antigens. *Journal of immunology* 190, 3399-3409, doi:10.4049/jimmunol.1203173 (2013).
35. Farrington, L. A., Smith, T. A., Grey, F., Hill, A. B. & Snyder, C. M. Competition for antigen at the level of the APC is a major determinant of immunodominance during memory inflation in murine cytomegalovirus infection. *Journal of immunology* 190, 3410-3416, doi:10.4049/jimmunol.1203151 (2013).
36. Turula, H., Smith, C. J., Grey, F., Zurbach, K. A. & Snyder, C. M. Competition between T cells maintains clonal dominance during memory inflation induced by MCMV. *European journal of immunology* 43, 1252-1263, doi:10.1002/eji.201242940 (2013).
37. Wakim, L. M., Jones, C. M., Gebhardt, T., Preston, C. M. & Carbone, F. R. CD8(+) T-cell attenuation of cutaneous herpes simplex virus infection reduces the average viral copy number of the ensuing latent infection. *Immunol Cell Biol* 86, 666-675, doi:10.1038/icb.2008.47 (2008).
38. Liu, L. et al. Epidermal injury and infection during poxvirus immunization is crucial for the generation of highly protective T cell-mediated immunity. *Nat Med* 16, 224-227, doi:10.1038/nm.2078 (2010).
39. Lanier, L. L. Evolutionary struggles between NK cells and viruses. *Nature reviews. Immunology* 8, 259-268, doi:10.1038/nri2276 (2008).
40. Keil, G. M., Ebeling-Keil, A. & Koszinowski, U. H. Immediate-Early Genes of Murine Cytomegalovirus: Location, Transcripts, and Translation Products. *Journal of Virology* 61, 526-533 (1987).
41. Larocca, C. & Schlom, J. Viral vector-based therapeutic cancer vaccines. *Cancer J* 17, 359-371, doi:10.1097/PPO.0b013e3182325e63 (2011).
42. Lichty, B. D., Breitbach, C. J., Stojdl, D. F. & Bell, J. C. Going viral with cancer immunotherapy. *Nature reviews. Cancer* 14, 559-567, doi:10.1038/nrc3770 (2014).
43. Gabrilovich, D. I., Ostrand-Rosenberg, S. & Bronte, V. Coordinated regulation of myeloid cells by tumours. *Nature reviews. Immunology* 12, 253-268, doi:10.1038/nri3175 (2012).
44. Chanmee, T., Ontong, P., Konno, K. & Itano, N. Tumor-associated macrophages as major players in the tumor microenvironment. *Cancers (Basel)* 6, 1670-1690, doi:10.3390/cancers6031670 (2014).
45. Daley-Bauer, L. P., Roback, L. J., Wynn, G. M. & Mocarski, E. S. Cytomegalovirus hijacks CX3CR1(hi) patrolling monocytes as immune-privileged vehicles for dissemination in mice. *Cell host & microbe* 15, 351-362, doi:10.1016/j.chom.2014.02.002 (2014).
46. Smith, M. S., Bentz, G. L., Alexander, J. S. & Yurochko, A. D. Human Cytomegalovirus Induces Monocyte Differentiation and Migration as a Strategy for Dissemination and Persistence. *Journal of Virology* 78, 4444-4453, doi:10.1128/jvi.78.9.4444-4453.2004 (2004).
47. Bayer, C. et al. Human cytomegalovirus infection of M1 and M2 macrophages triggers inflammation and autologous T-cell proliferation. *J Virol* 87, 67-79, doi:10.1128/JVI.01585-12 (2013).
48. Gary Chan1, E. R. B.-S., M. Shane Smith2, Patrick M. Smith1, and Andrew D. Yurochko. Transcriptome Analysis Reveals Human Cytomegalovirus Reprograms Monocyte Differentiation Towards a M1 Macrophage. (2008).
49. van de Berg, P. J., Yong, S. L., Remmerswaal, E. B., van Lier, R. A. & ten Berge, I. J. Cytomegalovirus-induced effector T cells cause endothelial cell damage. *Clin Vaccine Immunol* 19, 772-779, doi:10.1128/CVI.00011-12 (2012).
50. Szomolanyi-Tsuda, E., Liang, X., Welsh, R. M., Kurt-Jones, E. A. & Finberg, R. W. Role for TLR2 in NK cell-mediated control of murine cytomegalovirus in vivo. *J Virol* 80, 4286-4291, doi:10.1128/JVI.80.9.4286-4291.2006 (2006).
51. Boehme, K. W., Guerrero, M. & Compton, T. Human Cytomegalovirus Envelope Glycoproteins B and H Are Necessary for TLR2 Activation in Permissive Cells. *The Journal of Immunology* 177, 7094-7102, doi:10.4049/jimmunol.177.10.7094 (2006).
52. Yamazaki, D. et al. WAVE2 is required for directed cell migration and cardiovascular development. *Nature* 424, 452-456, doi:10.1038/nature01770 (2003).
53. Chan, G., Nogalski, M. T. & Yurochko, A. D. Activation of EGFR on monocytes is required for human cytomegalovirus entry and mediates cellular motility. *Proc Natl Acad Sci USA* 106, 22369-22374, doi:10.1073/pnas.0908787106 (2009).

54 Bentz, G. L. & Yurochko, A. D. Human CMV infection of endothelial cells induces an angiogenic response through viral binding to EGF receptor and beta1 and beta3 integrins. *Proc Natl Acad Sci USA* 105, 5531-5536, doi:10.1073/pnas.0800037105 (2008).

55 Sell, S. et al. Control of murine cytomegalovirus infection by gammadelta T cells. *PLoS Pathog* 11, e1004481, doi:10.1371/journal.ppat.1004481 (2015).

56 Nannmark, U. et al. Microvessel Origin and Distribution in Pulmonary Metastases of B16 Melanoma: Implication for Adoptive Immunotherapy'. *Cancer Research* 55, 4627-4632 (1995).

57 Wagner, M., Jonjic, S., Koszinowski, U. H. & Messerle, M. Systematic Excision of Vector Sequences from the BAC-Cloned Herpesvirus Genome during Virus Reconstitution. *Journal of Virology* 73, 7056-7060 (1999).

58 Zurbach, K. A., Moghbeli, T. & Snyder, C. M. Resolving the titer of murine cytomegalovirus by plaque assay using the M2-10B4 cell line and a low viscosity overlay. *Virol J* 11, 71, doi:10.1186/1743-422X-11-71 (2014).

59 Thompson, E. D., Enriquez, H. L., Fu, Y. X. & Engelhard, V. H. Tumor masses support naive T cell infiltration, activation, and differentiation into effectors. *The Journal of experimental medicine* 207, 1791-1804, doi:10.1084/jem.20092454 (2010).

60 Reddehase, M. J., Fibi, M. R., Keil, G. M. & Koszinowski, U. H. Late-Phase Expression of a Murine Cytomegalovirus Immediate-Early Antigen Recognized by Cytolytic T Lymphocytes. *Journal of Virology* 60, 1125-1129 (1986).

What is claimed is:

1. A method of treating a tumor in a subject by direct intra-tumoral injection of CMV, wherein the intra-tumoral injection enhances the pre-existing immune responses by modulating the tumor micro-environment, through infection of tumor-associated macrophages or other cells in the tumor environment, or through the activation of signaling cascades in response to the presence of the virus in the tumor, directly promoting tumor cell destruction by infecting the tumor cells, and generating new or boosted immune responses against the antigens encoded within the viral genome.

2. The method of claim 1, wherein the CMV encodes for a tumor antigen within the viral genome.

3. The method of claim 1, wherein the CMV is selected from the group consisting of live, virulent, spread-defective, and combinations thereof.

4. The method of claim 1, wherein the CMV is selected from the group consisting of live, virulent, spread-defective CMV, and combinations thereof, and does not encode a tumor antigen within the viral genome.

5. The method of claim 1, wherein the intra-tumoral injection is a onetime injection or a repeated injection.

6. The method of claim 1, further comprising a systemic injection of the CMV.

7. The method of claim 1, wherein the CMV virus retains the pentameric complex consisting of the glycoproteins H and L (gH and gL), along with UL128, UL130 and UL131.

8. The method of claim 1, wherein the intra-tumoral injection of CMV is given in combination with an anti-PD-L1 therapeutic.

9. The method of claim 1, wherein the intra-tumoral injection of CMV is combined with an immune checkpoint inhibitor.

10. The method of claim 1, wherein the intra-tumoral injection of CMV is combined with an immune stimulating therapy.

11. The method of claim 1, wherein the intra-tumoral injection of CMV is combined with an additional tumor therapeutic that promotes tumor cell destruction and/or tumor growth delay.

12. A CMV-based composition comprising: CMV viruses, wherein the CMV is selected from the group consisting of a live, virulent, spread-defective CMV, and combinations thereof that do not encode tumor antigens within the viral genome, a pharmaceutically acceptable carrier, and an immunotherapeutic that blocks PD-1, PD-L1, or a combination thereof.

13. A method of treating cancer comprising administering the composition according to claim 12 via intra-tumoral injection with one or more secondary therapies selected from the group consisting of immunotherapies, chemotherapies, radiation therapies, immune modulating therapies, and other therapies that would be used to promote improved anti-tumor immune responses or tumor cell destruction, wherein said other therapies comprise an inhibitor of one or more immune checkpoint selected from the group consisting of: PD-1, PD-L1, CTLA-4, B7-H3, LAG-3, TIM-3, TIGIT, and IDO.

14. The method of claim 13, wherein said immune modulating therapies comprise one or more therapeutic that binds to one or more immune co-stimulator selected from the group consisting of: OX40, CD27, CD40, and CD40L.

* * * * *

UNITED STATES PATENT AND TRADEMARK OFFICE
CERTIFICATE OF CORRECTION

| | |
|---|---|
| PATENT NO. | : 11,351,237 B2 |
| APPLICATION NO. | : 16/064906 |
| DATED | : June 7, 2022 |
| INVENTOR(S) | : Christopher M. Snyder and Daniel A. Erkes |

Page 1 of 1

It is certified that error appears in the above-identified patent and that said Letters Patent is hereby corrected as shown below:

In the Specification

At Column 1, Line 13, the following paragraph should be inserted:
--STATEMENT REGARDING FEDERALLY SPONSORED RESEARCH OR DEVELOPMENT
This invention was made with government support under CA174979 awarded by the National Institutes of Health. The government has certain rights in the invention.--

Signed and Sealed this
Twenty-fifth Day of March, 2025

Coke Morgan Stewart
*Acting Director of the United States Patent and Trademark Office*